United States Patent
Janssens et al.

(10) Patent No.: US 7,173,054 B2
(45) Date of Patent: Feb. 6, 2007

(54) RESPIRATORY SYNCYTIAL VIRUS REPLICATION INHIBITORS

(75) Inventors: Frans Eduard Janssens, Bonheiden (BE); Kathleen Petrus Marie-José Meersman, Wechelderzande (BE); François Maria Sommen, Wortel (BE); Jérôme Emile Georges Guillemont, Ande (FR); Jean Fernand Armand Lacrampe, Le Mesnil-Esnard (FR); Koenraad Jozef Lodewijk Marcel Andries, Beerse (BE)

(73) Assignee: Janssen Pharmaceutica, N.V., Beerse (BE)

( * ) Notice: Subject to any disclaimer, the term of this patent is extended or adjusted under 35 U.S.C. 154(b) by 26 days.

(21) Appl. No.: 11/144,103

(22) Filed: Jun. 3, 2005

(65) Prior Publication Data

US 2005/0234047 A1    Oct. 20, 2005

Related U.S. Application Data

(62) Division of application No. 10/030,202, filed as application No. PCT/EP00/05676 on Jun. 20, 2000, now Pat. No. 6,924,287.

(30) Foreign Application Priority Data

Jun. 28, 1999    (EP) ................................ 99202087
Feb. 11, 2000    (EP) ................................ 00200452

(51) Int. Cl.
   *C07D 403/04*    (2006.01)
   *C07D 403/12*    (2006.01)
   *C07D 403/14*    (2006.01)
   *A61K 31/4184*    (2006.01)

(52) U.S. Cl. ................ 514/394; 540/470; 540/480; 514/395

(58) Field of Classification Search ................ 540/470, 540/480; 544/357, 364, 370, 238, 295; 546/193, 546/199; 548/306.1, 304.4; 514/394, 395, 514/252.02, 252.03, 252.06, 252.11, 252.14, 514/252.19, 256, 316, 318, 320, 322, 364, 514/365, 372, 374, 339, 378
See application file for complete search history.

(56) References Cited

U.S. PATENT DOCUMENTS 4,634,704 A    1/1987    Janssens et al. ............ 514/253

(Continued)

FOREIGN PATENT DOCUMENTS

EP    0 005 318 A1    11/1979

(Continued)

OTHER PUBLICATIONS

Cecil Textbook of Medicine (20th Edition, vol. 2), 1996 pp. 1739-1747.*

(Continued)

*Primary Examiner*—Kahsay Habte
(74) *Attorney, Agent, or Firm*—Woodcock Washburn LLP

(57) ABSTRACT

This invention concerns the use of compounds of formula (I) wherein $-a^1=a^2-a^3=a^4-$ is a radical of formula —CH=CH—CH=CH—, —N=CH—CH=CH—, —CH=N—CH=CH—, —CH=CH—N=CH—, —CH=CH—CH=N— wherein each hydrogen atom may optionally be substituted; Q is a radical of formulas (b-1), (b-2), (b-3), (b-4), (b-5), (b-6), (b-7), (b-8), G is a direct bond or $C_{1-10}$alkanediyl; $R^1$ is an optionally substituted monocyclic heterocycle; for the manufacture of a medicament for the treatment of viral infections, in particular RSV infections. Certain compounds of formula (I) are new

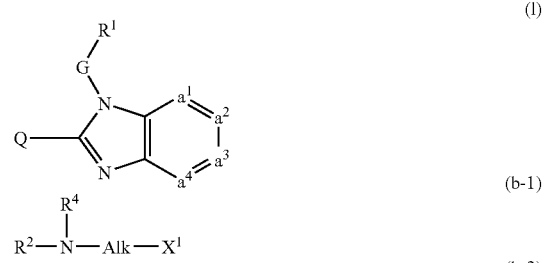

(b-1)

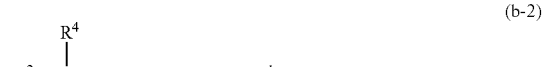

(b-2)

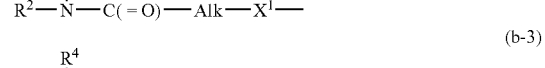

(b-3)

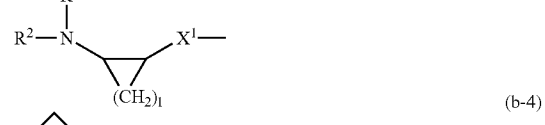

(b-4)

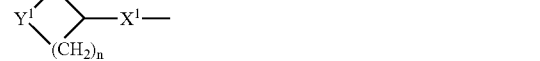

(b-5)

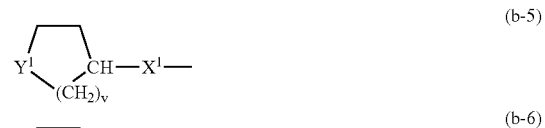

(b-6)

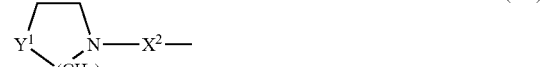

(b-7)

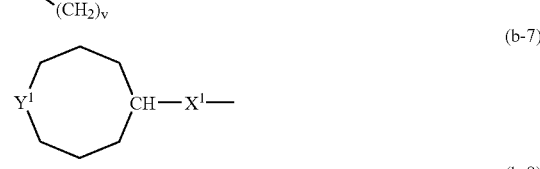

(b-8)

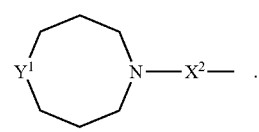

9 Claims, No Drawings

U.S. PATENT DOCUMENTS

| | | | | |
|---|---|---|---|---|
| 4,695,569 A | 9/1987 | Janssens et al. | ............ | 514/258 |
| 5,360,807 A | 11/1994 | Janssens et al. | ............ | 514/318 |
| 5,922,737 A | 7/1999 | Maynard et al. | ............ | 514/318 |
| 5,998,439 A | 12/1999 | Maynard et al. | ............ | 514/318 |
| 6,340,681 B1 * | 1/2002 | Ito | ............ | 514/234.5 |
| 6,924,287 B1 | 8/2005 | Janssens et al. | ....... | 514/252.02 |

FOREIGN PATENT DOCUMENTS

| | | |
|---|---|---|
| EP | 0 099 139 A2 | 1/1984 |
| EP | 0 144 101 A2 | 6/1985 |
| EP | 0 145 037 A2 | 6/1985 |
| EP | 0 151 824 A2 | 8/1985 |
| EP | 0 151 826 A1 | 8/1985 |
| EP | 0 232 937 A2 | 8/1987 |
| EP | 0 295 742 A1 | 12/1988 |
| EP | 0 297 661 A1 | 1/1989 |
| EP | 0 307 014 A1 | 3/1989 |
| EP | 0 393 738 A1 | 10/1990 |
| EP | 0 747 363 A1 | 12/1996 |
| EP | 0 058 146 A1 | 8/2002 |
| WO | WO 92/01687 A1 | 2/1992 |
| WO | WO 92/01697 A1 | 2/1992 |
| WO | WO 98/10764 A1 | 3/1998 |
| WO | WO 98/31363 A1 | 7/1998 |
| WO | WO 98/55120 A1 | 12/1998 |

OTHER PUBLICATIONS

Akula, M. R. et al., "An Improved Synthesis of 3-Phenyl-and 3-Methoxyquinaldine," *Org. Prep. Proced. Int.*, 1991, 23, pp. 386-387.

Bennett, et al., *Cecil Textbook of Medicine*, 20th Edition, vol. 2.

Cerè, V. et al., "Catalytic Hydrogenation of Benzo[2.1.3] Oxadiazoles," *Tetrahedron*, 1972, 28, 3271-3276.

Chiba, T. et al., "Inhibitory Effect of Pyridobenzazoles on Virus Replication in vitro," *Biol Pharm Bull*, 1995, 18(8), 1081-1083.

Goodman and Gilman, "Biotransformation of Drugs," in *The Pharmacological Basis of Therapeutics*, 8th ed., McGraw-Hill, Int. Ed. 1992, 13-15.

Greene, T. et al., *Protective Groups in Organic Synthesis*, John Wiley & Sons Inc., 1991, Chapter 7.

Lindström, S. et al., "Synthesis of the Mutagenic 2-Amino-1, 6-Dimethyl-Imidazo[4,5-b]Pyridine (1,6-DMIP) and Five of Its Isomers," *Heterocycles*, 1994, 38(3), 529-540.

Richardson, Jr. et al. "Study of the Synthesis and Chemistry of the 5,6-Dihydroimidazo[ij]quinoline Series," *J. Org. Chem.*, 1960, 25, 1138-1147.

Tidwell, R. et al., "Aromatic Amidines: Comparison of Their Ability to Block Respiratory Syncytial Virus Induced Cell Fusion and to Inhibit Plasmin, Urokinase, Thrombin, and Trypsin," *J Med Chem*, 1983, 26, 294-298.

Wyde et al., "CL387626 exhibits marked and unusual antiviral activity against respiratory syncytial virus in tissue culture and in cotton rats," *Antivirus Research*, 1998, 38, 31-42.

* cited by examiner

RESPIRATORY SYNCYTIAL VIRUS REPLICATION INHIBITORS

CROSS-REFERENCE TO RELATED APPLICATIONS

This application is a divisional application of U.S. application Ser. No. 10/030,202, filed Dec. 27, 2001, now U.S. Pat. No. 6,924,287 which is the national stage entry under 35 U.S.C. § 371 of PCT/EP00/05676 filed Jun. 20, 2000, which claims priority to EPO 99202087.5 filed Jun. 28, 1999 and EPO 00200452.1 filed Feb. 11, 2000, the disclosures of which are incorporated herein by reference in their entirety.

The present invention is concerned with benzimidazoles and imidazopyridines having antiviral activity, in particular, they have an inhibitory activity on the replication of the respiratory syncytial virus. It further concerns their preparation and compositions comprising them, as well as their use as a medicine.

Human RSV or Respiratory Syncytial Virus is a large RNA virus, member of the family of Paramyxoviridae, subfamily pneumovirinae together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. Ribavirin, a nucleoside analogue, provides an aerosol treatment for serious RSV infection in hospitalized children. The aerosol route of administration, the toxicity (risk of teratogenicity), the cost and the highly variable efficacy limit its use. The other two drugs, Respi-Gam® and palivizumab, polyclonal and monoclonal antibody immunostimulants, are intended to be used in a preventive way.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication.

EP-A-0,005,318, EP-A-0,099,139, EP-A-0,145,037, EP-A-0,144,101, EP-A-0,151,826, EP-A-0,151,824, EP-A-0,232,937, EP-A-0,295,742, EP 0,297,661, EP-A-0,307,014, WO 92 01697 describe benzimidazole and imidazopyridine substituted piperidine and piperazine derivatives as antihistaminics, antiallergics or serotonine antagonists.

The present invention concerns the use of a compound for the manufacture of a medicament for treating viral infections, wherein the compound is a compound of formula

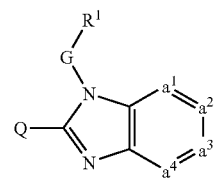
(I)

a prodrug, N-oxide, addition salt, quaternary amine, metal complex and stereochemically isomeric form thereof, wherein
-$a^1$=$a^2$-$a^3$=$a^4$- represents a bivalent radical of formula —CH=CH—CH=CH—  (a-1);

—N=CH—CH=CH—  (a-2);

—CH=N—CH=CH—  (a-3);

—CH=CH—N=CH—  (a-4); or

—CH=CH—CH=N—  (a-5);

wherein each hydrogen atom in the radicals (a-1), (a-2), (a-3), (a-4) and (a-5) may optionally be replaced by halo, $C_{1-6}$alkyl, nitro, amino, hydroxy, $C_6$alkyloxy, polyhalo $C_{1-6}$alkyl, carboxyl, amino$C_{1-6}$alkyl, mono- or di($C_{1-4}$alkyl)amino$C_{1-6}$alkyl, $C_{1-6}$alkyloxycarbonyl, hydroxy $C_{1-6}$alkyl, or a radical of formula

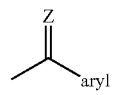

wherein =Z is =O, =CH—C(=O)—NR$^{5a}$R$^{5b}$, =CH$_2$, =CH—C$_{1-6}$alkyl, =N—OH or =N—O—C$_{1-6}$alkyl;
Q is a radical of formula

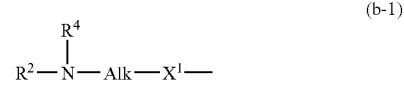
(b-1)

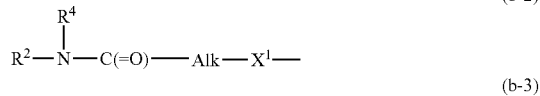
(b-2)

(b-3)

(b-4)

(b-5)

(b-6)

-continued

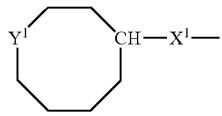
(b-7)

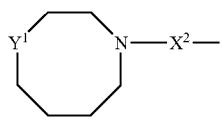
(b-8)

wherein Alk is $C_{1-6}$alkanediyl;

$Y^1$ is a bivalent radical of formula $-NR^2-$ or $-CH(NR^2R^4)-$;

$X^1$ is $NR^4$, S, S(=O), S(=O)$_2$, O, CH$_2$, C(=O), C(=CH$_2$), CH(OH), CH(CH$_3$), CH(OCH$_3$), CH(SCH$_3$), CH(NR$^{5a}$R$^{5b}$), CH$_2$—NR$^4$ or NR$^4$—CH$_2$;

$X^2$ is a direct bond, CH$_2$, C(=O), NR$^4$, $C_{1-4}$alkyl-NR$^4$, NR$^4$—$C_{1-4}$alkyl;

t is 2, 3, 4 or 5;

u is 1, 2, 3, 4 or 5;

v is 2 or 3; and whereby each hydrogen atom in Alk and the carbocycles and the heterocycles defined in radicals (b-3), (b-4), (b-5), (b-6), (b-7) and (b-8) may optionally be replaced by $R^3$; with the proviso that when $R^3$ is hydroxy or $C_{1-6}$alkyloxy, then $R^3$ can not replace a hydrogen atom in the a position relative to a nitrogen atom;

G is a direct bond or $C_{1-10}$alkanediyl;

$R^1$ is a monocyclic heterocycle selected from piperidinyl, piperazinyl, pyridyl, pyrazinyl, pyridazinyl, pyrimidinyl, pyrrolyl, furanyl, tetrahydrofuranyl, thienyl, oxazolyl, thiazolyl, imidazolyl, pyrazolyl, isoxazolyl, oxadiazolyl, and isothiazolyl; and each heterocycle may optionally be substituted with 1 or where possible more, such as 2, 3 or 4, substituents selected from halo, hydroxy, amino, cyano, carboxy, $C_{1-6}$alkyl, $C_{1-6}$alkyloxy, $C_{1-6}$alkylthio, $C_{1-6}$alkyloxy$C_{1-6}$alkyl, aryl, aryl$C_{1-6}$alkyl, aryl$C_{1-6}$alkyloxy, hydroxy$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkylcarbonylamino, $C_{1-6}$alkyl-SO$_2$—NR$^{5c}$—, aryl-SO$_2$—NR$^{5c}$—, $C_{1-6}$alkyloxycarbonyl, C(=O)NR$^{5c}$R$^{5d}$, HO(—CH$_2$—CH$_2$—O)$_n$—, halo(—CH$_2$—CH$_2$—O)$_n$—, $C_{1-6}$alkyloxy(—CH$_2$—CH$_2$—O)$_n$—, aryl$C_{1-6}$alkyloxy (—CH$_2$—CH$_2$—O)$_n$— and mono- or di($C_{1-6}$alkyl)amino (—CH$_2$—CH$_2$—O)$_n$—;

each n independently is 1, 2, 3 or 4;

$R^2$ is hydrogen, formyl, $C_{1-6}$alkylcarbonyl, Hetcarbonyl, pyrrolidinyl, piperidinyl, homopiperidinyl, $C_{3-7}$cycloalkyl substituted with N(R$^6$)$_2$, or $C_{1-10}$alkyl substituted with N(R$^6$)$_2$ and optionally with a second, third or fourth substituent selected from amino, hydroxy, $C_{3-7}$cycloalkyl, $C_{2-5}$alkanediyl, piperidinyl, mono- or di($C_{1-6}$alkyl)amino, $C_{1-6}$alkyloxycarbonylamino, aryl and aryloxy;

$R^3$ is hydrogen, hydroxy, $C_{1-6}$alkyl, $C_{1-6}$alkyloxy, aryl$C_{1-6}$alkyl or aryl$C_{1-6}$alkyloxy;

$R^4$ is hydrogen, $C_{1-6}$alkyl or aryl$C_{1-6}$alkyl;

$R^{5a}$, $R^{5b}$, $R^{5c}$ and $R^{5d}$ each independently are hydrogen or $C_{1-6}$alkyl; or $R^{5a}$ and $R^{5b}$, or $R^{5c}$ and $R^{5d}$ taken together form a bivalent radical of formula —(CH$_2$)$_s$— wherein s is 4 or 5;

$R^6$ is hydrogen, $C_{1-4}$alkyl, formyl, hydroxy$C_{1-6}$alkyl, $C_{1-6}$alkylcarbonyl or $C_{1-6}$alkyloxycarbonyl;

aryl is phenyl or phenyl substituted with 1 or more, such as 2, 3 or 4, substituents selected from halo, hydroxy, $C_{1-6}$alkyl, hydroxy$C_{1-6}$alkyl, polyhalo$C_{1-6}$alkyl, $C_{1-6}$alkyloxy; and Het is pyridyl, pyrimidinyl, pyrazinyl, pyridazinyl.

The present invention also relates to a method of treating warm-blooded animals suffering from or susceptible to viral infections, in particular RSV infection. Said method comprises the administration of a therapeutically effective amount of a compound of formula (I) or a prodrug thereof, a N-oxide form, a pharmaceutically acceptable acid or base addition salt, a quaternary amine, a metal complex or a stereochemically isomeric form thereof in admixture with a pharmaceutical carrier.

A further embodiment of the present invention includes the compounds of formula (I')

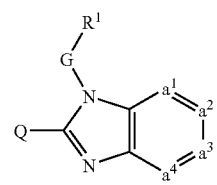
(I')

their prodrugs, N-oxides, addition salts, quaternary amines, metal complexes and stereochemically isomeric forms, wherein -$a^1$=$a^2$-$a^3$=$a^4$- represents a radical of formula —CH=CH—CH=CH— (a-1);

—N=CH—CH=CH— (a-2);

—CH=N—CH=CH— (a-3);

—CH=CH—N=CH— (a-4); or

—CH=CH—CH=N— (a-5);

wherein each hydrogen atom in the radicals (a-1), (a-2), (a-3), (a-4) and (a-5) may optionally be replaced by halo, $C_{1-6}$alkyl, nitro, amino, hydroxy, $C_{1-6}$alkyloxy, polyhalo$C_{1-6}$alkyl, carboxyl, amino$C_{1-4}$alkyl, mono- or di($C_{1-4}$alkyl)amino$C_{1-4}$alkyl, $C_{1-6}$alkyloxycarbonyl, hydroxy $C_{1-6}$alkyl, or a radical of formula

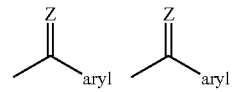

wherein =Z is =O, =CH—C(=O)—NR$^{5a}$R$^{5b}$, =CH$_2$, =CH—$C_{1-6}$alkyl, =N—OH or =N—O—$C_{1-6}$alkyl;

Q is a radical of formula

(b-1)

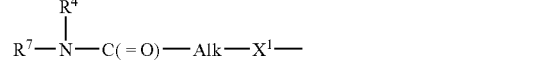
(b-2)

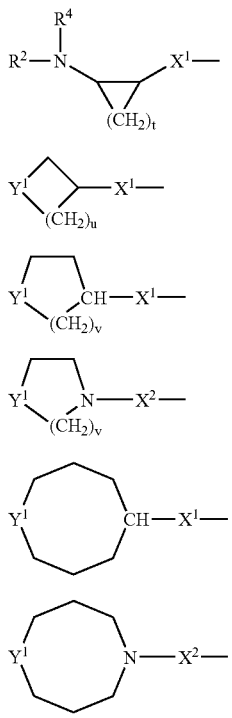

(b-3)
(b-4)
(b-5)
(b-6)
(b-7)
(b-8)

wherein Alk is $C_{1-6}$alkanediyl;
$Y^1$ is a bivalent radical of formula —$NR^2$— or —CH($NR^2R^4$)—;
$X^1$ is $NR^4$, S, S(=O), S(=O)$_2$, O, CH$_2$, C(=O), C(=CH$_2$), CH(OH), CH(CH$_3$), CH(OCH$_3$), CH(SCH$_3$), CH($NR^{5a}R^{5b}$), CH$_2$—$NR^4$ or $NR^4$—CH$_2$;
$X^2$ is a direct bond, CH$_2$, C(=O), $NR^4$, $C_{1-4}$alkyl-$NR^4$, $NR^4$—$C_{1-4}$alkyl;
t is 2, 3, 4 or 5;
u is 1, 2, 3, 4 or 5;
v is 2 or 3; and
whereby each hydrogen atom in Alk and the carbocycles and the heterocycles defined in radicals (b-3), (b-4), (b-5), (b-6), (b-7) and (b-8) may optionally be replaced by $R^3$; with the proviso that when $R^3$ is hydroxy or $C_{1-6}$alkyloxy, then $R^3$ can not replace a hydrogen atom in the a position relative to a nitrogen atom;
G is a direct bond or $C_{1-10}$alkanediyl;
$R^1$ is a monocyclic heterocycle selected from pyridyl, pyrazinyl, pyridazinyl, pyrimidinyl, pyrrolyl, imidazolyl and pyrazolyl; and each heterocycle may optionally be substituted with 1 or where possible more, such as 2, 3 or 4, substituents selected from halo, hydroxy, amino, cyano, carboxy, $C_{1-6}$alkyl, $C_{1-6}$alkyloxy, $C_{1-6}$alkylthio, $C_{1-6}$alkyloxy$C_{1-6}$alkyl, aryl, aryl$C_{1-6}$alkyl, aryl$C_{1-6}$alkyloxy, hydroxy$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkyl-carbonylamino, $C_{1-6}$alkyl-SO$_2$—$NR^{5c}$, aryl-SO$_2$—$NR^{5c}$, $C_{1-6}$alkyloxycarbonyl, —C(=O)—$NR^{5c}R^{5d}$, HO(—CH$_2$—CH$_2$—O)$_n$—, halo(—CH$_2$—CH$_2$—O)$_n$—, $C_{1-6}$alkyloxy(—CH$_2$—CH$_2$—O)$_n$—, aryl$C_{1-6}$alkyloxy(—CH$_2$—CH$_2$—O)$_n$— and mono- or di($C_{1-6}$alkyl)amino(—CH$_2$—CH$_2$—O)$_n$—;
each n independently is 1, 2, 3 or 4;
$R^2$ is hydrogen, formyl, pyrrolidinyl, piperidinyl, homopiperidinyl, $C_{3-7}$cycloalkyl substituted with N($R^6$)$_2$, or $C_{1-10}$alkyl substituted with N($R^6$)$_2$ and optionally with a second, third or fourth substituent selected from amino, hydroxy, $C_{3-7}$cycloalkyl, $C_{2-5}$alkanediyl, piperidinyl, mono- or di($C_{1-6}$alkyl)amino, $C_{1-6}$alkyloxycarbonylamino, aryl and aryloxy;
$R^3$ is hydrogen, hydroxy, $C_{1-6}$alkyl, $C_{1-6}$alkyloxy, aryl$C_{1-4}$alkyl or aryl$C_{1-6}$alkyloxy;
$R^4$ is hydrogen, $C_{1-6}$alkyl or aryl$C_{1-6}$alkyl;
$R^{5a}$, $R^{5b}$, $R^{5c}$ and $R^{5d}$ each independently are hydrogen or $C_{1-6}$alkyl; or
$R^{5a}$ and $R^{5b}$, or $R^{5c}$ and $R^{5d}$ taken together form a bivalent radical of formula —(CH$_2$)$_s$— wherein s is 4 or 5;
$R^6$ is hydrogen, $C_{1-4}$alkyl, formyl, hydroxy$C_{1-6}$alkyl, $C_{1-6}$alkylcarbonyl or $C_{1-6}$alkyloxycarbonyl;
aryl is phenyl or phenyl substituted with 1 or more, such as 2, 3 or 4, substituents selected from halo, hydroxy, $C_{1-6}$alkyl, hydroxy$C_{1-6}$alkyl, polyhalo$C_{1-6}$alkyl, and $C_{1-6}$alkyloxy;
provided that when G is methylene, and $R^1$ is 2-pyridyl, 3-pyridyl, 6-methyl-2-pyridyl, 2-pyrazinyl or 5-methylimidazol-4-yl, and -a$^1$=a$^2$-a$^3$=a$^4$- is —CH=CH—CH=CH— or —N=CH—CH=CH—, then Q is other than

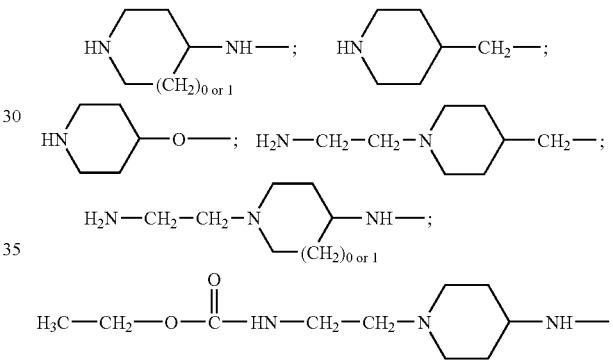

Yet another embodiment of the present invention includes the following group of compounds
2-[[2-[[1-(2-aminoethyl)-4-piperidinyl]amino]-5-chloro-7-methyl-1H-benzimidazol-1-yl]methyl]-6-methyl-3-pyridinol tetrahydrochloride tetrahydrate;
N-[1-(2-aminoethyl)-4-piperidinyl] 1-[(2,4-dimethyl-5-oxazolyl)methyl]-1H-benzimidazol-2-amine;
N-[1-(2-aminoethyl)-4-piperidinyl]-1-[(2,5-dimethyl-4-oxazolyl)methyl]-1H-benzimidazol-2-amine trihydrochloride monohydrate;
4-[[3-[[5-(methoxymethyl)-2-furanyl]methyl]-3H-imidazo[4,5-b]pyridine-2-yl]methyl]-1-piperidineetanamine;
N-[1-(2-aminoethyl)-4-piperidinyl]-1-[(5-methyl-3-isoxazolyl)methyl]-1H-benzimidazol-2-amine trihydrochloride monohydrate;
N-[1-(2-aminoethyl)-4-piperidinyl]-1-[(2-methyl-5-oxazolyl)methyl]-1H-benzimidazol-2-amine monohydrate;
N-[1-(2-aminoethyl)-4-piperidinyl]-1-[(2-methyl-5-oxazolyl)methyl]-1H-benzimidazol-2-amine trihydrochloride monohydrate;
N-[1-(2-aminoethyl)-4-piperidinyl]-3-[(2,4-dimethyl-5-oxazolyl)methyl]-3H-imidazo[4,5-b]pyridin-2-amine;
4-[[3-[(2-methyl-5-oxazolyl)methyl]-3H-imidazo[4,5-b]pyridin-2-yl]methyl]-1-piperazineethanamine;
N-[1-(2-aminoethyl)-4-piperidinyl]-1-(4-thiazolylmethyl)-1H-benzimidazol-2-amine;

N-[1-(2-aminoethyl)-4-piperidinyl]-1-[(5-phenyl-1,2,4-oxa-diazol-3-yl)methyl]-1H-benzimidazol-2-amine trihydrochloride;

5-[[2-[[1-(2-aminoethyl)-4-piperidinyl]amino-1H-benzimidazol-1-yl]methyl-2-oxazolemethanol tetrahydrochloride dihydrate;

N-[1-(2-aminoethyl)-4-piperidinyl]-1-[(3-methyl-5-isoxazolyl)methyl]-1H-benzimidazol-2-amine trihydrochloride monohydrate;

4-[[1-[[2-(dimethylamino)$_4$-thiazolyl]methyl]-1H-benzimidazol-2-yl]methyl]-1-piperidineethanamine tetrahydrochloride monohydrate 2-propanolate (1:1);

ethyl 5-[[2-[[1-[2-[[(1,1-dimethylethoxy)carbonyl]amino]ethyl]4-piperidinyl]amino]-1H-benzimidazol-1-yl]methyl]-2-methyl-4-oxazolecarboxylate;

4-[[1-[(2-methyl-4-thiazolyl)methyl]-1H-benzimidazol-2-yl]methyl]-1-piperidineetahnamine;

N-[1-(2-aminoethyl)-4-piperidinyl]-1-[(2-methyl-3-furanyl)methyl]-1H-benzimidazol-2-amine;

ethyl 4-[[3-[(3-hydroxy-6-methyl-2-pyridinyl)methyl]-7-methyl-3H-imidazo[4,5-b]pyridine-2-yl]amino]-1-piperidinecarboxylate;

1,1-dimethylethyl 4-[[1-[[3-[2-(dimethylamino)ethoxy]-6-methyl-2-pyridinyl]methyl]-1H-benzimidazol-2-yl]amino-1-piperidinecarboxylate;

ethyl 4-[[1-[(3-amino-2-pyridinyl)methyl]-1H-benzimidazol-2-yl]amino]-1-piperidinecarboxylate; and N-[1-(6-methyl-2-pyridinyl)-1H-benzimidazol-2-yl]-1-(3-pyridinylcarbonyl)-4-piperidinamine.

the prodrugs, N-oxides, addition salts, quaternary amines, metal complexes and stereochemically isomeric forms thereof.

Said group of compounds will be referred to hereinafter as the compounds of group (I").

The term prodrug as used throughout this text means the pharmacologically acceptable derivatives, e.g. esters and amides, such that the resulting biotransformation product of the derivative is the active drug as defined in the compounds of formula (I). The reference by Goodman and Gilman (The Pharmacological Basis of Therapeutics, 8$^{th}$ ed., McGraw-Hill, Int. Ed. 1992, "Biotransformation of Drugs", p. 13–15) describing prodrugs generally, is hereby incorporated.

As used herein $C_{1-3}$alkyl as a group or part of a group defines straight or branched chain saturated hydrocarbon radicals having from 1 to 3 carbon atoms such as methyl, ethyl, propyl, 1-methylethyl and the like; $C_{1-4}$alkyl as a group or part of a group defines straight or branched chain saturated hydrocarbon radicals having from 1 to 4 carbon atoms such as the group defined for $C_{1-3}$alkyl and butyl and the like; $C_{2-4}$alkyl as a group or part of a group defines straight or branched chain saturated hydrocarbon radicals having from 2 to 4 carbon atoms such as ethyl, propyl, 1-methylethyl, butyl and the like; $C_{1-6}$alkyl as a group or part of a group defines straight or branched chain saturated hydrocarbon radicals having from 1 to 6 carbon atoms such as the groups defined for $C_{1-4}$alkyl and pentyl, hexyl, 2-methylbutyl and the like; $C_{1-9}$alkyl as a group or part of a group defines straight or branched chain saturated hydrocarbon radicals having from 1 to 9 carbon atoms such as the groups defined for $C_{1-6}$alkyl and heptyl, octyl, nonyl, 2-methylhexyl, 2-methylheptyl and the like; $C_{1-10}$alkyl as a group or part of a group defines straight or branched chain saturated hydrocarbon radicals having from 1 to 10 carbon atoms such as the groups defined for $C_{1-9}$alkyl and decyl, 2-methylnonyl and the like. $C_{3-7}$cycloalkyl is generic to cyclopropyl, cyclobutyl, cyclopentyl, cyclohexyl and cycloheptyl; $C_{2-5}$alkanediyl defines bivalent straight and branched chain saturated hydrocarbon radicals having from 2 to 5 carbon atoms such as, for example, 1,2-ethanediyl, 1,3-propanediyl, 1,4-butanediyl, 1,2-propanediyl, 2,3-butanediyl, 1,5-pentanediyl and the like, $C_{2-5}$alkanediyl is substituted on $C_{1-10}$alkyl as provided for in the definition of $R^2$, it is meant to be substituted on one carbon atom thus forming a spiro moiety; $C_{1-4}$alkanediyl defines bivalent straight and branched chain saturated hydrocarbon radicals having from 1 to 4 carbon atoms such as, for example, methylene, 1,2-ethanediyl, 1,3-propanediyl, 1,4-butanediyl and the like; $C_{1-6}$alkanediyl is meant to include $C_{1-4}$alkanediyl and the higher homologues thereof having from 5 to 6 carbon atoms such as, for example, 1,5-pentanediyl, 1,6-hexanediyl and the like; $C_{1-10}$alkanediyl is meant to include $C_{1-6}$alkanediyl and the higher homologues thereof having from 7 to 10 carbon atoms such as, for example, 1,7-heptanediyl, 1,8-octanediyl, 1,9-nonanediyl, 1,10-decanediyl and the like.

As used herein before, the term (=O) forms a carbonyl moiety when attached to a carbon atom, a sulfoxide moiety when attached to a sulfur atom and a sulfonyl moiety when two of said terms are attached to a sulfur atom. The term (=N—OH) forms a hydroxylimine moiety when attached to a carbon atom.

The term halo is generic to fluoro, chloro, bromo and iodo. As used in the foregoing and hereinafter, polyhalo$C_{1-6}$alkyl as a group or part of a group is defined as mono- or polyhalosubstituted $C_{1-6}$alkyl, in particular methyl with one or more fluoro atoms, for example, difluoromethyl or trifluoromethyl. In case more than one halogen atoms are attached to an alkyl group within the definition of polyhalo$C_{1-4}$alkyl, they may be the same or different.

When any variable (e.g. aryl, $R^2$, $R^3$, $R^4$, $R^{5a}$, $R^{5b}$ etc.) occurs more than one time in any constituent, each definition is independent.

It will be appreciated that some of the compounds of formula (I), (I') or the compounds of group (I") and their prodrugs, N-oxides, addition salts, quaternary amines, metal complexes and stereochemically isomeric forms may contain one or more centers of chirality and exist as stereochemically isomeric forms.

The term "stereochemically isomeric forms" as used hereinbefore defines all the possible stereoisomeric forms which the compounds of formula (I), (I') or the compounds of group (I"), and their prodrugs, N-oxides, addition salts, quaternary amines, metal complexes or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I), (I') or the compounds of group (I") and their prodrugs, N-oxides, salts, solvates, quaternary amines, metal complexes substantially free, i.e. associated with less than 10%, preferably less than 5%, in particular less than 2% and most preferably less than 1% of the other isomers. Stereochemically isomeric forms of the compounds of formula (I), (I') or the compounds of group (I") are obviously intended to be embraced within the scope of this invention. As used hereinafter the terms trans, cis, R or S are well-known by the person skilled in the art.

For some of the compounds of formula (I), (I') or the compounds of group (I"), their prodrugs, N-oxides, salts, solvates, quaternary amines or metal complexes and the intermediates used in the preparation thereof, the absolute stereochemical configuration was not experimentally determined. In these cases the stereoisomeric form which was first isolated is designated as "A" and the second as "B", without further reference to the actual stereochemical configuration. However, said "A" and "B" stereoisomeric forms can be unambiguously characterized by for instance their optical rotation in case "A" and "B" have an enantiomeric relationship. A person skilled in the art is able to determine the absolute configuration of such compounds using art-known methods such as, for example, X-ray diffraction. In case "A" and "B" are stereoisomeric mixtures, they can be further separated whereby the respective first fractions isolated are designated "A1" and "B 1" and the second as "A2" and "B2", without further reference to the actual stereochemical configuration.

For therapeutic use, salts of the compounds of formula (I), (I') or the compounds of group (I") are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I), (I') or the compounds of group (I") are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I), (I') or the compounds of group (I") containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I), (I') or the compounds of group (I") as well as the salts thereof, are able to form. Such solvates are for example hydrates, alcoholates and the like.

The term "quaternary amine" as used hereinbefore defines the quaternary ammonium salts which the compounds of formula (I), (I') or the compounds of group (I") are able to form by reaction between a basic nitrogen of a compound of formula (I), (I') or the compounds of group (I") and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

It will be appreciated that the compounds of formula (I), (I') or the compounds of group (I") may have metal binding, chelating, complexating properties and therefore may exist as metal complexes or metal chelates. Such metalated derivatives of the compounds of formula (I), (I') or the compounds of group (I") are intended to be included within the scope of the present invention.

Some of the compounds of formula (I), (I') or the compounds of group (I") may also exist in their tautomeric form. Such forms although not explicitly indicated in the above formula are intended to be included within the scope of the present invention.

A special group of compounds are those compounds of formula (I) or (I') wherein one or more of the following restrictions apply:

Q is a radical of formula (b-1), (b-3), (b-4), (b-5), (b-6), (b-7) or (b-8);

$X^2$ is a direct bond, $CH_2$ or $C(=O)$;

$R^1$ is a monocyclic heterocycle selected from pyridyl, pyrazinyl, pyridazinyl, pyrimidinyl, pyrrolyl, imidazolyl and pyrazolyl; and each heterocycle may optionally be substituted with 1 or where possible more, such as 2, 3 or 4, substituents selected from halo, hydroxy, amino, cyano, carboxy, $C_{1-6}$alkyl, $C_{1-6}$alkyloxy, $C_{1-6}$alkylthio, $C_{1-6}$alkyloxy$C_{1-6}$alkyl, aryl, aryl$C_{1-6}$alkyl, aryl$C_{1-6}$alkyloxy, hydroxy$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkyl-carbonylamino, $C_{1-6}$alkyl-SO$_2$—NR$^{5c}$—, aryl-SO$_2$—NR$^{5c}$—, $C_{1-6}$alkyloxycarbonyl, —C(=O)—NR$^{5c}$R$^{5d}$, HO(—CH$_2$—CH$_2$—O)$_n$—, halo(—CH$_2$—CH$_2$—O)$_n$—, $C_{1-6}$alkyloxy(—CH$_2$—CH$_2$—O)$_n$—, aryl$C_{1-6}$alkyloxy(—CH$_2$—CH$_2$—O)$_n$— and mono- or di($C_{1-6}$alkyl)amino(—CH$_2$—CH$_2$—O)$_n$—;

$R^2$ is hydrogen, pyrrolidinyl, piperidinyl, homopiperidinyl, $C_{3-7}$cycloalkyl substituted with NHR$^6$, or $C_{1-10}$alkyl substituted with NHR$^6$ and optionally with a second, third or fourth substituent selected from amino, hydroxy, $C_{3-7}$cycloalkyl, $C_{2-5}$alkanediyl, piperidinyl, mono- or di($C_{1-6}$alkyl)amino, $C_{1-6}$alkyloxycarbonylamino, aryl and aryloxy;

$R^3$ is hydrogen, hydroxy, $C_{1-6}$alkyl, $C_{1-6}$alkyloxy or aryl$C_{1-6}$alkyl;

$R^6$ is hydrogen, $C_{1-4}$alkyl, formyl, $C_{1-6}$alkylcarbonyl or $C_{1-6}$alkyloxycarbonyl.

A special group of compounds are those compounds of formula (I') wherein the following restrictions apply:
when Q is

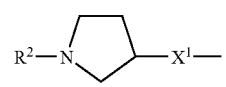

wherein $X^1$ is NR$^4$, O, S, S(=O), S(=O)$_2$, CH$_2$, C(=O), C(=CH$_2$) or CH(CH$_3$), then R$^1$ is other than pyridyl, pyridyl substituted with $C_{1-6}$alkyl, pyrimidinyl, pyrazinyl, imidazolyl and imidazolyl substituted with $C_{1-6}$alkyl;

when Q is

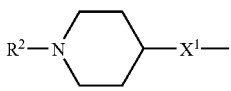

wherein $X^1$ is $NR^4$, O, S, S(=O), S(=O)$_2$, CH$_2$, C(=O), C(=CH$_2$) or CH(CH$_3$), then $R^1$ is other than pyridyl, pyridyl substituted with C$_{1-6}$alkyl, pyridyl substituted with 1 or 2 C$_{1-6}$alkyloxy, pyrazinyl, pyrrolyl, pyrrolyl substituted with C$_{1-6}$alkyl, imidazolyl and imidazolyl substituted with C$_{1-6}$alkyl;
when Q is

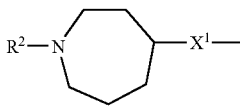

wherein $X^1$ is $NR^4$, O, S, S(=O), S(=O)$_2$, CH$_2$, C(=O), C(=CH$_2$) or CH(CH$_3$), then $R^1$ is other than pyridyl, pyridyl substituted with C$_{1-6}$alkyl, pyrimidinyl, pyrazinyl, imidazolyl and imidazolyl substituted with C$_{1-6}$alkyl;
when Q is

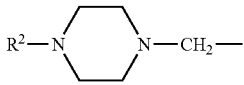

then $R^1$ is other than pyridyl, pyrimidinyl, pyrazinyl, imidazolyl and imidazolyl substituted with C$_{1-6}$alkyl;
when Q is

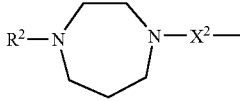

wherein $X^2$ is CH$_2$ or a direct bond, then $R^1$ is other than pyridyl, pyridyl substituted with C$_{1-6}$alkyl, pyrimidinyl, pyrazinyl, imidazolyl and imidazolyl substituted with C$_{1-6}$alkyl.

Or a special group of compounds are those compounds of formula (I') wherein one of the following applies:

Q is a radical of formula (b-1); (b-2); (b-3); (b-5); (b-6); (b-7); (b-8); (b-4) wherein u is 1,3,4 or 5; or (b-4) wherein u is 2, wherein $Y^1$ is —CH(NR$^2$R$^4$)—, wherein $X^1$ is CH(OH), CH(OCH$_3$), CH(SCH$_3$), CH(NR$^{5a}$R$^{5b}$), CH$^2$—NR$^4$ or NR$^4$—CH$_2$, and wherein $R^1$ is pyridyl or imidazolyl, each of said heterocycles substituted with 1 or where possible more, such as 2, 3 or 4, substituents selected from halo, hydroxy, amino, cyano, carboxy, C$_{1-6}$alkyl-oxy, C$_{1-6}$alkylthio, C$_{1-6}$alkyloxyC$_{1-6}$alkyl, aryl, arylC$_{1-6}$alkyl, arylC$_{1-6}$alkyloxy, hydroxyC$_{1-6}$alkyl, mono- or di(C$_{1-6}$alkyl)amino, mono- or di(C$_{1-4}$alkyl)aminoC$_{1-4}$alkyl, polyhaloC$_{1-6}$alkyl, C$_{1-6}$alkylcarbonylamino, C$_{1-6}$alkyl-SO$_2$—NR$^{5c}$—, aryl-SO$_2$—NR$^{5c}$—, C$_{1-6}$alkyloxycarbonyl, —C(=O)—NR$^{5c}$R$^{5d}$, HO(—CH$_2$—CH$_2$—O)$_n$—, halo(—CH$_2$—CH$_2$—O)$_n$—, C$_{1-6}$alkyloxy (—CH$_2$—CH$_2$—O)$_n$—, arylC$_{1-6}$alkyloxy(—CH$_2$—CH$_2$—O)$_n$— and mono- or di(C$_{1-6}$alkyl)amino(—CH$_2$—CH$_2$—O)$_n$—, or each of said heterocycles substituted with, where possible 2, 3 or 4 C$_{1-6}$alkyl groups; or wherein $R^1$ is pyrimidinyl or pyrazinyl, each of said heterocycles being substituted with 1 or where possible more, such as 2, 3 or 4, substituents selected from halo, hydroxy, amino, cyano, carboxy, C$_{1-6}$alkyl, C$_{1-6}$alkyloxy, C$_{1-6}$alkylthio, C$_{1-6}$alkyloxyC$_{1-4}$alkyl, aryl, arylC$_{1-4}$alkyl, arylC$_{1-6}$alkyloxy, hydroxyC$_{1-6}$alkyl, mono- or di(C$_{1-6}$alkyl)amino, mono- or di(C$_{1-6}$alkyl)aminoC$_{1-6}$alkyl, polyhaloC$_{1-6}$alkyl, C$_{1-6}$alkylcarbonylamino, C$_{1-6}$alkyl-SO$_2$—NR$^{5c}$—, aryl-SO$_2$—NR$^{5c}$—, C$_{1-6}$alkyloxycarbonyl, —C(=O)—NR$^{5c}$R$^{5d}$, HO(—CH$_2$—CH$_2$—O)$_n$—, halo(—CH$_2$—CH$_2$—O)$_n$—, C$_{1-6}$alkyloxy(—CH$_2$—CH$_2$—O)$_n$—, arylC$_{1-6}$alkyloxy(—CH$_2$—CH$_2$—O)$_n$— and mono- or di(C$_{1-6}$alkyl)amino(—CH$_2$—CH$_2$—O)$_n$—; or wherein $R^1$ is pyrrolyl or pyrazolyl, each of said heterocycles optionally being substituted with 1 or where possible more, such as 2, 3 or 4, substituents selected from halo, hydroxy, amino, cyano, carboxy, C$_{1-6}$alkyl, C$_{1-6}$alkyloxy, C$_{1-6}$alkylthio, C$_{1-6}$alkyloxyC$_{1-6}$alkyl, aryl, arylC$_{1-6}$alkyl, arylC$_{1-6}$alkyloxy, hydroxyC$_{1-6}$alkyl, mono- or di(C$_{1-4}$alkyl)amino, mono- or di(C$_{1-4}$alkyl)aminoC$_{1-6}$alkyl, polyhaloC$_{1-6}$alkyl, C$_{1-6}$alkylcarbonylamino, C$_{1-6}$alkyl-SO$_2$—NR$^{5c}$—, aryl-SO$_2$—NR$^{5c}$—, C$_{1-6}$alkyloxycarbonyl, —C(=O)—NR$^{5c}$R$^{5d}$, HO(—CH$_2$—CH$_2$—O)$_n$—, halo(—CH$_2$—CH$_2$—O)$_n$—, C$_{1-6}$alkyloxy(—CH$_2$—CH$_2$—O)$_n$—, arylC$_{1-6}$alkyloxy(—CH$_2$—CH$_2$—O)$_n$— and mono- or di(C$_{1-6}$alkyl)amino(—CH$_2$—CH$_2$—O)$_n$—; or Q is a radical of formula (b-1); (b-2); (b-3); (b-4); (b-6); (b-7); (b-8); (b-5) wherein v is 3; or (b-5) wherein v is 2, wherein $Y^1$ is —CH(NR$^2$R$^4$)—, wherein $X^1$ is CH(OH), CH(OCH$_3$), CH(SCH$_3$), CH(NR$^{5a}$R$^{5b}$), CH$_2$—NR$^4$ or NR$^4$—CH$_2$, and wherein $R^1$ is pyrrolyl or imidazolyl, each of said heterocycles being substituted with 1 or where possible more, such as 2, 3 or 4, substituents selected from halo, hydroxy, amino, cyano, carboxy, C$_{1-6}$alkyloxy, C$_{1-6}$alkylthio, C$_{1-6}$alkyloxyC$_{1-6}$alkyl, aryl, arylC$_{1-6}$alkyl, arylC$_{1-6}$alkyloxy, hydroxyC$_{1-6}$alkyl, mono- or di(C$_{1-6}$alkyl)amino, mono- or di(C$_{1-6}$alkyl)aminoC$_{1-6}$alkyl, polyhaloC$_{1-6}$alkyl, C$_{1-6}$alkylcarbonylamino, C$_{1-6}$alkyl-SO$_2$—NR aryl-SO$_2$—NR$^{5c}$—, C$_{1-6}$alkyloxycarbonyl, —C(=O)—NR$^{5c}$R$^{5d}$, HO(—CH$_2$—CH$_2$—O)$_n$—, halo(—CH$_2$—CH$_2$—O)$_n$—, C$_{1-6}$alkyloxy(—CH$_2$—CH$_2$—O)$_n$—, arylC$_{1-6}$alkyloxy(—CH$_2$—CH$_2$—O)$_n$— and mono- or di(C$_{1-6}$alkyl)amino(—CH$_2$—CH$_2$—O)$_n$—, or each of said heterocycles being substituted with, where possible 2, 3 or 4 C$_{1-6}$alkyl groups; or wherein $R^1$ is pyridyl being substituted with 1 or where possible more, such as 2, 3 or 4, substituents selected from halo, hydroxy, amino, cyano, carboxy, C$_{1-6}$alkylthio, C$_{1-6}$alkyloxyC$_{1-6}$alkyl, aryl, arylC$_{1-6}$alkyl, arylC$_{1-4}$alkyloxy, hydroxyC$_{1-6}$alkyl, mono- or di(C$_{1-6}$alkyl)amino, mono- or di(C$_{1-6}$alkyl)aminoC$_{1-6}$alkyl, polyhaloC$_{1-6}$alkyl, C$_{1-6}$alkylcarbonylamino, C$_{1-6}$alkyl-SO$_2$—NR$^{5c}$—, aryl-SO$_2$—NR$^{5c}$, C$_{1-6}$alkyloxycarbonyl, C(=O)NR$^{5c}$R$^{5d}$, HO(—CH$_2$—CH$_2$—O)$_n$—, halo(—CH$_2$—CH$_2$—O)$_n$—, C$_{1-6}$alkyloxy(—CH$_2$—CH$_2$—O)$_n$—, aryl C$_{1-6}$alkyloxy(—CH$_2$—CH$_2$—O)$_n$— and mono- or di(C$_{1-6}$alkyl)amino(—CH$_2$—CH$_2$—O)$_n$—, or pyridyl being substituted with, 2, 3 or 4 C$_{1-6}$alkyl groups or 3 or 4 C$_{1-6}$alkyloxy groups; or wherein $R^1$ is pyrazinyl being substituted with 1 or where possible more, such as 2, 3 or 4, substituents selected from halo, hydroxy, amino, cyano, carboxy, C$_{1-6}$alkyl, C$_{1-6}$alkyloxy, C$_{1-6}$alkylthio, C$_{1-6}$alkyloxyC$_{1-4}$alkyl, aryl, arylC$_{1-6}$alkyl, arylC$_{1-6}$alkyloxy, hydroxyC$_{1-6}$alkyl, mono- or di(C$_{1-6}$alkyl)amino, mono- or di(C$_{1-6}$alkyl)aminoC$_{1-6}$alkyl, polyhaloC$_{1-6}$alkyl, C$_{1-6}$alkyl-carbonylamino, C$_{1-6}$alkyl-SO$_2$—NR$^{5c}$—, aryl-SO$_2$—NR$^{5c}$—, C$_{1-6}$alkyloxycarbonyl, —C(=O)—NR$^{5c}$R$^{5d}$, HO(—CH$_2$—CH$_2$—O)$_n$—, halo(—CH$_2$—CH$_2$—O)$_n$—, C$_{1-6}$alkyloxy(—CH$_2$—CH$_2$—O)$_n$—, arylC$_{1-6}$alkyloxy(—CH$_2$—CH$_2$—O)$_n$— and mono- or di(C$_{1-6}$alkyl)amino(—CH$_2$—CH$_2$—O)$_n$—; or wherein R$^1$ is pyridazinyl, pyrimidinyl or pyrazolyl, each of said heterocycles optionally being substituted with 1 or where possible more, such as 2, 3 or 4, substituents selected from halo, hydroxy, amino, cyano, carboxy, C$_{1-6}$alkyl, C$_{1-6}$alkyloxy, C$_{1-6}$alkylthio, C$_{1-6}$alkyloxyC$_{1-6}$alkyl, aryl, arylC$_{1-6}$alkyl, arylC$_{1-6}$alkyloxy, hydroxyC$_{1-6}$alkyl, mono- or di(C$_{1-6}$alkyl)amino, mono- or di(C$_{1-6}$alkyl)aminoC$_{1-6}$alkyl, polyhaloC$_{1-6}$alkyl, C$_{1-6}$alkyl-carbonylamino, C$_{1-6}$alkyl-SO$_2$—NR$^{5c}$—, aryl-SO$_2$—NR$^{5c}$—, C$_{1-6}$alkyloxycarbonyl, —C(=O)—NR$^{5c}$R$^{5d}$HO(—CH$_2$—CH$_2$—O)$_n$—, halo(—CH$_2$—CH$_2$—O)$_n$—, C$_{1-6}$alkyloxy(—CH$_2$—CH$_2$—O)$_n$—, arylC$_{1-6}$alkyloxy(—CH$_2$—CH$_2$—O)$_n$— and mono- or di(C$_{1-6}$alkyl)amino(—CH$_2$—CH$_2$—O)$_n$—; or Q is a radical of formula (b-1); (b-2); (b-3); (b-4); (b-6); (b-7); (b-8); (b-5) wherein v is 2; or (b-5) wherein v is 3, wherein Y$^1$ is —CH(NR$^2$R$^4$)—, wherein X$^1$ is CH(OH), CH(OCH$_3$), CH(SCH$_3$), CH(NR$^{5a}$R$^{5b}$), CH$_2$—NR$^4$ or NR$^4$—CH$_2$, and wherein R$^1$ is pyridyl or imidazolyl, each of said heterocycles being substituted with 1 or where possible more, such as 2, 3 or 4, substituents selected from halo, hydroxy, amino, cyano, carboxy, C$_{1-6}$alkyloxy, C$_{1-6}$alkylthio, C$_{1-6}$alkyloxyC$_{1-6}$alkyl, aryl, arylC$_{1-6}$alkyl, arylC$_{1-6}$alkyloxy, hydroxyC$_{1-6}$alkyl, mono- or di(C$_{1-6}$alkyl)amino, mono- or di(C$_{1-6}$alkyl)aminoC$_{1-6}$alkyl, polyhaloC$_{1-6}$alkyl, C$_{1-6}$alkylcarbonylamino, C$_{1-6}$alkyl-SO$_2$—NR$^{5c}$—, aryl-SO$_2$—NR$^{5c}$—, C$_{1-6}$alkyloxycarbonyl, —C(=O)—NR$^{5c}$R$^{5d}$, HO(—CH$_2$—CH$_2$—O)—, halo(—CH$_2$—CH$_2$—O)$_n$—, C$_{1-6}$alkyloxy(—CH$_2$—CH$_2$—O)$_n$—, arylC$_{1-6}$alkyloxy(—CH$_2$—CH$_2$—O)$_n$— and mono- or di(C$_{1-6}$alkyl)amino(—CH$_2$—CH$_2$—O)$_n$—, or each of said heterocycles being substituted with, where possible 2, 3 or 4 C$_{1-6}$alkyl groups; or wherein R$^1$ is pyrimidinyl or pyrazinyl, each of said heterocycles being substituted with 1 or where possible more, such as 2, 3 or 4, substituents selected from halo, hydroxy, amino, cyano, carboxy, C$_{1-6}$alkyl, C$_{1-6}$alkyloxy, C$_{1-6}$alkylthio, C$_{1-6}$alkyloxyC$_{1-6}$alkyl, aryl, arylC$_{1-6}$alkyl, arylC$_{1-6}$alkyloxy, hydroxyC$_{1-6}$alkyl, mono- or di(C$_{1-6}$alkyl)amino, mono- or di(C$_{1-6}$alkyl)aminoC$_{1-6}$alkyl, polyhaloC$_{1-6}$alkyl, C$_{1-6}$alkylcarbonylamino, C$_{1-6}$alkyl-SO$_2$—NR$^{5c}$—, aryl-SO$_2$—NR$^{5c}$—, C$_{1-6}$alkyloxycarbonyl, —C(=O)—NR$^{5c}$R$^{5d}$, HO(—CH$_2$—CH$_2$—O)$_n$—, halo(—CH$_2$—CH$_2$—O)$_n$—, C$_{1-6}$alkyloxy(—CH$_2$—CH$_2$—O)$_n$—, arylC$_{1-6}$alkyloxy(—CH$_2$—CH$_2$—O)$_n$— and mono- or di(C$_{1-6}$alkyl)amino(—CH$_2$—CH$_2$—O)$_n$—; or wherein R$^1$ is pyrrolyl or pyrazolyl, each of said heterocycles optionally being substituted with 1 or where possible more, such as 2, 3 or 4, substituents selected from halo, hydroxy, amino, cyano, carboxy, C$_{1-6}$alkyl, C$_{1-6}$alkyloxy, C$_{1-6}$alkylthio, C$_{1-6}$alkyloxyC$_{1-6}$alkyl, aryl, arylC$_{1-6}$alkyl, arylC$_{1-6}$alkyloxy, hydroxyC$_{1-6}$alkyl, mono- or di(C$_{1-6}$alkyl)amino, mono- or di(C$_{1-6}$alkyl)aminoC$_{1-6}$alkyl, polyhaloC$_{1-6}$alkyl, C$_{1-6}$alkylcarbonylamino, C$_{1-6}$alkyl-SO$_2$—NR$^{5c}$—, aryl-SO$_2$—NR$^{5c}$—, C$_{1-6}$alkyloxycarbonyl, —C(=O)—NR$^{5c}$R$^{5d}$, HO(—CH$_2$—CH$_2$—O)$_n$—, halo(—CH$_2$—CH$_2$—O)$_n$—, C$_{1-6}$alkyloxy(—CH$_2$—CH$_2$—O)$_n$—, arylC$_{1-6}$alkyloxy(—CH$_2$—CH$_2$—O)$_n$— and mono- or di(C$_{1-6}$alkyl)amino(—CH$_2$—CH$_2$—O)$_n$—; or Q is a radical of formula (b-1); (b-2); (b-3); (b-4); (b-5); (b-7); (b-8); (b-6) wherein v is 3; or (b-6) wherein v is 2, wherein Y$^1$ is —CH(NR$^2$R$^4$)—, wherein X$^2$ is a direct bond or C(=O), or X$^2$ is a direct bond, C(=O), NR$^4$, C$_{1-4}$alkyl-NR$^4$, NR$^4$—C$_{1-4}$alkyl, wherein R$^1$ is pyridyl, pyrimidinyl or pyrazinyl, each of said heterocycles being substituted with 1 or where possible more, such as 2, 3 or 4, substituents selected from halo, hydroxy, amino, cyano, carboxy, C$_{1-6}$alkyl, C$_{1-6}$alkyloxy, C$_{1-6}$alkylthio, C$_{1-6}$alkyloxyC$_{1-6}$alkyl, aryl, arylC$_{1-6}$alkyl, arylC$_{1-6}$alkyloxy, hydroxyC$_{1-6}$alkyl, mono- or di(C$_{1-6}$alkyl)amino, mono- or di(C$_{1-6}$alkyl)aminoC$_{1-6}$alkyl, polyhaloC$_{1-6}$alkyl, C$_{1-6}$alkylcarbonylamino, C$_{1-6}$alkyl-SO$_2$—NR$^{5c}$—, aryl-SO$_2$—NR$^{5c}$—, C$_{1-6}$alkyloxycarbonyl, —C(=O)—NR$^{5c}$R$^{5d}$, HO(—CH$_2$—CH$_2$—O)$_n$—, halo(—CH$_2$—CH$_2$—O)$_n$—, C$_{1-6}$alkyloxy(—CH$_2$—CH$_2$—O)$_n$—, arylC$_{1-6}$alkyloxy(—CH$_2$—CH$_2$—O)$_n$— and mono- or di(C$_{1-6}$alkyl)amino(—CH$_2$—CH$_2$—O)$_n$—; or wherein R$^1$ is imidazolyl being substituted with 1 or where possible more, such as 2, 3 or 4, substituents selected from halo, hydroxy, amino, cyano, carboxy, C$_{1-6}$alkyloxy, C$_{1-6}$alkylthio, C$_{1-6}$alkyloxyC$_{1-6}$alkyl, aryl, arylC$_{1-6}$alkyl, arylC$_{1-6}$alkyloxy, hydroxyC$_{1-6}$alkyl, mono- or di(C$_{1-6}$alkyl)amino, mono- or di(C$_{1-6}$alkyl)aminoC$_{1-6}$alkyl, polyhaloC$_{1-6}$alkyl, C$_{1-4}$alkyl-carbonylamino, C$_{1-6}$alkyl R$^5$, aryl-SO$_2$—NR$^{5c}$—, C$_{1-6}$alkyloxycarbonyl, —C(=O)—NR$^{5c}$R$^{5d}$, HO(—CH$_2$—CH$_2$—O)$_n$—, halo(—CH$_2$—CH$_2$—O)$_n$—, C$_{1-6}$alkyloxy(—CH$_2$—CH$_2$—O)$_n$—, arylC$_{1-6}$alkyloxy(—CH$_2$—CH$_2$—O)$_n$— and mono- or di(C$_{1-6}$alkyl)amino(—CH$_2$—CH$_2$—O)$_n$—, or imidazolyl being substituted with 2 or 3 C$_1$alkyl groups; or wherein R$^1$ is pyridazinyl, pyrrolyl, or pyrazolyl, each of said heterocycles optionally being substituted with 1 or where possible more, such as 2, 3 or 4, substituents selected from halo, hydroxy, amino, cyano, carboxy, C$_{1-6}$alkyl, C$_{1-6}$alkyloxy, C$_{1-6}$alkylthio, C$_{1-6}$alkyloxyC$_{1-6}$alkyl, aryl, arylC$_{1-6}$alkyl, arylC$_{1-6}$alkyloxy, hydroxyC$_{1-6}$alkyl, mono- or di(C$_{1-6}$alkyl)amino, mono- or di(C$_{1-6}$alkyl)aminoC$_{1-6}$alkyl, polyhaloC$_{1-6}$alkyl, C$_{1-6}$alkylcarbonylamino, C$_{1-6}$alkyl-SO$_2$—NR$^{5c}$—, aryl-SO$_2$—NR$^{5c}$—, C$_{1-6}$alkyloxycarbonyl, —C(=O)—NR$^{5c}$R$^{5d}$, HO(—CH$_2$—CH$_2$—O)$_n$—, halo(—CH$_2$—CH$_2$—O)$_n$—, C$_{1-6}$alkyloxy(—CH$_2$—CH$_2$—O)$_n$—, arylC$_{1-6}$alkyloxy(—CH$_2$—CH$_2$—O)$_n$— and mono- or di(C$_{1-6}$alkyl)amino(—CH$_2$—CH$_2$—O)$_n$—; or Q is a radical of formula (b-1); (b-2); (b-3); (b-4); (b-5); (b-7); (b-8); (b-6) wherein v is 2; or (b-6) wherein v is 3, Y$^1$ is —CH(NR$^2$R$^4$)—, wherein X$^2$ is C(=O) or X$^2$ is C(=O), NR$^4$, C$_{1-4}$alkyl-NR$^4$, NR$^4$—C$_{1-4}$alkyl, and wherein R$^1$ is pyridyl or imidazolyl, each of said heterocycles being substituted with 1 or where possible more, such as 2, 3 or 4, substituents selected from halo, hydroxy, amino, cyano, carboxy, C$_{1-6}$alkyloxy, C$_{1-6}$alkylthio, C$_{1-6}$alkyloxyC$_{1-6}$alkyl, aryl, arylC$_{1-6}$alkyl, arylC$_{1-6}$alkyloxy, hydroxyC$_{1-6}$alkyl, mono- or di(C$_{1-6}$alkyl)amino, mono- or di(C$_{1-6}$alkyl)aminoC$_{1-6}$alkyl, polyhaloC$_{1-6}$alkyl, C$_{1-6}$alkylcarbonylamino, C$_{1-6}$alkyl-SO$_2$—NR$^{5c}$—, aryl-SO$_2$—NR$^{5c}$—, C$_{1-6}$alkyloxycarbonyl, —C(=O)—NR$^{5c}$R$^{5d}$, HO(—CH$_2$—CH$_2$—O)$_n$—, halo(—CH$_2$—CH$_2$—O)$_n$—, C$_{1-6}$alkyloxy(—CH$_2$—CH$_2$—O)$_n$—, arylC$_{1-6}$alkyloxy(—CH$_2$—CH$_2$—O)$_n$— and mono- or di(C$_{1-6}$alkyl)amino(—CH$_2$—CH$_2$—O)$_n$—, or each of said heterocycles being substituted with, where possible 2, 3 or 4 C$_{1-6}$alkyl groups; or wherein R$^1$ is pyrimidinyl or pyrazinyl, each of said heterocycles being substituted with 1 or where possible more, such as 2, 3 or 4, substituents selected from halo, hydroxy, amino, cyano, carboxy, $C_{1-6}$alkyl, $C_{1-6}$alkyloxy, $C_{1-6}$alkylthio, $C_{1-6}$alkyloxy$C_{1-6}$alkyl, aryl, aryl$C_{1-6}$alkyl, aryl$C_{1-6}$alkyloxy, hydroxy$C_1$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkyl-carbonylamino, $C_{1-6}$alkyl-$SO_2$—$NR^{5c}$—, aryl-$SO_2$—$NR^{5c}$—, $C_{1-6}$alkyloxycarbonyl, —C(=O)—$NR^{5c}R^{5d}$, HO(—$CH_2$—$CH_2$—O)$_n$—, halo(—$CH_2$—$CH_2$—O)$_n$—, $C_{1-6}$alkyloxy(—$CH_2$—$CH_2$—O)$_n$—, aryl$C_{1-6}$alkyloxy(—$CH_2$—$CH_2$—O)$_n$— and mono- or di($C_{1-6}$alkyl)amino(—$CH_2$—$CH_2$—O)$_n$—; or wherein $R^1$ is pyrrolyl or pyrazolyl, each of said heterocycles optionally being substituted with 1 or where possible more, such as 2, 3 or 4, substituents selected from halo, hydroxy, amino, cyano, carboxy, $C_{1-6}$alkyl, $C_{1-6}$alkyloxy, $C_{1-6}$alkylthio, $C_{1-6}$alkyloxy$C_{1-6}$alkyl, aryl, aryl$C_{1-6}$alkyl, aryl$C_{1-6}$alkyloxy, hydroxy$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkyl-carbonylamino, $C_{1-6}$alkyl-$SO_2$—$NR^{5c}$—, aryl$C_{1-6}$alkyloxycarbonyl, —C(=O)—$NR^{5c}R^{5d}$, HO(—$CH_2$—$CH_2$—O)$_n$—, halo(—$CH_2$—$CH_2$—O)$_n$—, $C_{1-6}$alkyloxy(—$CH_2$—$CH_2$—O)$_n$—, aryl$C_{1-6}$alkyloxy(—$CH_2$—$CH_2$—O)$_n$— and mono- or di($C_{1-6}$alkyl)amino(—$CH_2$—$CH_2$—O)$_n$—.

Preferred compounds are (±)-2-[[2-[[1-(2-amino-3-methylbutyl)-4-piperidinyl]amino]-7-methyl-1H-benzimidazol-1-yl]methyl]-6-methyl-3-pyridinol tetrahydrochloride monohydrate;

2-[[2-[[1-(2-aminoethyl)-4-piperidinyl]amino]-1H-benzimidazol-1-yl]methyl]-3-pyridinol;

(±)-N-[1-(2-amino-3-methylbutyl)-4-piperidinyl]-6-chloro-1-[(1,4-dimethyl-1H-imidazol-5-yl)methyl]-1H-benzimidazol-2-amine monohydrate;

(±)-N-[1-(2-amino-3-methylbutyl)-4-piperidinyl]-6-chloro-1-[(6-methyl-2-pyridinyl)methyl]-1H-benzimidazol-2-amine;

(±)-2-[[2-[(3-amino-2-hydroxypropyl)amino]-1H-benzimidazol-1-yl]methyl]-6-methyl-3-pyridinol;

N-[1-(2-aminoethyl)-4-piperidinyl]-1-[[3-(2-ethoxyethoxy)-6-methyl-2-pyridinyl]methyl]-1H-benzimidazol-2-amine tetrahydrochloride dihydrate;

(±)-N-[1-(2-amino-3-methylbutyl)4-piperidinyl]-1-[(2-chloro-1,4-dimethyl-1H-imidazol-5-yl)methyl]-1H-benzimidazol-2-amine;

(±)-N-[1-(2-amino-3-methylbutyl)-4-piperidinyl]-6-chloro-1-[(2-chloro-1,4-dimethyl-1H-imidazol-5-yl)methyl]-1H-benzimidazol-2-amine;

(±)-N-[1-(2-amino-3-methylbutyl)-4-piperidinyl]-6-methyl-1-[(6-methyl-2-pyridinyl)methyl]-1H-benzimidazol-2-amine;

(±)-N-[1-(2-aminopropyl)-4-piperidinyl]-1-[(3,5,6-trimethylpyrazinyl)methyl]-1H-benzimidazol-2-amine tetrahydrochloride trihydrate;

(±)-N-[1-(2-amino-3-methylbutyl)-4-piperidinyl]-1-[(3,5,6-trimethylpyrazinyl)methyl]-1H-benzimidazol-2-amine;

N-[1-(2-aminoethyl)-4-piperidinyl]-1-[[3-(2-chloroethoxy)-6-methyl-2-pyridinyl]methyl]-1H-benzimidazol-2-amine trihydrochloride dihydrate;

(±)-N-[1-(2-amino-3-methylbutyl)-4-piperidinyl]1-[3-amino-2-pyridinyl)methyl]-1H-benzimidazol-2-amine tetrahydrochloride trihydrate;

the prodrugs, N-oxides, addition salts, quaternary amines, metal complexes and stereochemically isomeric forms thereof.

Most preferred are

2-[[2-[[1-(2-aminoethyl)-4-piperidinyl]amino]4-methyl-1H-benzimidazol-1-yl]methyl]-6-methyl-3-pyridinol tetrahydrochloride;

(±)-2-[[2-[[1-(2-amino-3-methylbutyl)-4-piperidinyl]amino]-7-methyl-3H-imidazo[4,5-b]pyridin-3-yl]methyl]-6-methyl-3-pyridinol;

2-[[2-[[1-(2-aminoethyl)-4-piperidinyl]amino]-6-chloro-4-methyl-1H-benzimidazol 1-yl]methyl]-6-methyl-3-pyridinol tetrahydrochloride 2-propanolate (1:1);

(±)-2-[[2-[[1-(2-amino-3-methylbutyl)-4-piperidinyl]amino]4-methyl-1H-benzimidazol-1-yl]methyl]-6-methyl-3-pyridinol;

(±)-2-[[2-[[1-(2-aminopropyl)-4-piperidinyl]amino]4-methyl-1H-benzimidazol-1-yl]methyl]-6-methyl-3-pyridinol tetrahydrochloride trihydrate;

2-[[2-[[1-(2-aminoethyl)-4-piperidinyl]amino]-7-methyl-1H-benzimidazol-1-yl]methyl]-6-methyl-3-pyridinol tetrahydrochloride dihydrate;

2-[[2-[[1-(2-aminoethyl)-4-piperidinyl]amino]-6-bromo-4-methyl-1H-benzimidazol-1-yl]methyl]-6-methyl-3-pyridinol tetrahydrochloride;

2-[[2-[[1-(2-aminoethyl)-4-piperidinyl]amino]-1H-benzimidazol-1-yl]methyl]-6-methyl-3-pyridinol tetrahydrochloride monohydrate;

(±)-2-[[2-[[1-(2-amino-3-methylbutyl)-4-piperidinyl]amino]-1H-benzimidazol 1-yl]methyl]-6-methyl-3-pyridinol; and (±)-N-[1-(2-amino-3-methylbutyl)-4-piperidinyl]4-methyl-1-[(6-methyl-2-pyridinyl)-methyl]-1H-benzimidazol-2-amine.

the prodrugs, N-oxides, addition salts, quaternary amines, metal complexes and stereochemically isomeric forms thereof.

In general, compounds of formula (I') can be prepared by reacting an intermediate of formula (II-a) or (II-b), wherein P represents a protecting group, such as, for example $C_{1-4}$alkyloxycarbonyl, or those protecting groups mentioned in Chapter 7 of 'Protective Groups in Organic Synthesis' by T Greene and P. Wuyts (John Wiley & Sons Inc., 1991), with an intermediate of formula (111), wherein $W_1$ is a suitable leaving group, such as a halo atom, e.g. chloro, bromo, in the presence of a suitable base, such as, e.g. sodium hydride, disodium carbonate. Said reaction can be performed in a reaction-inert solvent, such as N,N-dimethylformamide.

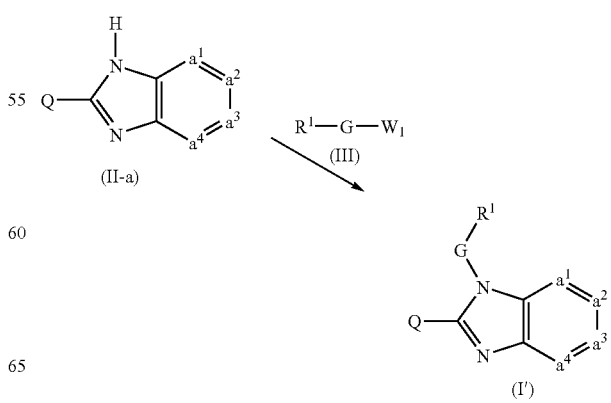

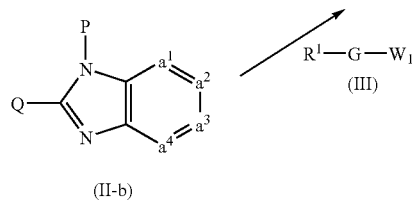
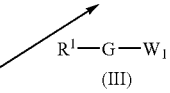

(II-b)

Compounds of formula (I') wherein, in the definition of Q, $R^2$ or at least one $R^6$ substituent is hydrogen, said Q being represented by H-$Q_1$, and said compounds being represented by formula (I'-a), can be prepared by deprotecting an intermediate of formula (IV) wherein P represents a protecting group, for example $C_{1-4}$alkyloxycarbonyl, benzyl, or those protecting groups mentioned in Chapter 7 of 'Protective Groups in Organic Synthesis' by T Greene and P. Wuyts (John Wiley & Sons Inc., 1991).

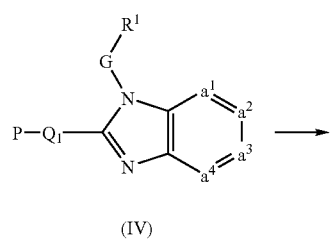

(IV)

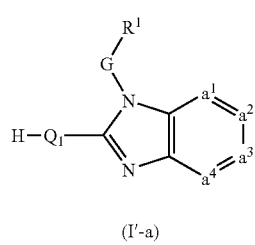

(I'-a)

When P represents, for example, $C_{1-4}$alkyloxycarbonyl, said deprotection reaction can be performed by, for example, acidic hydrolysis in the presence of a suitable acid, such as hydrobromic, hydrochloric, sulfuric, acetic, or trifluoroacetic acid or a mixture of said acids, or by alkaline hydrolysis in the presence of a suitable base, such as, for example potassium hydroxide, in a suitable solvent such as water, alcohol, a mixture of water-alcohol, methylene chloride. Suitable alcohols are methanol, ethanol, 2-propanol, 1-butanol and the like. In order to enhance the rate of the reaction, it is advantageous to heat the reaction mixture, in particular up to the reflux temperature. Alternatively, when P represents, for example, benzyl, the deprotection reaction can be performed by catalytic hydrogenation in the presence of hydrogen and an appropriate catalyst in a reaction-inert solvent. A suitable catalyst in the above reaction is, for example, platinum-on-charcoal, palladium-on-charcoal, and the like. An appropriate reaction-inert solvent for said reaction is, for example, an alcohol, e.g. methanol, ethanol, 2-propanol and the like, an ester, e.g. ethylacetate and the like, an acid, e.g. acetic acid and the like.

The catalytic hydrogenation reaction described above can also be used to prepare a compound of formula (I'-a) by deprotecting and reducing an intermediate of formula (IV) wherein $Q_1$ comprises an unsaturated bond, said $Q_1$ being represented by $Q_{1a}$(CH=CH), and said intermediate being represented by formula (IV-a).

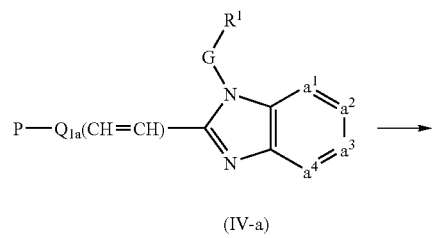

(IV-a)

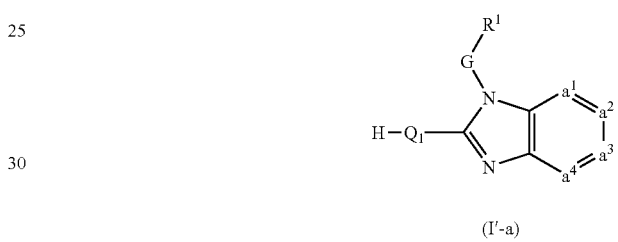

(I'-a)

Compounds of formula (I') wherein, in the definition of Q, both $R^6$ substituents are hydrogen or $R^2$ and $R^4$ are both hydrogen, said Q being represented by $H_2N$-$Q_2$, and said compounds being represented by formula (I'-a-1), can also be prepared by deprotecting an intermediate of formula (V).

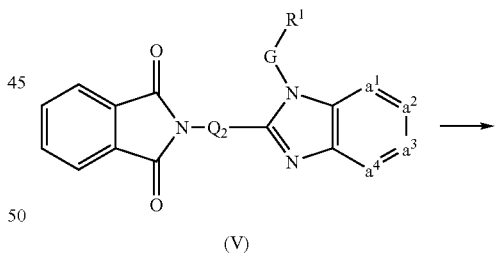

(V)

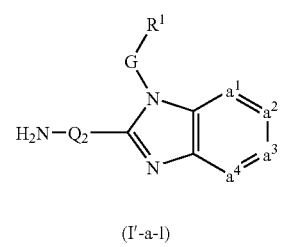

(I'-a-1)

Said deprotection reaction can be performed in the presence of a suitable base such as, for example hydrazine, or in the presence of a suitable acid, such as hydrochloric acid and the like, in a suitable solvent, such as an alcohol, acetic acid and the like.

Compounds of formula (I'-a-1) can also be prepared by deprotecting an intermediate of formula (VI) according to the procedure described for the preparation of compounds of formula (I'-a).

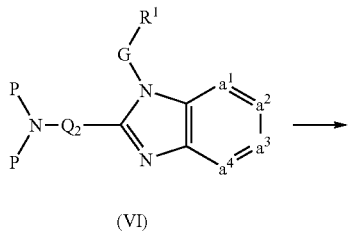

(VI)

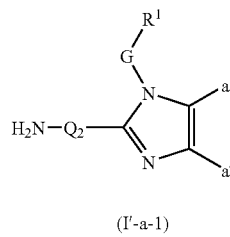

(I'-a-1)

Compounds of formula (I'-a) or (I'-a-1), wherein $Q_1$ or $Q_2$ comprise a hydroxy substituent, said $Q_1$ or $Q_2$ being represented by $Q_{1'}(OH)$ or $Q_{2'}(OH)$, and said compounds being represented by formula (I'-a-2) or (I'-a-1-1), can be prepared by deprotecting an intermediate of formula (VII) or (VIII) as described hereinabove for the preparation of compounds of formula (I'-a).

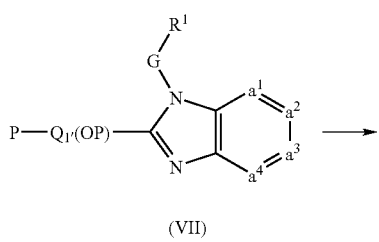

(VII)

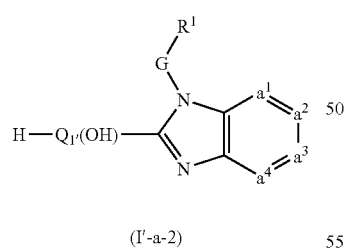

(I'-a-2)

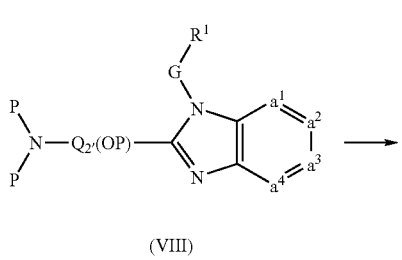

(VIII)

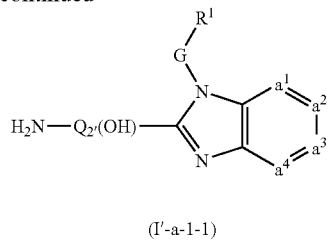

(I'-a-1-1)

Compounds of formula (I') wherein, in the definition of Q, both $R^6$ substituents are hydrogen or $R^2$ and $R^4$ are both hydrogen, and the carbon adjacent to the nitrogen carrying the $R^6$ or $R^2$ and $R^4$ substituents, contains at least one hydrogen, said Q being represented by $H_2N$-$Q_3H$, and said compounds being represented by formula (I'-a-1-2) can also be obtained by reductive amination of intermediates of formula (IX) in the presence of a suitable amination reagent, such as, for example, ammonia, hydroxylamine, or benzylamine, and in the presence of a suitable reducing agent, e.g. hydrogen, and an appropriate catalyst. An appropriate catalyst in the above reaction is, for example, platinum-on-charcoal, palladium-on-charcoal, rhodium-on-$Al_2O_3$, and the like, optionally in the presence of a catalyst poison, such as a thiophene solution. A suitable reaction-inert solvent for the above reaction is, for example, an alcohol, e.g. methanol, ethanol, 2-propanol and the like.

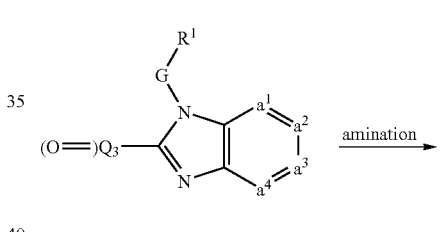

(IX)

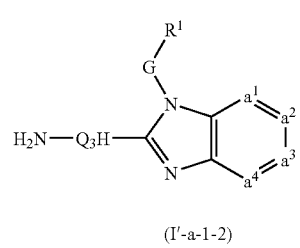

(I'-a-1-2)

Compounds of formula (I'), wherein Q comprises a —$CH_2NH_2$ moiety, said Q being represented by $H_2N$—$CH_2$-$Q_4$, and said compounds being represented by formula (I'-a-1-3) can be prepared by reducing an intermediate of formula (X).

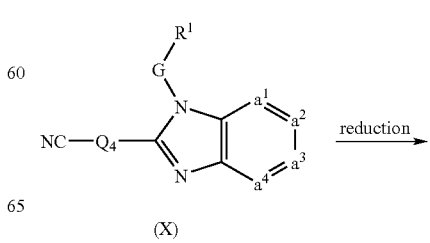

(X)

-continued

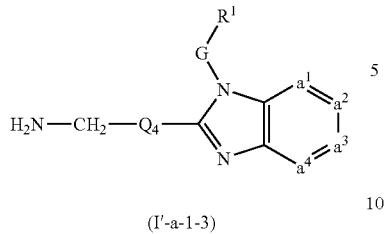

(I'-a-1-3)

Said reduction can be performed with a suitable reducing agent, such as lithium aluminium hydride or hydrogen, optionally in the presence of a suitable catalyst, such as Raney Nickel. A suitable solvent for the above reaction is, for example, tetrahydrofuran, or a solution of ammonia in an alcohol. Suitable alcohols are methanol, ethanol, 2-propanol and the like. Said reduction reaction performed in a solution of ammonia in an alcohol can also be used to prepare compounds of formula (I'-a-1-3), wherein $R^1$ is substituted with $C_{1-6}$alkyloxy$C_{1-6}$alkyl, said $R^1$ being represented by $R^{1'}$—$C_{1-6}$alkyloxy$C_{1-6}$alkyl, and said compounds being represented by formula (I'-a-1-3-1) starting from an intermediate of formula (X-a).

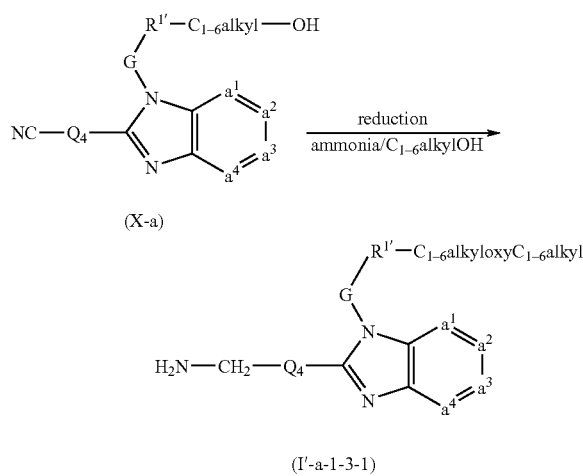

Compounds of formula (I'), wherein Q comprises a —$CH_2$—CHOH—$CH_2$—$NH_2$ moiety, said Q being represented by $H_2N$—$CH_2$—CHOH—$CH_2$—$Q_{4'}$, and said compounds being represented by formula (I'-a-1-3-2), can be prepared by reacting an intermediate of formula (XI) with ammonia in the presence of a suitable reaction-inert solvent, such as an alcohol, e.g. methanol.

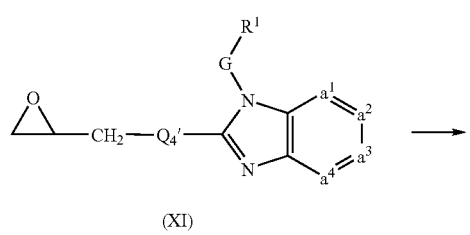

(XI)

-continued

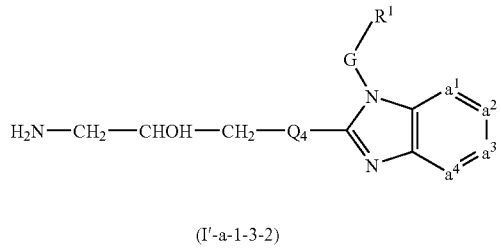

(I'-a-1-3-2)

Compounds of formula (I'), wherein, in the definition of Q, $R^2$ or one $R^6$ substituent is formyl, said Q being represented by H—C(=O)-$Q_1$, and said compounds being represented by formula (I'-b), can be prepared by reacting an intermediate of formula (XII) with formic acid, formamide and ammonia.

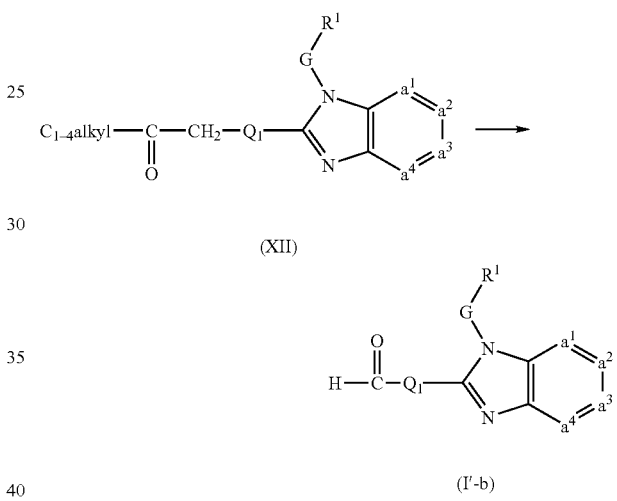

Compounds of formula (I'), wherein, in the definition of Q, $R^2$ is other than hydrogen, said $R^2$ being represented by $R^{2a}$, $R^4$ is hydrogen, and the carbon atom adjacent to the nitrogen atom carrying the $R^2$ and $R^4$ substituents, carries also at least one hydrogen atom, said Q being represented by $R^{2a}$—NH—$HQ_5$, and said compounds being represented by formula (I'-c), can be prepared by reductive amination of an intermediate of formula (XIII) with an intermediate of formula (XIV) in the presence of a suitable reducing agent, such as hydrogen, and a suitable catalyst, such as palladium-on-charcoal, platinum-on-charcoal, and the like. A suitable reaction-inert solvent for the above reaction is, for example, an alcohol, e.g. methanol, ethanol, 2-propanol and the like.

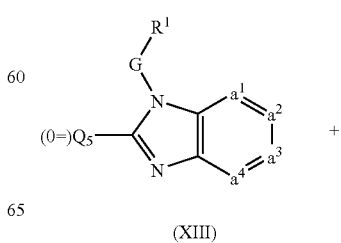

(XIII)

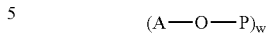

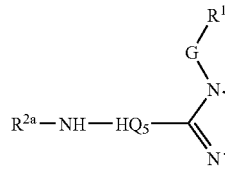

(XIV)

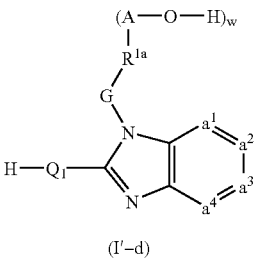

(XVI)

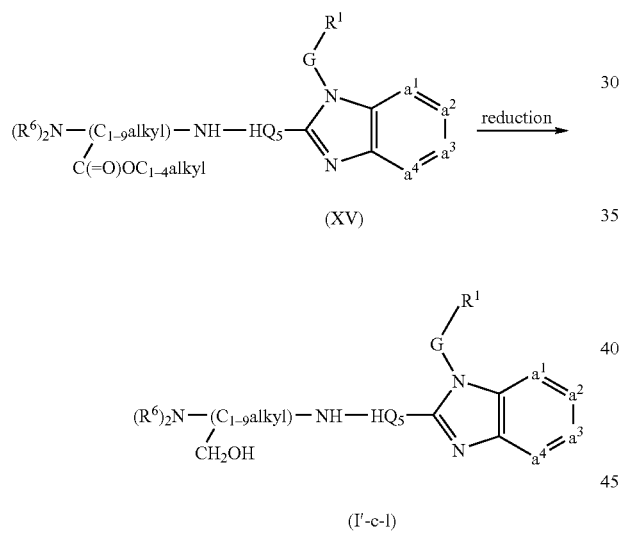

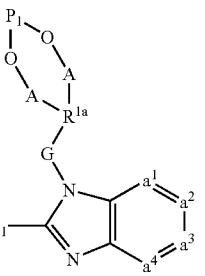

(I'-d)

Compounds of formula (I'-c), wherein $R^{2a}$ represents $C_{1-10}$alkyl substituted with $N(R^6)_2$ and with hydroxy, and the carbon atom carrying the hydroxy, carries also two hydrogen atoms, said $R^{2a}$ being represented by $[(C_{1-9}alkyl)CH_2OH]$—$N(R^6)_2$, and said compounds being represented by formula (I'-c-1), can be prepared by reducing an intermediate of formula (XV) in the presence of a suitable reducing agent, such as lithium aluminium hydride, in a suitable reaction-inert solvent, such as tetrahydrofuran.

Compounds of formula (I') wherein, in the definition of Q, $R^2$ or one $R^6$ substituent is hydrogen, said Q being represented by H-$Q_1$, and wherein $R^1$ is a monocyclic heterocycle substituted with 1 or more substituents selected from hydroxy, hydroxy$C_{1-6}$alkyl, or HO(—CH$_2$—CH$_2$—O)$_n$—, said substituents being represented by formula A-OH, said $R^1$ being represented by $R^{1a}$-(A-OH)$_w$, with w being the amount of substituents on $R^{1a}$ ranging from 1 to 4, and said compounds being represented by formula (I'-d), can be prepared by deprotecting an intermediate of formula (XVI) with a suitable acid, such as hydrochloric acid and the like, optionally in the presence of a suitable solvent, such as an alcohol. Suitable alcohols are methanol, ethanol, 2-propanol and the like.

Alternatively, one protecting group may also protect more than one substituent of $R^{1a}$, said protecting group being represented by $P_1$, as represented by formula (XVI-a). The two ways of protecting the substituents of $R^{1a}$, i.e. with a separate, as in formula (XVI), or a combined, as in formula (XVI-a), protecting group, may also be combined in the same intermediate, as represented by formula (XVI-b).

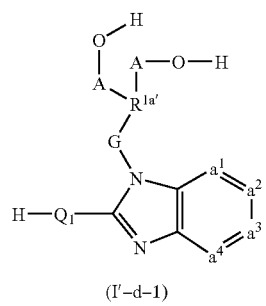

(XVI-a)

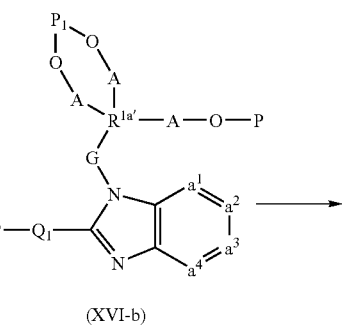

(XVI-b)

-continued

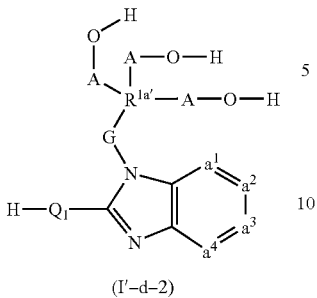

(I'-d-2)

Compounds of formula (I'), wherein Q is a radical of formula (b-2), said compounds being represented by formula (I'-e), can be prepared by reacting an intermediate of formula (XVII) with an intermediate of formula (XVIII) in the presence of sodium cyanide and a suitable reaction-inert solvent, such as an alcohol, e.g. methanol and the like.

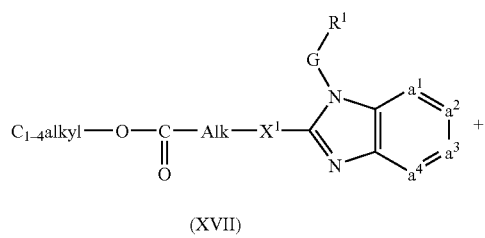

(XVII)

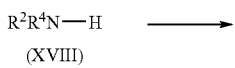

(XVIII)

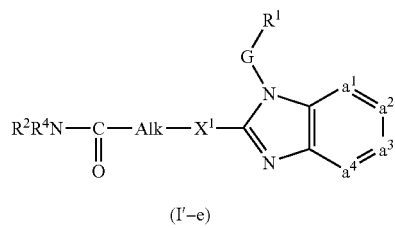

(I'-e)

Compounds of formula (I'), wherein in the definition of Q, $X^2$ is $C_{2-4}$alkyl-$NR^4$, said Q being represented by $Q_6N$—$CH_2$—$C_{1-3}$alkyl-$NR^4$, and said compounds being represented by formula (I'-p), can be prepared by reacting an intermediate of formula (XIX) with an intermediate of formula (XX) in the presence of isopropyl titanate (IV) and a suitable reducing agent, such as $NaBH_3CN$, and in the presence of a suitable reaction-inert solvent, such as methylene chloride or an alcohol, e.g. ethanol.

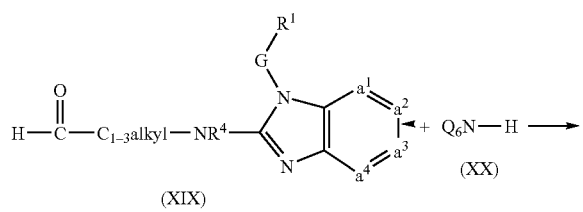

-continued

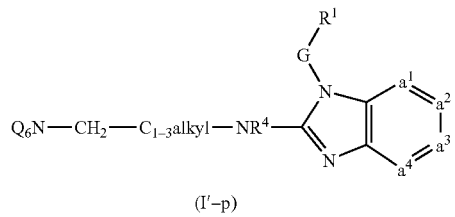

(I'-p)

ompounds of formula (I') may be converted into each other following art-known functional group transformation reactions, comprising those described hereinafter.

The compounds of formula (I') may be converted to the corresponding N-oxide forms following art-known procedures for converting a trivalent nitrogen into its N-oxide form. Said N-oxidation reaction may generally be carried out by reacting the starting material of formula (I') with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I'), wherein $R^1$ is monocyclic heterocycle substituted with $C_{1-6}$alkyloxycarbonyl, said $R^1$ being represented by $R^{1'}$—C(=O)O$C_{1-6}$alkyl, and said compounds being represented by formula (I'-f), can be prepared by esterification of a compound of formula (I'-g) in the presence of a suitable alcohol, e.g. methanol, ethanol, propanol, butanol, pentanol, hexanol and the like, and in the presence of a suitable acid, such as hydrochloric acid and the like.

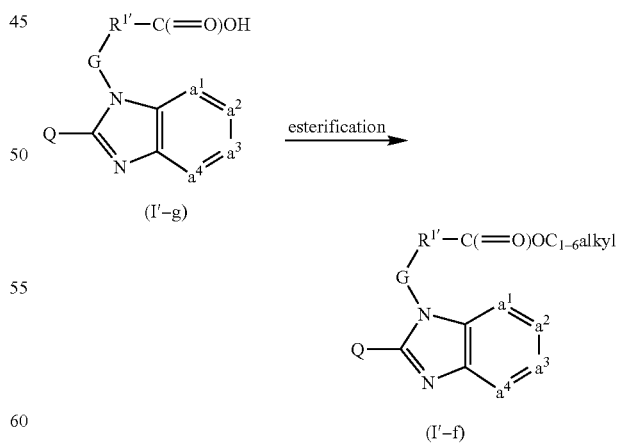

Compounds of formula (I'-a) may be converted into compounds of formula (I'), wherein, in the definition of Q, $R^2$ or at least one $R^6$ substituent is other than hydrogen, said $R^2$ or $R^6$ being represented by $Z_1$, said Q being represented by $Z_1$-$Q_1$, and said compounds being represented by formula (I'-h), by reaction with a reagent of formula (XXI), wherein $W_2$ is a suitable leaving group, such as a halo atom, e.g. bromo, or 4-methylbenzenesulphonate, in the presence of a suitable base, such as, for example disodium carbonate, dipotassium carbonate, sodium hydroxide and the like, in a reaction-inert solvent, e.g. 3-methyl-2-butanone, acetonitrile, N,N-dimethylformamide.

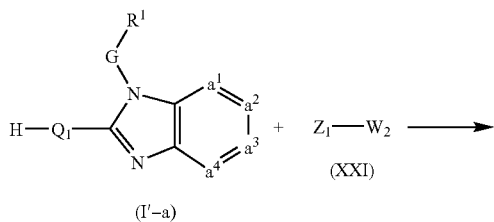

(I'-a)

(XXI)

Compounds of formula (I'-h), wherein in the definition of $Z_1$, $R^2$ is $CH_2$—$C_{1-9}$alkyl substituted with $N(R^6)_2$, said compounds being represented by formula (I'-h-1), can also be prepared by reacting a compound of formula (I'-a) wherein, in the definition of H-$Q_1$, $R^2$ is hydrogen, said H-$Q_1$ being represented by H-$Q_{1b}$, and said compounds being represented by formula (I'-a-3), with an intermediate of formula (XXII), in the presence of a suitable reducing agent, such as sodium cyanoborohydride, in a suitable reaction-inert solvent, such as an alcohol.

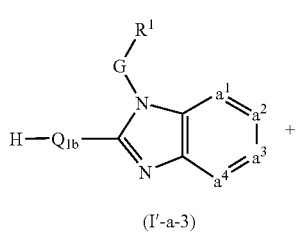

(I'-a-3)

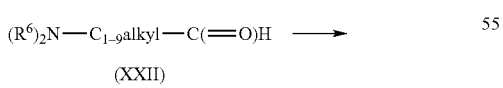

(XXII)

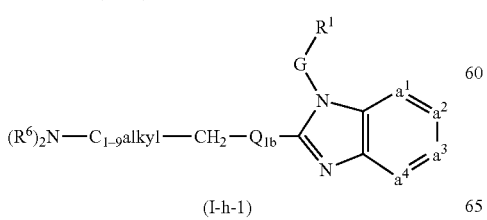

(I-h-1)

Compounds of formula (I'-h), wherein $Z_1$ comprises formyl, $C_{1-6}$alkylcarbonyl, or $C_{1-6}$alkyloxycarbonyl, said $Z_1$ being represented by $Z_{1a}$, and said compounds being represented by formula (I'-h-2), can be converted into compounds of formula (I'-a), by acidic hydrolysis in the presence of a suitable acid, such as hydrobromic, hydrochloric, sulfuric, acetic, or trifluoroacetic acid or a mixture of said acids, or by alkaline hydrolysis in the presence of a suitable base, such as, for example potassium hydroxide, in a suitable solvent such as water, alcohol, a mixture of water-alcohol, methylene chloride. Suitable alcohols are methanol, ethanol, 2-propanol, 1-butanol, sec. butanol and the like. In order to enhance the rate of the reaction, it is advantageous to work at elevated temperatures.

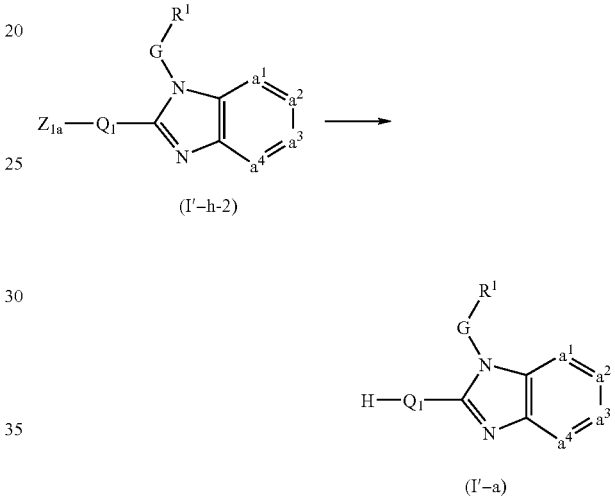

Compounds of formula (I'-b) can be prepared by reacting a compound of formula (I'-a) with formic acid.

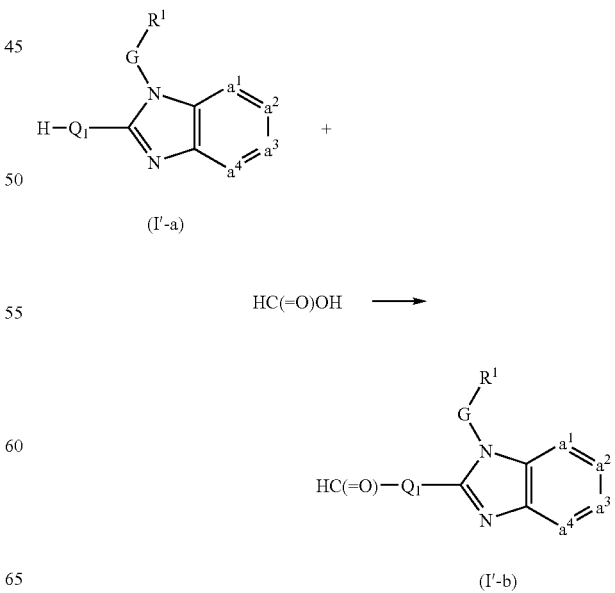

Compounds of formula (I') wherein $R^1$ is monocyclic heterocycle substituted with hydroxy, said $R^1$ being represented by HO—$R^{1'}$, and said compounds being represented by formula (I'-i), can be prepared by deprotecting a compound of formula (I'-j), wherein $R^1$ is monocyclic heterocycle substituted with $C_{1-6}$alkyloxy or aryl$C_{1-6}$alkyloxy, said $C_{1-6}$alkyl or aryl$C_{1-6}$alkyl being represented by $Z_2$, and said $R^1$ being represented by $Z_2$-O—$R^{1'}$. Said deprotection can be performed in a reaction-inert solvent, such as, for example methylene chloride, in the presence of a suitable deprotecting agent, e.g. tribromoborane.

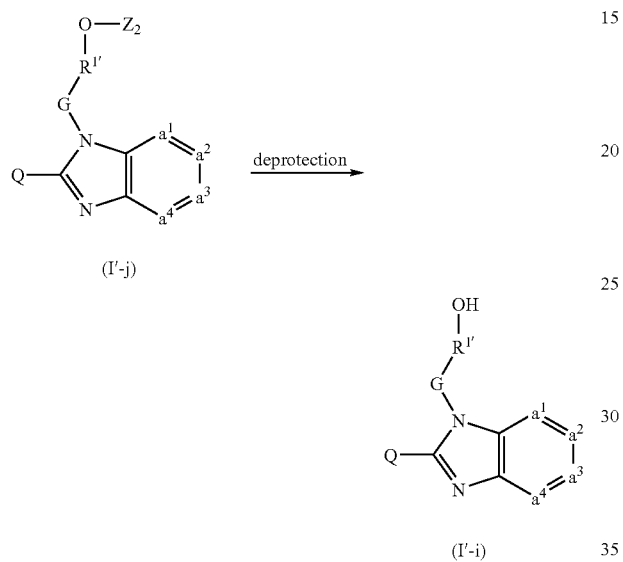

Compounds of formula (I') wherein $R^1$ is monocyclic heterocycle substituted with halo(—$CH_2$—$CH_2$—O)$_n$, said compounds being represented by formula (I'-k), can be converted into a compound of formula (I'-1-1) or (I'-1-2) by reaction with the appropriate amine of formula (XXIII) or (XXV) in a suitable reaction-inert solvent, e.g. tetrahydrofuran.

Compounds of formula (I'), wherein $R^1$ is monocyclic heterocycle substituted with halo, said compounds being represented by formula (I'-m) can be converted into compounds of formula (I') by reaction with 1-butanethiol in the presence of palladium-on-charcoal and CaO in a suitable reaction-inert solvent, such as tetrahydrofuran.

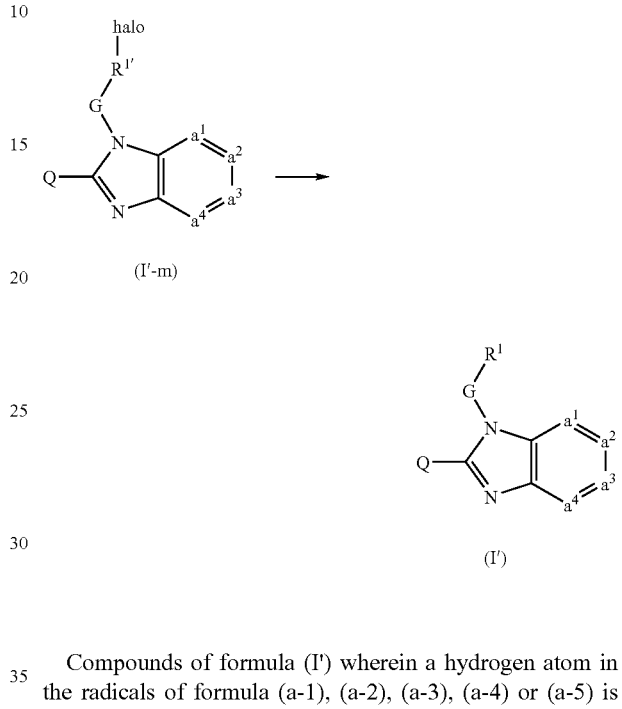

Compounds of formula (I') wherein a hydrogen atom in the radicals of formula (a-1), (a-2), (a-3), (a-4) or (a-5) is replaced by nitro, said compounds being represented by formula (I'-n) may be reduced to a compound of formula (I'-o) in the presence of a suitable reducing agent, such as hydrogen, in the presence of a suitable catalyst, such as platinum-on-charcoal, and optionally in the presence of a suitable catalyst poison, e.g. a thiophene solution. The reaction may be performed in a suitable reaction-inert solvent, such as an alcohol.

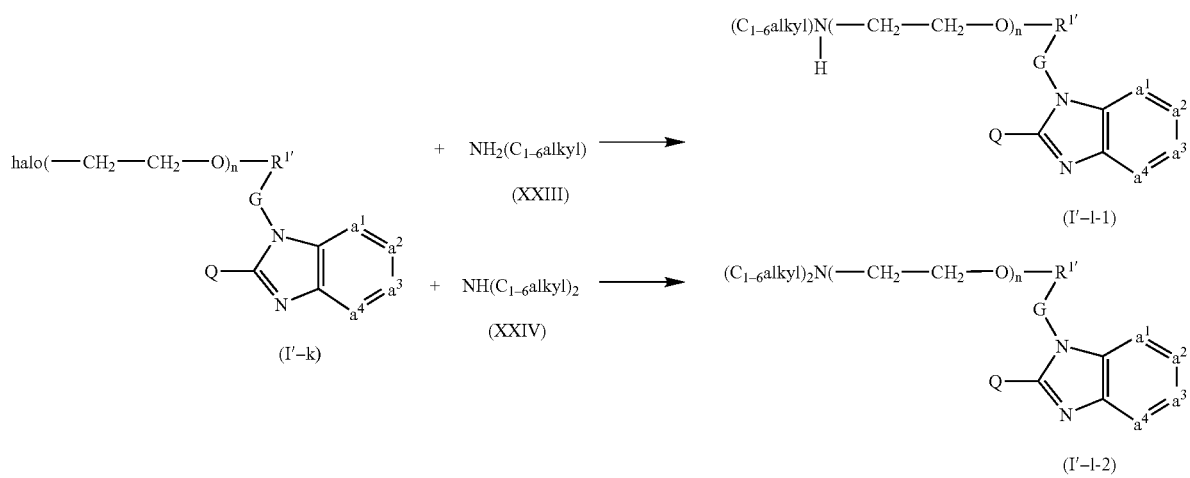

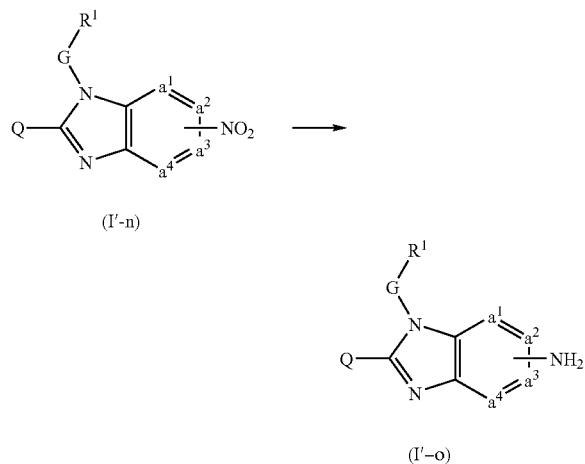

(I'-n)

(I'-o)

The reactions described hereinabove for the preparation of the compounds of formula (I') can also be used to prepare the compounds of the group (I").

In the following paragraphs, there are described several methods of preparing the intermediates in the foregoing preparations. A number of intermediates and starting materials are commercially available or are known compounds which may be prepared according to conventional reaction procedures generally known in the art or analogous to the procedures described in EP-A-0,005,318, EP-A-0,099,139, EP-A-0,151,824, EP-A-0,151,826, EP-A-0,231,937, EP-A-0,295,742, EP-A-0,297,661, EP-A-0,539,420, EP-A-0,539,421, U.S. Pat. No. 4,634,704, U.S. Pat. No. 4,695,569.

In the foregoing and the following preparations, the reaction mixture is worked up following art-known methods and the reaction product is isolated and, if necessary, further purified.

Intermediates of formula (III) can be prepared by reacting an intermediate of formula (XXV) with a suitable leaving group, i.e. $W_1$, introducing agent, e.g. 1-halo-2,5-pyrrolidinedione, in the presence of dibenzoyl peroxide, in a reaction-inert solvent, e.g. tetrachloromethane.

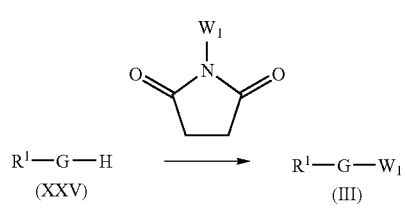

$R^1$—G—H    $R^1$—G—$W_1$
(XXV)         (III)

Intermediates of formula (XXV), wherein $R^1$ is monocyclic heterocycle substituted with chloro, said $R^1$ being represented by Cl—$R^{1'}$ and said intermediates being represented by formula (XXV-a), can be prepared by reacting an intermediate of formula (XXVI), wherein (O=)$R^{1b}H$ is defined as a carbonyl derivative of $R^{1'}$ wherein one carbon or nitrogen, adjacent to the carbonyl, carries at least one hydrogen, with phosphorus oxychloride. Intermediates of formula (XXVI) may also react as their enol tautomeric forms.

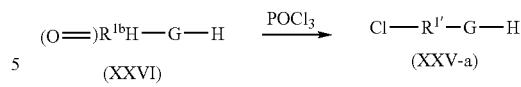

(O=)$R^{1b}H$—G—H   $\xrightarrow{POCl_3}$   Cl—$R^{1'}$—G—H
(XXVI)                                      (XXV-a)

Intermediates of formula (III) wherein $W_1$ is chloro, which is attached to a carbon atom carrying at least one hydrogen, said G being represented by $G_1H$, and said intermediates being represented by formula (III-a), can also be prepared by reacting an intermediate of formula (XXVII) with thionylchloride in a reaction-inert solvent, e.g. methylene chloride.

$R^1$—$G_1H$—OH   $\xrightarrow{SOCl_2}$   $R^1$—$G_1H$—Cl
(XXVII)                                   (III-a)

Intermediates of formula (XXVII) can be prepared by reducing an intermediate of formula (XXVIII) in a reaction-inert solvent, e.g. an alcohol, in the presence of a suitable reducing agent, e.g. sodium borohydride.

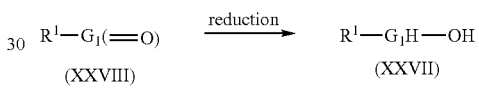

$R^1$—$G_1$(=O)   $\xrightarrow{reduction}$   $R^1$—$G_1H$—OH
(XXVIII)                                     (XXVII)

Alternatively, intermediates of formula (XXVII) can also be prepared by deprotecting an intermediate of formula (XXIX), wherein P is a suitable protecting group, e.g. $C_{1-4}$alkylcarbonyl, in a reaction-inert solvent, such as an alcohol, in the presence of a suitable base, e.g. sodium hydroxide.

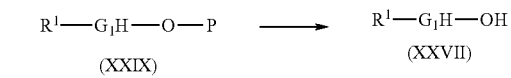

$R^1$—$G_1H$—O—P   →   $R^1$—$G_1H$—OH
(XXIX)                  (XXVII)

Intermediates of formula (XXVIII), wherein $G_1$(=O) is CH(=O), said intermediates being represented by formula (XXVIII-a), can be prepared by reacting an intermediate of formula (XXX), wherein $W_3$ is a suitable leaving group, such as a halo atom, e.g. bromo, with N,N-dimethylformamide in the presence of butyllithium in a reaction-inert solvent, e.g. tetrahydrofuran, diethylether or a mixture thereof.

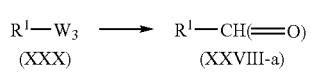

$R^1$—$W_3$   →   $R^1$—CH(=O)
(XXX)              (XXVIII-a)

Intermediates of formula (IV) can be prepared by reacting an intermediate of formula (XXXI-a) or (XXXI-b), wherein P represents a suitable protecting group, such as, for example, $C_{1-4}$alkyloxycarbonyl, with an intermediate of formula (III) according to the reaction described for the general preparation of compounds of formula (I').

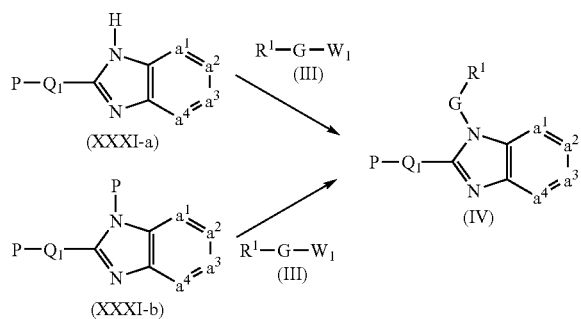

Intermediates of formula (IV) can also be prepared by reacting an intermediate of formula (XXXI-a) with an intermediate of formula (XXXII) that has reacted with methanesulfonyl chloride, in the presence of a suitable base, such as sodium hydride, and in the presence of a suitable reaction-inert solvent, e.g. N,N-dimethylformamide.

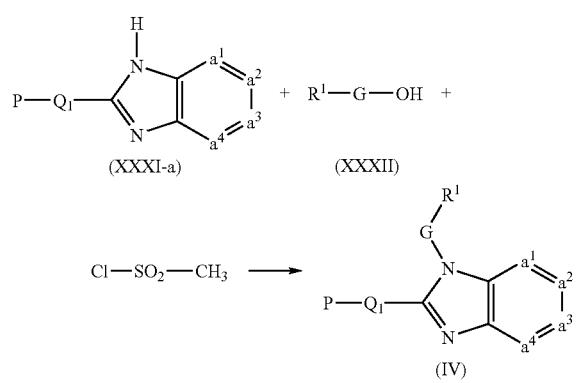

Intermediates of formula (IV) can also be prepared by a cyclization reaction of an intermediate of formula (XXXIII) in a reaction-inert solvent, e.g. an alcohol or N,N-dimethylformamide, in the presence of mercury oxide and sulphur.

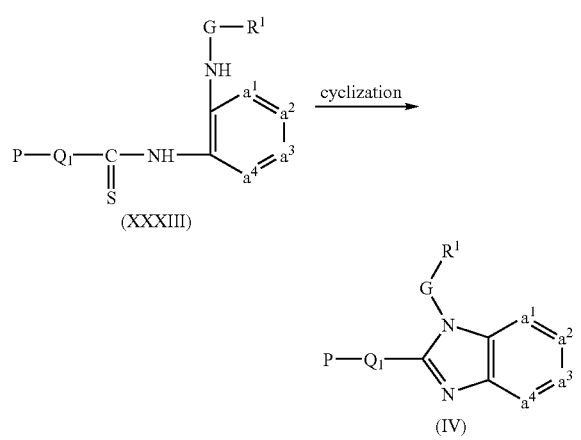

Intermediates of formula (IV) wherein $Q_1$ comprises an unsaturated bond, said $Q_1$ being represented by $Q_{1a}$(CH=CH), and said intermediates by formula (IV-a), can be prepared by reacting an intermediate of formula (XXXIV) with an intermediate of formula (III) in the presence of a suitable base, such as dipotassium carbonate.

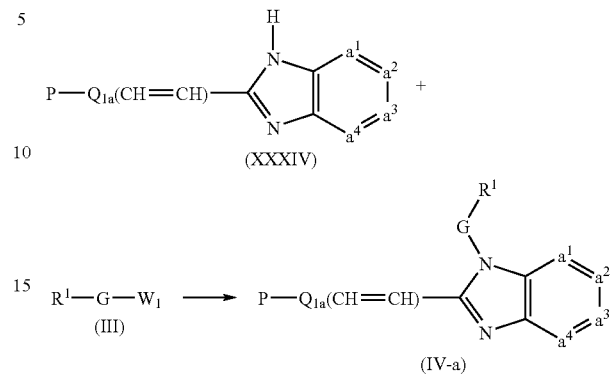

Intermediates of formula (IV) wherein, in the definition of $Q_1$, the $X^1$ or $X^2$ moieties in the radicals of formula (b-1) to (b-8) represent NH, said Q, being represented by $Q_{1c}$-NH, and said intermediates by formula (IV-b), may also be prepared by reacting an intermediate of formula (XXXV) with an intermediate of formula (XXXVI).

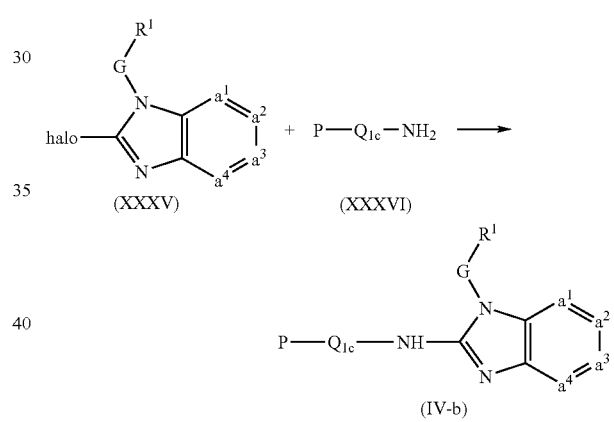

Intermediates of formula (IV) wherein $R^1$ is monocyclic heterocycle substituted with amino or mono- or di($C_{1-6}$ alkyl)amino, said $R^1$ being represented by $R^{5a}R^{5b}N-R^{1'}$, wherein $R^{5a}$ and $R^{5b}$ are defined as described hereinabove, and said intermediates being represented by formula (IV-c), can be prepared by reacting an intermediate of formula (XXXVII) with an appropriate amine, represented by formula (XXXVIII), in the presence of an appropriate catalyst, e.g. palladium, and (R)-(+)-2,2'-bis(diphenyl-phosphino)-1,1'-binaphtyl, in a suitable reaction-inert solvent, e.g. tetrahydrofuran.

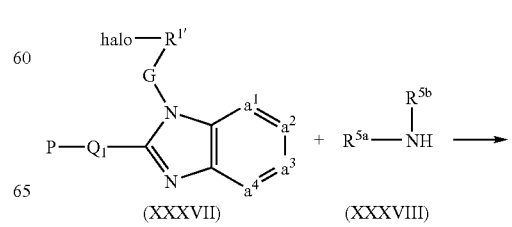

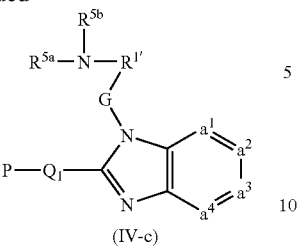

(IV-c)

Intermediates of formula (IV) wherein $R^1$ is monocyclic heterocycle substituted with $C(=O)-NR^{5a}R^{5b}$, wherein $R^{5a}$ and $R^{5b}$ are defined as described hereinabove, said $R^1$ being represented by $R^{5a}R^{5b}N-C(=O)-R^{1'}$, and said intermediates being represented by formula (IV-d), can be prepared by reacting an intermediate of formula (XXXVII) with an appropriate amine, represented by formula (XXX-VII), under an atmosphere of carbon monoxide, in the presence of a suitable catalyst, e.g. palladium (II) acetate, and 1,3-bis(diphenylphosphino)propane, in a suitable reaction-inert solvent, e.g. tetrahydrofuran.

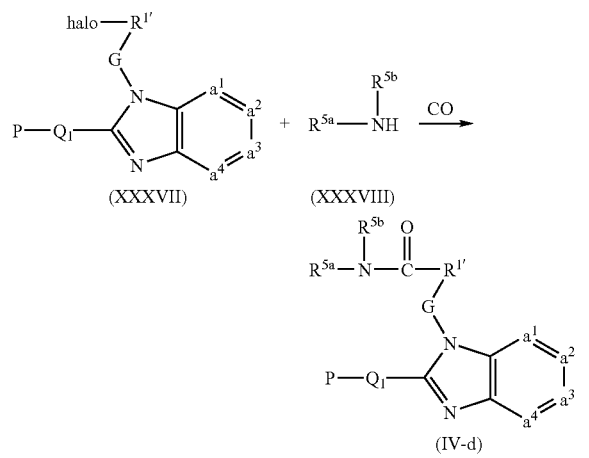

Intermediates of formula (IV) wherein P-$Q_1$ comprises $C_{1-10}$alkyl or $C_{3-7}$cycloalkyl substituted with $NR^6$—P, said $C_{1-10}$alkyl or $C_{3-7}$cycloalkyl being represented by $Z_3$, said P-$Q_1$ being represented by P—N $R^6$-$Z_3$-$Q_{1b}$, and said intermediates being represented by formula (IV-e), can be prepared by reacting a compound of formula (I'-a-3) with an intermediate of formula (XXXIX), wherein $W_4$ represents a suitable leaving group, such as p-toluenesulphonate. Said reaction can be performed in a reaction-inert solvent, e.g. acetonitrile, in the presence of a suitable base, e.g. dipotassium carbonate.

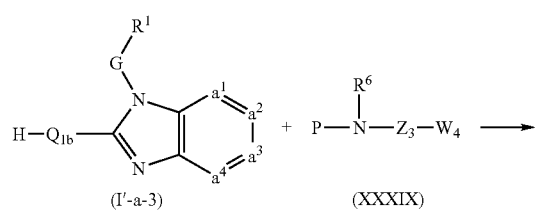

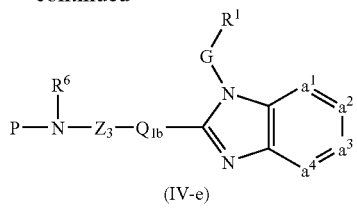

Intermediates of formula (IV-e), wherein $R^6$ is hydroxy$C_{1-6}$alkyl, said intermediates being represented by formula (IV-e-1), can be prepared by reacting an intermediate of formula (XL) with an intermediate of formula (XLI) in the presence of a suitable base, e.g. dipotassium carbonate, and a suitable solvent, e.g. acetonitrile.

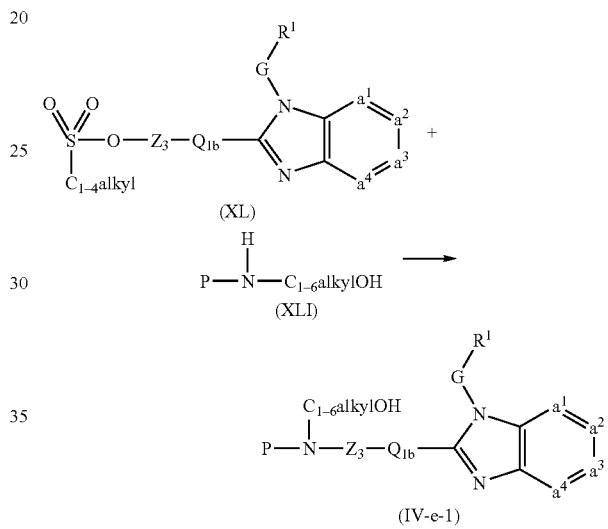

Intermediates of formula (XXX-a) or (XXXI-b) can be prepared by protecting an intermediate of formula (XLII) with a suitable protecting group, such as, for example, $C_{1-4}$alkyloxycarbonyl, in a reaction-inert solvent, such as methylene chloride or an alcohol, e.g. methanol, ethanol, 2-propanol and the like, in the presence of a suitable reagent, e.g. di$C_{1-4}$alkyldicarbonate, and optionally in the presence of a suitable base, e.g. sodium acetate.

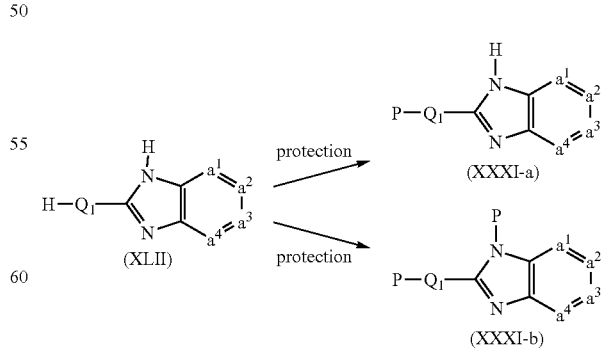

Alternatively, intermediates of formula (XXXI-a) or (XXXI-b) can be converted into an intermediate of formula (XLII) by reaction with a suitable acid, such as hydrochloric acid or hydrobromic acid and the like or mixtures thereof, in the presence of a suitable solvent, e.g. water.

Intermediates of formula (XXXI-a) or (XXXI-b), wherein in the definition of $Q_1$, the $X^1$ or $X^2$ moieties in the radicals of formula (b-1) to (b-8) represent NH, said $Q_1$ being represented by $Q_{1c}$-NH, and said intermediates by formula (XXXI-a-1) or (XXXI-b-1), can be prepared by reacting an intermediate of formula (XLIII-a) or (XLIII-b), wherein $W_5$ represents a suitable leaving group, such as for example a halo atom, e.g. chloro, with an intermediate of formula (XLIV).

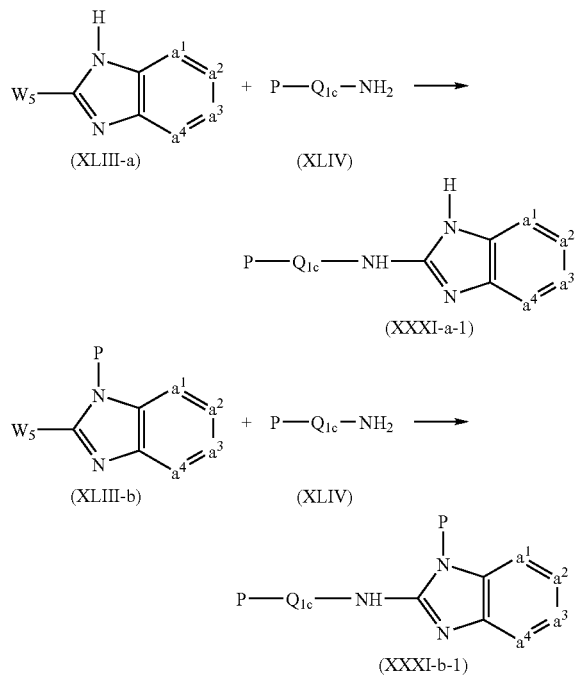

Intermediates of formula (XLIII-a) or (XLIII-b) can be prepared by reacting an intermediate of formula (XLV-a) or (XLV-b) with $H_2P(=O)(W_5)_3$ in the presence of a suitable acid, e.g. hydrochloric acid.

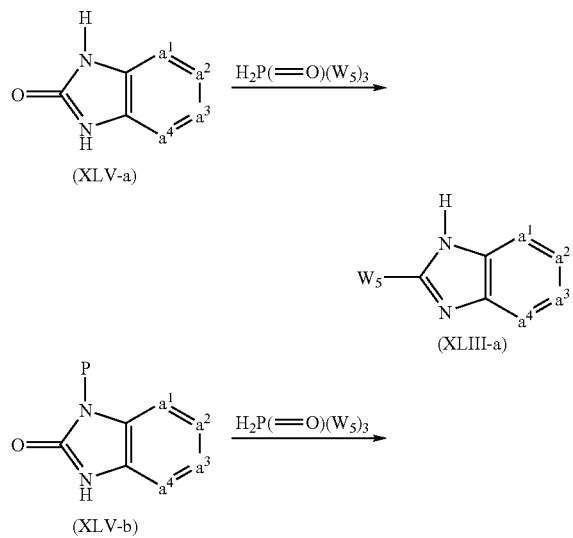

-continued

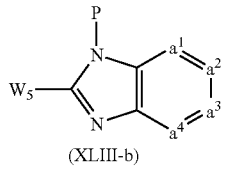

Intermediates of formula (XLV-a) or (XLV-b) can be prepared by reacting an intermediate of formula (XLVI-a) or (XLVI-b) with an intermediate of formula (XLVII).

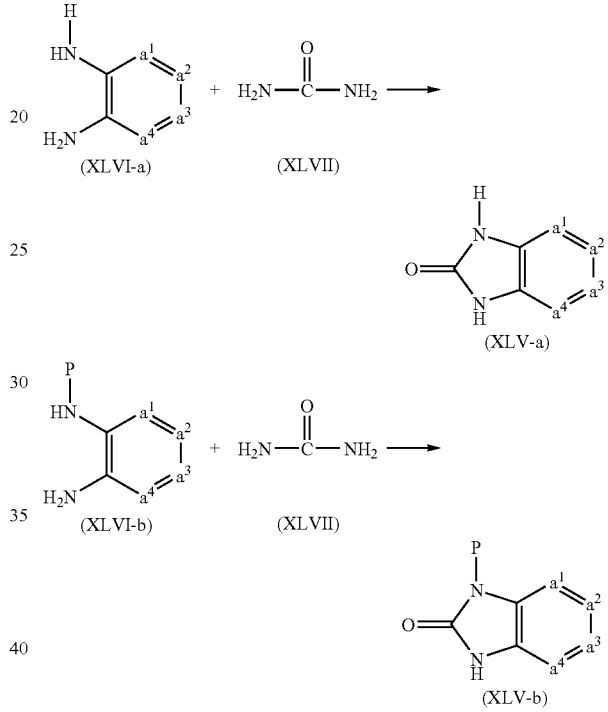

Intermediates of formula (XXXI-a) can also be prepared by reacting an intermediate of formula (XLVI-a) with P-$Q_1$-C(=NH)—O—$CH_2$—$CH_3$ in a reaction-inert solvent, such as an alcohol.

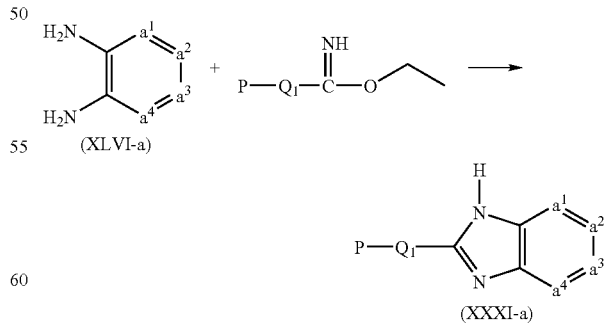

Intermediates of formula (XXXIII) can be prepared by reacting an intermediate of formula (XLVIII) with an intermediate of formula P-$Q_1$=C=S, which is synthesized according to the procedures described in EP 0005318, in a reaction-inert solvent, such as an alcohol, e.g. ethanol. To increase the reaction rate, the reaction may be performed at elevated temperatures.

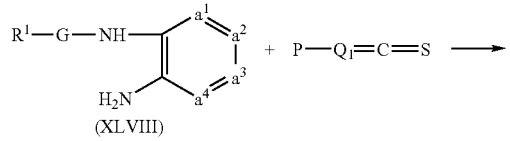
(XLVIII)

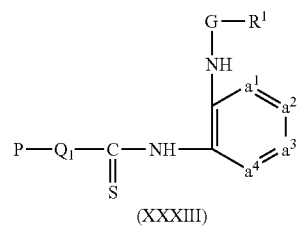
(XXXIII)

Intermediates of formula (XLVIII) can be obtained by reducing an intermediate of formula (IL) in a reaction-inert solvent, e.g. an alcohol, in the presence of a suitable reducing agent, e.g. hydrogen, and an appropriate catalyst, e.g. Raney Nickel.

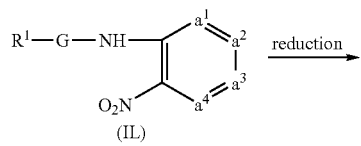
(IL)

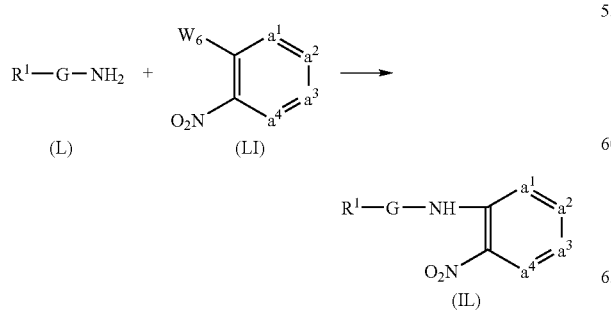
(XLVIII)

Intermediates of formula (IL) can be prepared by reacting an intermediate of formula (L) with an intermediate of formula (LI), in which $W_6$ represents a suitable leaving group, such as a halo atom, e.g. chloro. The reaction may be performed in a reaction-inert solvent, e.g. acetonitrile, in the presence of a suitable base, e.g. dipotassium carbonate.

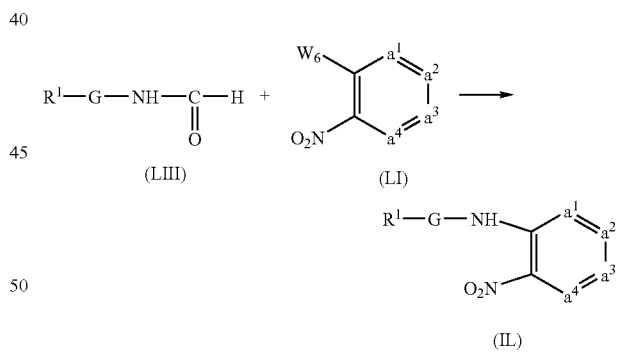
(IL)

Intermediates of formula (L) can be prepared by reacting an intermediate of formula (LII) with a suitable acid, such as hydrochloric acid, in the presence of a suitable solvent, e.g. an alcohol, e.g. ethanol.

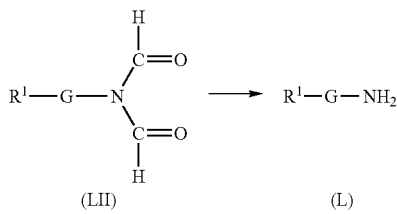
(LII) (L)

Intermediates of formula (LII) can be prepared by reacting an intermediate of formula (III) with $NaN[C(=O)H]_2$.

(III)

(LII)

Intermediates of formula (IL) can also be prepared by reacting an intermediate of formula (LI) with an intermediate of formula (LIII) (J. Org. Chem., 25, p 1138, 1960) in a reaction-inert solvent, e.g. N,N-dimethylformamide, in the presence of an appropriate base, e.g. sodium hydride.

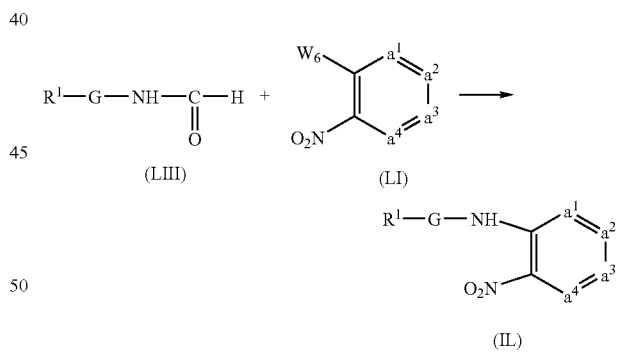
(LIII) (LI)

(IL)

Intermediates of formula (XXXIV) can be prepared by dehydrating an intermediate of formula (LIV) with a suitable acid, such as sulfuric acid.

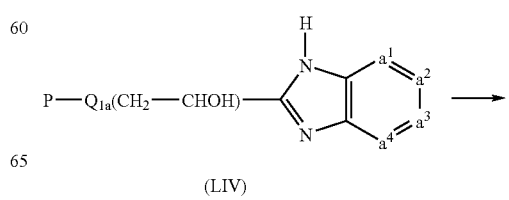
(LIV)

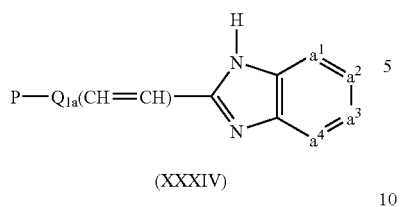

(XXXIV)

Intermediates of formula (LIV) wherein, in the definition of $Q_{1a}$, the $X^1$ or $X^2$ moieties are $CH_2$, said $Q_{1a}$ being represented by $Q_{1a'}$, and said intermediates being represented by formula (LIV-a), can be prepared by reacting a carbonyl moiety of formula (LV) with an intermediate of formula (LVI) in the presence of N,N-diisopropylamine and butyl lithium, in a suitable reaction-inert solvent, e.g. tetrahydrofuran.

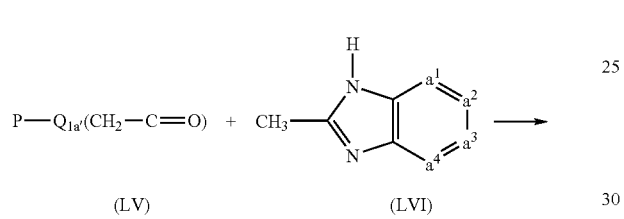

(LV)    (LVI)

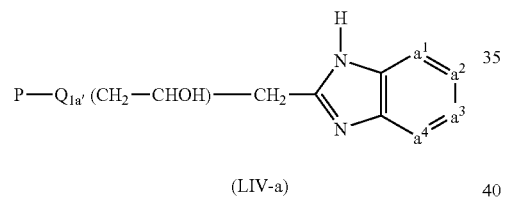

(LIV-a)

Intermediates of formula (V) can be prepared by reacting an intermediate of formula (LVII) with 1H-isoindole-1,3 (2H)-dione in the presence of triphenylphosphine and diethyl azodicarboxylate.

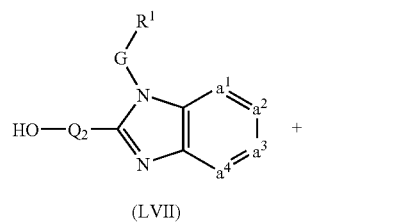

(LVII)

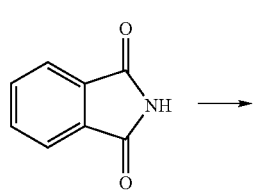

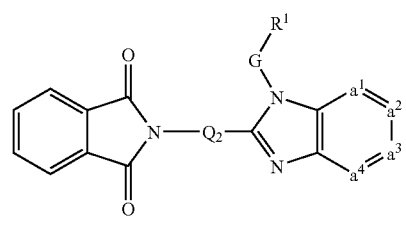

(V)

Intermediates of formula (V) may also be prepared by reacting an intermediate of formula (LVIII) with 1H-isoindole-1,3 (2H)-dione in the presence of a suitable base, such as sodium hydride, and a suitable solvent, such as N,N-dimethylformamide.

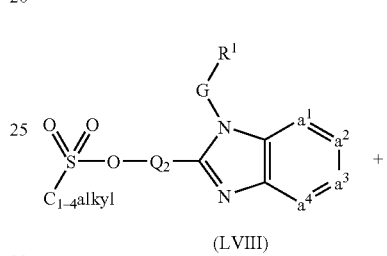

(LVIII)

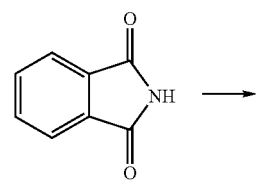

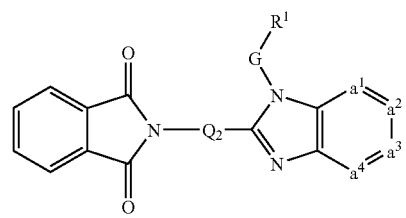

(V)

Intermediates of formula (LVIII) can be prepared by reacting an intermediate of formula (LVII) with an intermediate of formula (LIX), wherein $W_7$ represents a suitable leaving group, such as a halo atom, e.g. chloro, in the presence of a suitable base, such as N,N-diethyl-ethanamine, and a suitable solvent, such as methylene chloride.

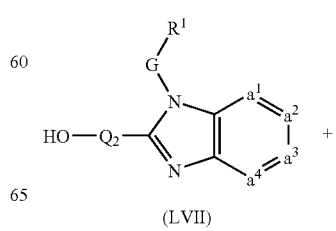

(LVII)

-continued

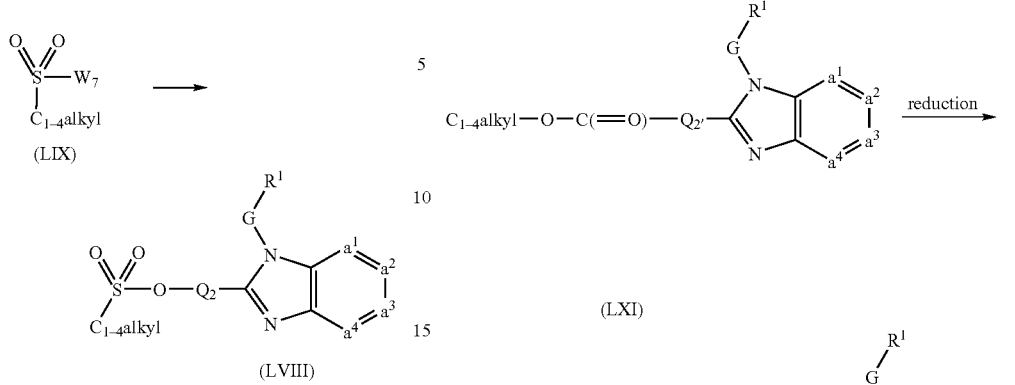

Intermediates of formula (V), wherein in the definition of $Q_2$, $R^2$ is $C_{1-10}$alkyl, said $Q_2$ being represented by $C_{1-10}$alkyl-$Q_{1b}$, and said intermediates by formula (V-a), can be prepared by reacting a compound of formula (I'-a-3) with an intermediate of formula (LX), wherein $W_8$ is a suitable leaving group, such as a halo atom, e.g. chloro, in the presence of a suitable base, such as dipotassium carbonate, and a suitable solvent, such as acetonitrile.

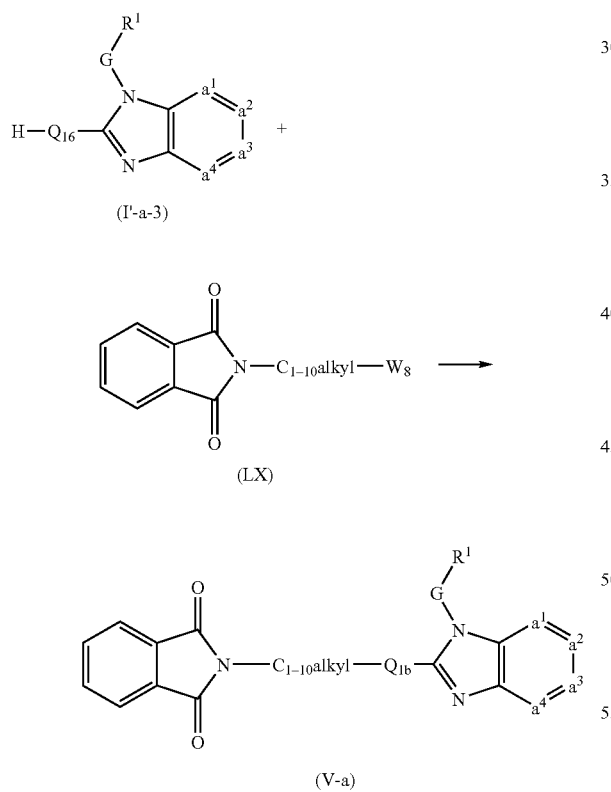

Intermediates of formula (LVII) wherein, in the definition of $Q_2$, the carbon atom carrying the hydroxy, also carries two hydrogen atoms, said HO-$Q_2$ being represented by HO—$CH_2$-$Q_{2'}$, and said intermediates being represented by formula (LVII-a), can be prepared by reducing an intermediate of formula (LXI) in the presence of a suitable reducing agent, such as lithium aluminium hydride, in a suitable reaction-inert solvent, e.g. tetrahydrofuran.

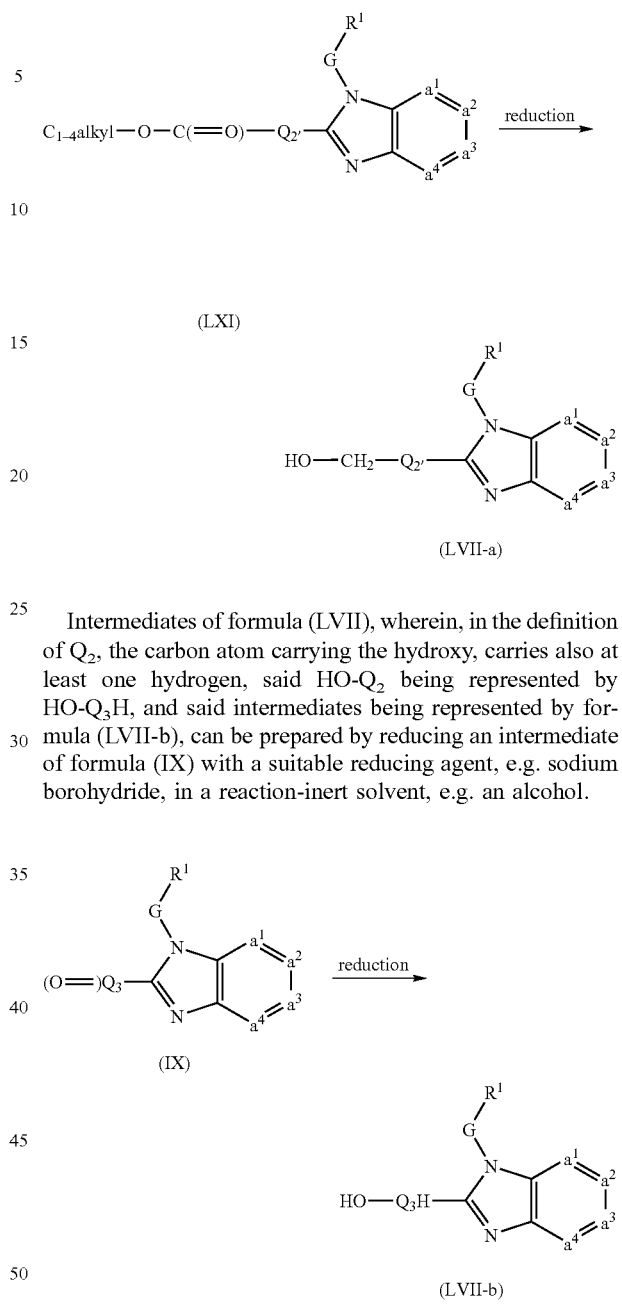

Intermediates of formula (LVII), wherein, in the definition of $Q_2$, the carbon atom carrying the hydroxy, carries also at least one hydrogen, said HO-$Q_2$ being represented by HO-$Q_3$H, and said intermediates being represented by formula (LVII-b), can be prepared by reducing an intermediate of formula (IX) with a suitable reducing agent, e.g. sodium borohydride, in a reaction-inert solvent, e.g. an alcohol.

Intermediates of formula (VI) wherein, in the definition of $Q_2$, $R^2$ is $C_{1-10}$alkyl substituted with $N(P)_2$ and the carbon atom adjacent to the nitrogen atom carrying the $R^2$ substituent carries also at least one hydrogen atom, said $Q_2$ being represented by $(P)_2$—N—$C_{1-10}$alkyl-NH-$Q_{2a}$H, and said intermediates being represented by formula (VI-a), can be prepared by reductive amination of an intermediate of formula (LXII) with an intermediate of formula (LXII) in the presence of a suitable reductive agent, such as hydrogen, and a suitable catalyst, such as palladium-on-charcoal, platinum-on-charcoal, and the like, and optionally in the presence of a suitable catalyst poison, such as a thiophene solution. A suitable solvent in this reaction is a reaction-inert solvent, such as an alcohol.

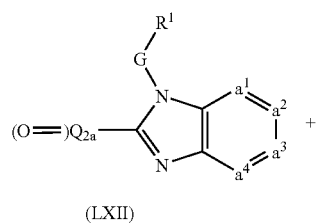

(LXII) +

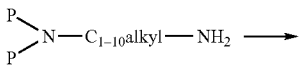

(LXIII)

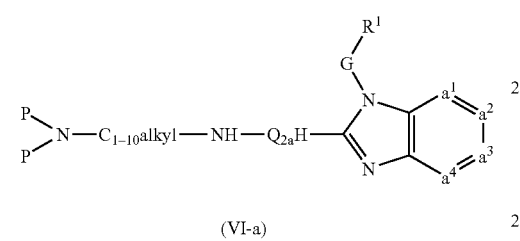

(VI-a)

Intermediates of formula (LXII) can be prepared by deprotecting an intermediate of formula (LXIV) in the presence of a suitable acid, such as hydrochloric acid and the like, in a suitable solvent, e.g. water.

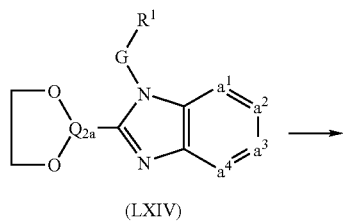

(LXIV)

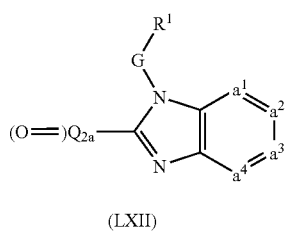

(LXII)

Intermediates of formula (IX) may be prepared by deprotecting an intermediate of formula (LXV) in the presence of a suitable acid, e.g. hydrochloric acid and the like.

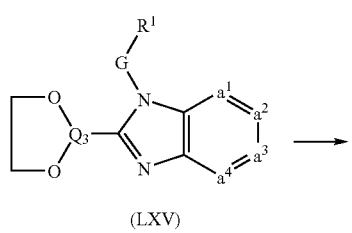

(LXV)

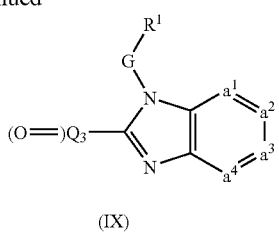

(IX)

Intermediates of formula (LXV) can be prepared by reacting an intermediate of formula (LXVI) with an intermediate of formula (III) in the presence of a suitable base, e.g. dipotassium carbonate, in a suitable reaction-inert solvent, e.g. acetonitrile.

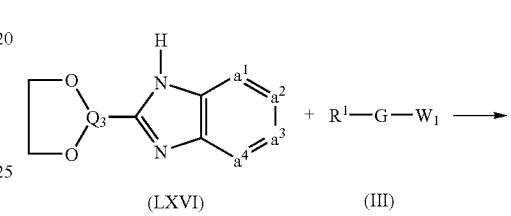

(LXVI)     (III)

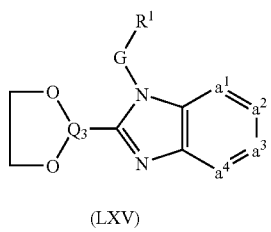

(LXV)

Intermediates of formula (LXVI) wherein, in the definition of $Q_3$, the $X^1$ or $X^2$ moiety of the radicals of formula (b-1) to (b-8) represent NH, said $Q_3$ being represented by $Q_{3'}$-NH, and said intermediates being represented by formula (LXVI-a), may be prepared by cyclizing an intermediate of formula (LXVII) in the presence of mercury oxide and sulphur, in a suitable reaction-inert solvent, e.g. an alcohol.

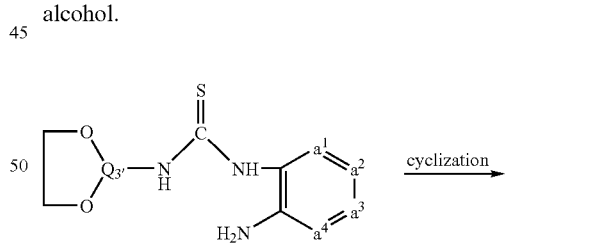

(LXVI)

(LXVI-a)

Intermediates of formula (LXVII) can be prepared by reducing an intermediate of formula (LXVIII) in the presence of a suitable reducing agent, such as hydrogen, in the presence of a suitable catalyst; such as palladium-on-charcoal, platinum-on-charcoal and the like, in a suitable solvent, e.g. a mixture of ammonia in alcohol. Suitable alcohols are methanol, ethanol, 2-propanol and the like.

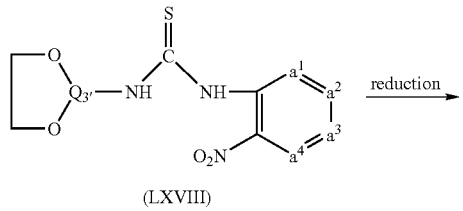

(LXVIII)

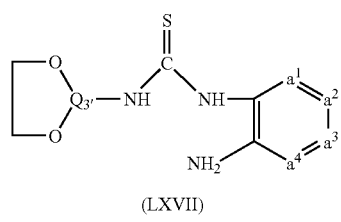

(LXVII)

Intermediates of formula (LXVIII) can be prepared by reacting an intermediate of formula (LXIX) with an intermediate of formula (LXX) in a suitable reaction-inert solvent, e.g. ethanol.

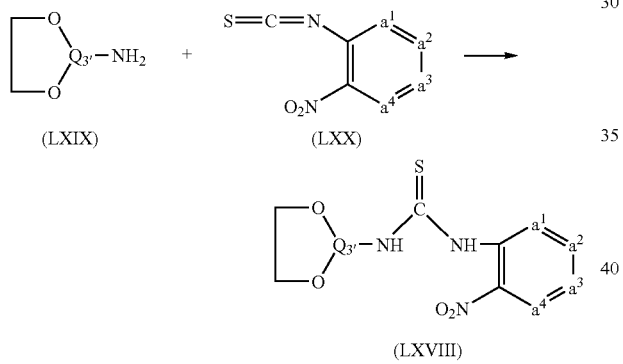

(LXVIII)

Intermediates of formula (IX), wherein, in the definition of $Q_3$, $R^2$ comprises $C_{1-10}$alkyl, said $Q_3$ being represented by $C_{1-10}$alkyl-$Q_{1b}$, and said intermediates being represented by formula (IX-a), can be prepared by reacting a compound of formula (I'-a-3) with a reagent of formula (LXXI), wherein (O=)$C_{1-10}$alkyl represents a carbonyl derivative of $C_{1-10}$alkyl and wherein $W_9$ is a suitable leaving group, such as a halo atom, e.g. bromo, in a reaction-inert solvent, e.g. acetonitrile, in the presence of a suitable base, e.g. dipotassium carbonate.

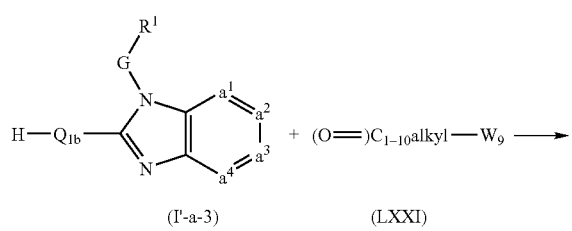

(I'-a-3)            (LXXI)

-continued

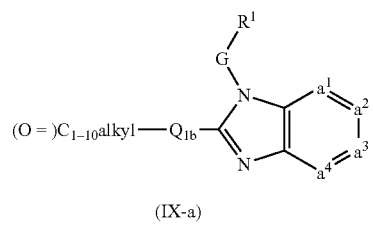

(IX-a)

Intermediates of formula (X) wherein $Q_4$ comprises $C_{1-9}$alkyl, said $Q_4$ being represented by $C_{1-9}$alkyl-$Q_{1b}$, and said intermediates being represented by formula (X-a), can be prepared by reacting a compound of formula (I'-a-3) with a reagent of formula (LXXII), wherein $W_{10}$ represents a suitable leaving group, such as a halo atom, e.g. chloro, in a reaction-inert solvent, e.g. 3-methyl-2-butanone, in the presence of a suitable base, e.g. dipotassium carbonate, sodium bicarbonate and the like.

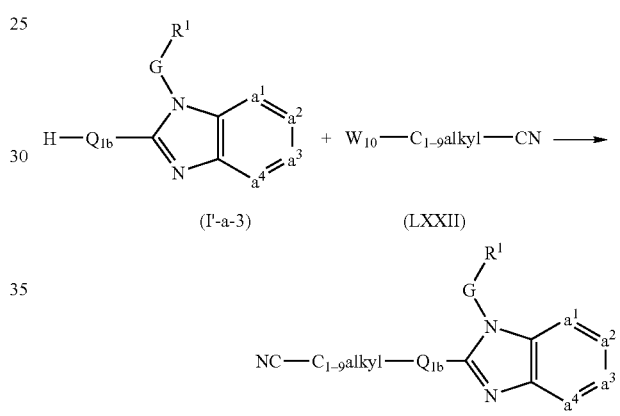

(I'-a-3)            (LXXII)

(X-a)

Intermediates of formula (X), wherein NC-$Q_4$ represents NC—($C_{1-9}$alkyl)($R^4$)N—C(=O)-Alk-$X^1$, said intermediates being represented by formula (X-b), can be prepared by reacting an intermediate of formula (LXXIII) with an intermediate of formula (LXXIV) in the presence of di-1H-imidazol-2-yl-methanone, a suitable base, such as N,N-diethyl-ethanamine, and a suitable solvent, such as methylene chloride.

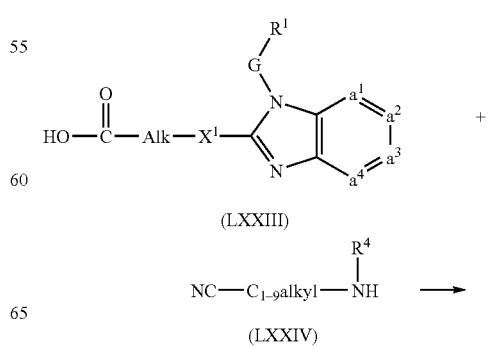

(LXXIII)

(LXXIV)

-continued

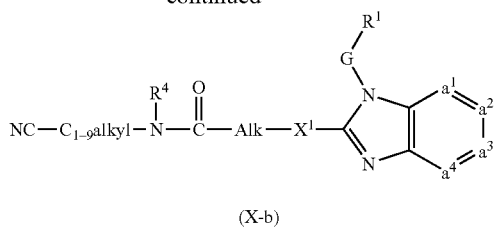

(X-b)

Intermediates of formula (XI), wherein $Q_{4'}$ represents $Q_{1b}$, said intermediates being represented by formula (XI-a), can be prepared by reacting a compound of formula (I'-a-3) with an intermediate of formula (LXXV), wherein $W_{11}$ represents a suitable leaving group, such as a halo atom, e.g. chloro, in the presence of a suitable base, such as disodium carbonate, and in the presence of a suitable solvent, such as 3-methyl-2-butanone.

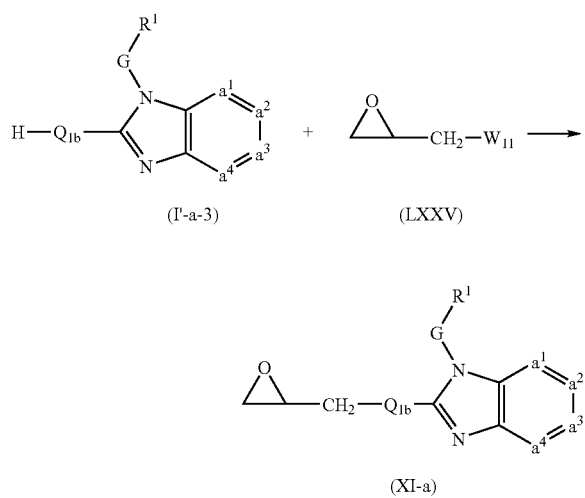

Intermediates of formula (XIX) can be prepared by reacting an intermediate of formula (LXXVI) with a suitable acid, such as hydrochloric acid.

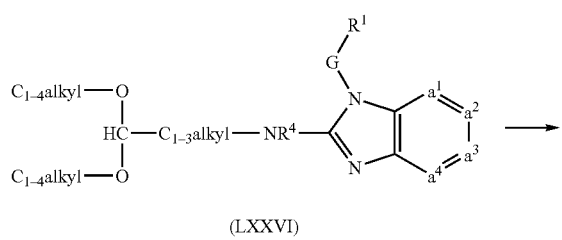

(LXXVI)

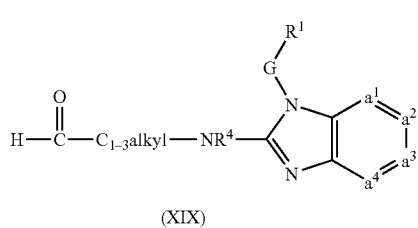

(XIX)

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid, respectively chiral base.

Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), (I') or the compounds of group (I") or any subgroup thereof, show antiviral properties. Viral infections treatable using the compounds and methods of the present invention include those infections brought on by ortho- and paramyxoviruses and in particular by human and bovine respiratory syncytial virus (RSV).

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. (Antiviral Research (1998), 38, 31–42).

Due to their antiviral properties, particularly their anti-RSV properties, the compounds of formula (I), (I') or the compounds of group (I") or any subgroup thereof, their prodrugs, N-oxides, addition salts, quaternary amines, metal complexes and stereochemically isomeric forms, are useful in the treatment of individuals experiencing a viral infection, particularly a RSV infection, and for the prophylaxis of these infections. In general, the compounds of the present invention may be useful in the treatment of warm-blooded animals infected with viruses, in particular the respiratory syncytial virus.

The compounds of formula (I') or the compounds of group (I") or any subgroup thereof may therefore be used as medicines. In particular, the compounds of formula (I), (I') or the compounds of group (I") may be used in the manufacture of a medicament for the treatment or the prevention of viral infections, especially RSV infections. The use as a medicine or method of treatment comprises the systemic administration to viral infected subjects or to subjects susceptible to viral infections of an amount effective to combat the conditions associated with the viral infection, in particular the RSV infection.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or as metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I') or a compound of the group (I") and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, suppositories, wafers, injectable solutions or suspensions and the like, and segregated multiples thereof.

In general it is contemplated that an antivirally effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

It may be appropriate to administer an antivirally effective daily dosage as two, three, four or more sub-doses at appropriate intervals throughout the day. Said sub-doses may be formulated as unit dosage forms.

The exact dosage and frequency of administration depends on the particular compound of formula (I), (I') or a compound of group (I") used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I), (I') or a compound of the group (I") can be used as a medicine. Thus, the present invention also relates to a product containing (a) a compound of formula (I), (I') or a compound of the group (I"), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

The following examples are intended to illustrate the present invention.

Experimental Part

Hereinafter, "DMF" is defined as N,N-dimethylformamide, "DIPE" is defined as diisopropylether, "DMSO" is defined as dimethylsulfoxide, and "THF" is defined as tetrahydrofuran.

Preparation of the Intermediate Compounds

EXAMPLE A1 a) NaOCH$_3$ (0.2 mol) was added to a mixture of N-(4-piperidinyl)-1H-benzimidazol-2-amine dihydrobromide (0.1 mol) in methanol (389 ml), the mixture was cooled on an ice bath and stirred for 2 hours. Bis(1,1-dimethylethyl) dicarbonoate (0.1 mol) was added to a cooled mixture on an ice bath and then stirred for 18 hours at room temperature. The mixture was evaporated and suspended in water/DIPE. The residue was filtered off, washed with water/DIPE and dried. The residue was boiled up in CH$_3$OH. Yield: 17.46 g of 1,1-dimethylethyl 4-(1H-benzimidazol-2-ylamino)-1-piperidinecarboxylate (55.2%) (interm. 1).

b) Preparation of

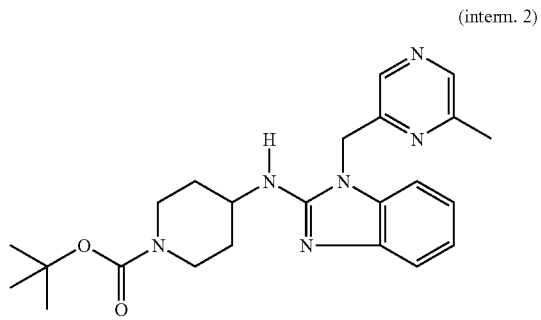
(interm. 2)

1-Bromo-2,5-pyrrolidinedione (0.055 mol) and then dibenzoyl peroxide (cat.quant.) were added to a mixture of 2,6-dimethylpyrazine (0.05 mol) in $CCl_4$ (100 ml). The mixture was stirred and refluxed for 4 hours, stirred at room temperature under $N_2$ flow overnight, cooled on an ice bath and filtered. The filtrate was evaporated, to give residue 1. NaH (0.04 mol) was added to a solution of intermediate (1) (0.04 mol) in DMF (150 ml). The mixture was stirred at room temperature under $N_2$ flow for 1 hour. Residue 1 was dissolved in DMF (50 ml) and added dropwise to the mixture. The mixture was stirred at 50° C. overnight. DMF was evaporated. The residue was taken up in $H_2O$ and the mixture was extracted with $CH_2Cl_2$. The organic layer was separated, dried, filtered and the solvent was evaporated. The residue was purified by column chromatography over silica gel (eluent: $CH_2Cl_2/CH_3OH$ 98/2). The pure fractions were collected and the solvent was evaporated. Yield: 6.82 g of intermediate (2) (32%).

EXAMPLE A2

Preparation of

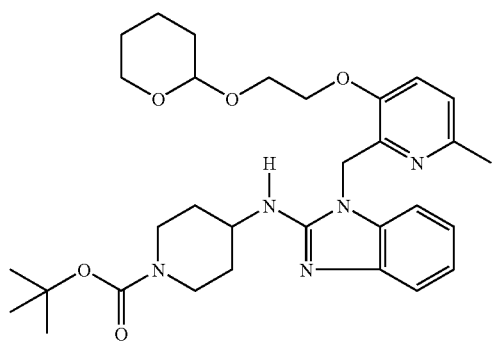
(interm. 3)

Reaction under $N_2$ flow. NaH 60% (0.02 mol) was added to a mixture of (±)-6-methyl-3-[2-[(tetrahydro-2H-pyran-2-yl)oxy]ethoxy]-2-pyridinemethanol (0.02 mol) in DMF (75 ml). Methanesulfonyl chloride (0.02 mol) was added. The mixture was added at room temperature to a mixture of intermediate (1) (0.02 mol) and NaH (0.022 mol) in DMF (100 ml), previously stirred at 40° C. for 1 hour. The mixture was stirred at room temperature overnight. The solvent was evaporated. The residue was taken up in $H_2O$ and $CH_2Cl_2$. The organic layer was separated, dried, filtered and the solvent was evaporated. The residue was purified by column chromatography over silica gel (eluent: $CH_2Cl_2/(CH_3OH/NH_3)$ 97/3). The pure fractions were collected and the solvent was evaporated. Yield: 3.52 g of intermediate (3) (31%).

EXAMPLE A3

Preparation of

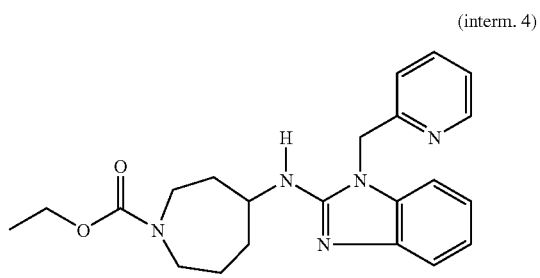
(interm. 4)

2-Chloro-1-(2-pyridylmethyl)-1H-benzimidazole (0.0615 mol) and ethyl 4-amino-hexahydro-1H-azepine-1-carboxylate (0.123 mol) were stirred at 160° C. for 3 hours. $H_2O$ was added and the mixture was extracted with $CH_2Cl_2$. The organic layer was separated, dried, filtered and the solvent was evaporated. The residue (13.6 g) was purified by column chromatography over silica gel (eluent: $CH_2Cl_2/CH_3OH/NH_4OH$ 98/2/0.1). The pure fractions were collected and the solvent was evaporated. Yield: 10.5 g of intermediate (4) (43%).

EXAMPLE A4 a) Preparation of

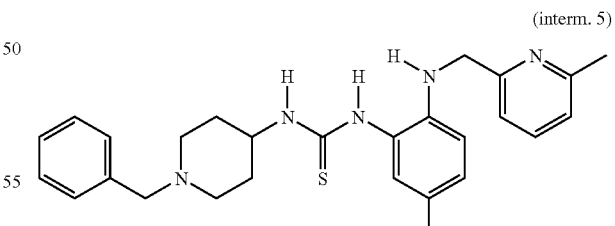
(interm. 5)

A mixture of ethyl 3-amino-4-[[(6-methyl-2-pyridyl)methyl]amino]benzoate (0.166 mol) and 4-isothiocyanato-1-(phenylmethyl)piperidine (0.166 mol) in ethanol (500 ml) was stirred and refluxed for 8 hours and at room temperature overnight. The precipitate was filtered off and used without further purification. Yield: intermediate (5).

b) Preparation of

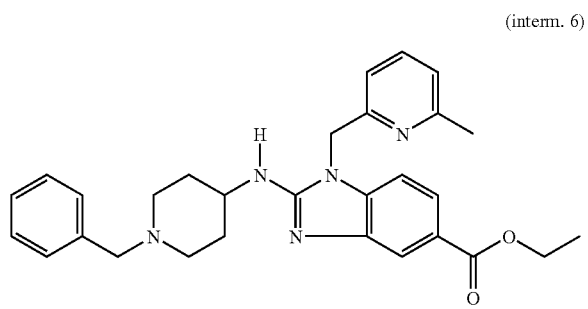
(interm. 6)

A mixture of intermediate (5) (0.16 mol), HgO (0.192 mol) and S (spat.tip) in DMF (100 ml) was stirred at 80° C. for 4 hours, filtered warm over dicalite, washed with warm DMF, heated again and filtered warm over dicalite. The solvent was evaporated. The residue was taken up in CH$_2$Cl$_2$. The mixture was washed with H$_2$O. The organic layer was separated, dried (MgSO$_4$), filtered and the solvent was evaporated. The residue was co-evaporated with toluene. The residue was crystallized from CH$_3$CN. The precipitate was filtered off and dried. Yield: 53.5 g of intermediate (6) (70%)

EXAMPLE A5 a) Preparation of

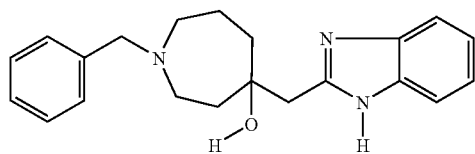
(interm. 7)

A mixture of N-(1-methylethyl)-2-propanamine (0.098 mol) in THF (100 ml) was stirred at −40° C. under N$_2$ flow. BuLi 1.6M in hexane (0.098 mol) was added dropwise. The mixture was stirred at −40° C. for 30 min and cooled to −70° C. A mixture of 1-(diethoxymethyl)-2-methyl-1H-benzimidazole (0.098 mol) in THF (50 ml) was added dropwise and the mixture was stirred for 45 minutes. A mixture of hexahydro-1-(phenylmethyl)-4H-azepin-4-one (0.049 mol) in THF (50 ml) was added dropwise at −70° C. The mixture was hydrolized cold and extracted with EtOAc. The organic layer was separated, dried, filtered and the solvent was evaporated. The residue was purified by column chromatography over silica gel (eluent: CH$_2$Cl$_2$/CH$_3$OH 98/2). The pure fractions were collected and the solvent was evaporated (yielding 7.5 g). Part of the residue (3.5 g) was crystallized from EtOAc. The precipitate was filtered off and dried. Yield: 2.3 g of intermediate (7).

b) Preparation of

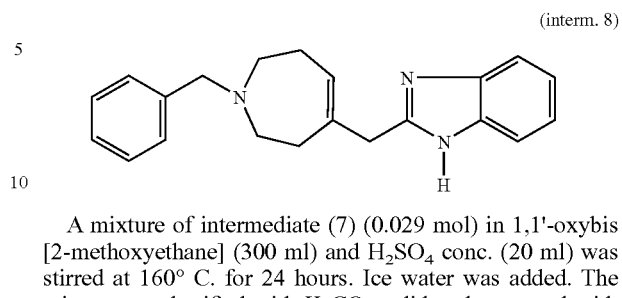
(interm. 8)

A mixture of intermediate (7) (0.029 mol) in 1,1'-oxybis[2-methoxyethane] (300 ml) and H$_2$SO$_4$ conc. (20 ml) was stirred at 160° C. for 24 hours. Ice water was added. The mixture was basified with K$_2$CO$_3$ solid and extracted with CH$_2$Cl$_2$. The organic layer was separated, dried, filtered and the solvent was evaporated. Yield: 18 g of a mixture of 2 compounds, of which one compound is intermediate (8) (75%).

c) Preparation of

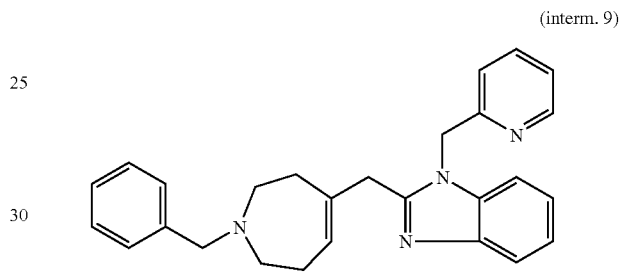
(interm. 9)

A mixture of intermediate (8), 2-(chloromethyl)pyridine (0.047 mol) and K$_2$CO$_3$ (0.0775 mol) in acetonitrile (500 ml) was stirred and refluxed for 24 hours. H$_2$O was added and the mixture was extracted with CH$_2$Cl$_2$. The organic layer was separated, dried, filtered and the solvent was evaporated. Yield: 15.4 g of a mixture of 2 compounds, of which one is intermediate (9).

EXAMPLE A6

Preparation of

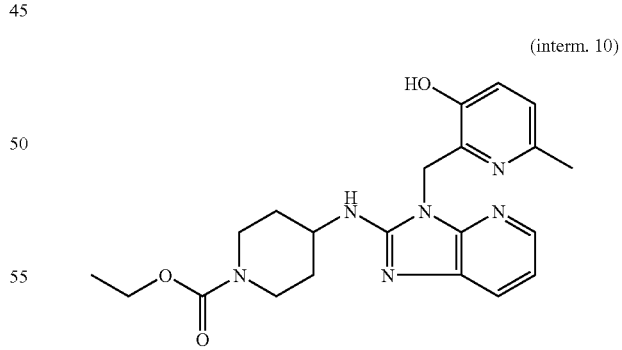
(interm. 10)

N,N-diethylethamine (16 ml) and then 2-chloromethyl-6-methyl-3-pyridinol (0.0376 mol) were added to a mixture of ethyl 4-[(3H-imidazo[4,5-b]pyridin-2-yl)amino]-1-piperidinecarboxylate (0.0376 mol) in DMF (550 ml). The mixture was stirred at room temperature for 3 hours and at 50° C. overnight. The solvent was evaporated. The residue was poured out into H$_2$O and CH$_2$Cl$_2$. The organic layer was separated, dried, filtered and the solvent was evaporated. The residue was purified by HPLC over silica gel (eluent:

CH$_2$Cl$_2$/C$_2$H$_5$OH 95/5 to 70/30). The desired fraction was collected and the solvent was evaporated. Yield: 2.1 g of intermediate (10).

EXAMPLE A7 a) Preparation of

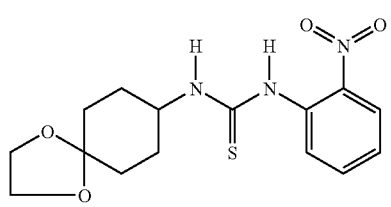
(interm. 11)

A mixture of 1,4-dioxaspiro[4,5]decan-8-amine (0.28 mol) and 1-isothiocyanato-2-nitrobenzene (0.28 mol) in ethanol (300 ml) was stirred at room temperature for 2 hours. The solvent was evaporated. The product was used without further purification. Yield: 90 g of intermediate (11).

b) Preparation of

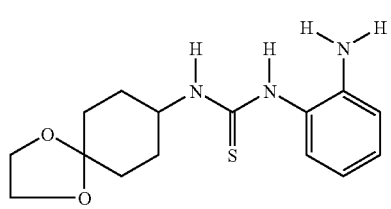
(interm. 12)

A mixture of intermediate (11) (0.178 mol) in NH$_3$/CH$_3$OH (500 ml) and THF (100 ml) was hydrogenated at room temperature under a 3 bar pressure for 24 hours with Pd/C (52 g) as a catalyst. After uptake of H$_2$ (3 equiv), the catalyst was filtered through celite, washed with CH$_3$OH and the filtrate was evaporated. The product was used without further purification. Yield: 44 g of intermediate (12).

c) Preparation of

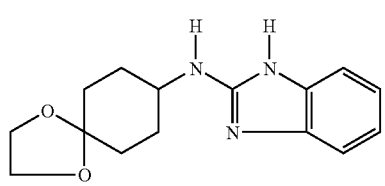
(interm.13)

A mixture of intermediate (12) (0.071 mol), HgO (0.142 mol) and S (0.56 g) in ethanol (300 ml) was stirred and refluxed for 4 hours, filtered over celite, washed with CH$_2$Cl$_2$ and the filtrate was evaporated. The reaction was carried out again using the same quantities. The residues were combined and then purified by column chromatography over silica gel (eluent: CH$_2$Cl$_2$/CH$_3$OH/NH$_4$OH 94/6/0.5; 20–45 µm). The pure fractions were collected and the solvent was evaporated. Yield: 14.5 g of intermediate (13) (43%); mp. >260° C.

d) Preparation of

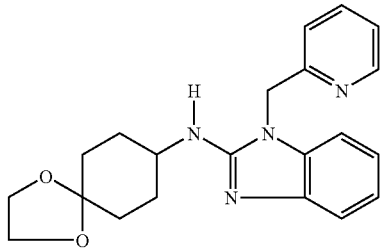
(interm. 14)

A mixture of intermediate (13) (0.049 mol), 2-(chloromethyl)pyridine (0.0735 mol) and K$_2$CO$_3$ (0.196 mol) in acetonitrile (325 ml) was stirred and refluxed for 4 hours and then brought to room temperature. The reaction was carried out again using the same quantities. The mixtures were combined. H$_2$O was added and the mixture was extracted with EtOAc. The organic layer was separated, dried (MgSO$_4$), filtered and the solvent was evaporated. The residue was purified by column chromatography over silica gel (eluent: CH$_2$Cl$_2$/CH$_3$OH/NH$_4$OH 98/2/0.1; 20–45 µm). The pure fractions were collected and the solvent was evaporated. Part of this fraction (0.6 g) was crystallized from diethyl ether. The precipitate was filtered off and dried. Yield: 0.46 g of intermediate (14); mp. 136° C.

e) Preparation of

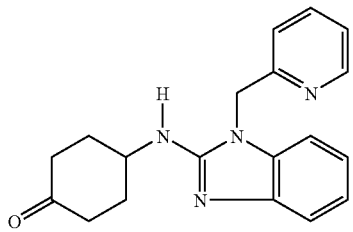
(interm. 15)

A mixture of intermediate (14) (0.077 mol) in HCl 3N (350 ml) was stirred and refluxed for 1 hour, poured out into ice water, basified with K$_2$CO$_3$ solid and extracted with CH$_2$Cl$_2$. The organic layer was separated, washed with H$_2$O, dried (MgSO$_4$), filtered and the solvent was evaporated. Part of the residue (1.5 g) was crystallized from CH$_3$CN and diethyl ether. The precipitate was filtered off and dried. Yield: 0.5 g of intermediate (15); mp. 148° C.

EXAMPLE A8 a) Preparation of

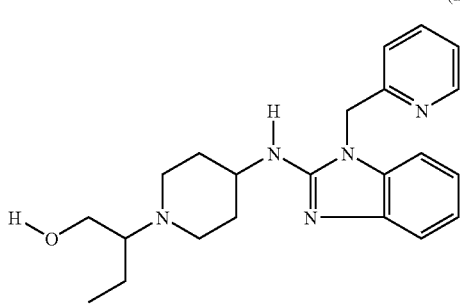
(interm. 16)

LiAlH₄ (0.023 mol) was added portionwise at 5° C. to a solution of (±)-ethyl α-ethyl-4-[[1-(2-pyridylmethyl)-1H-benzimidazol-2-yl]amino]-1-piperidineacetate (0.021 mol) in THF (100 ml). The mixture was stirred at 5° C. for 1 hour. EtOAc was added. The mixture was hydrolized with ice water, filtered over celite, washed with EtOAc, dried (MgSO₄), filtered and the solvent was evaporated. Yield: 7.2 g of intermediate (16) (88%).

b) Preparation of

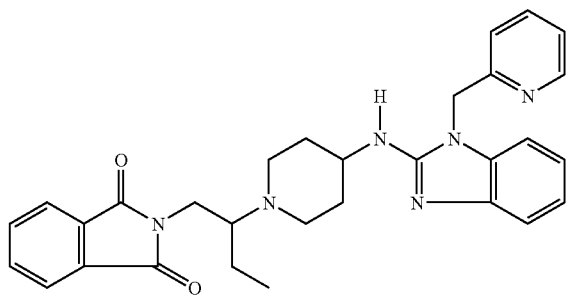

(interm. 17)

Diethyl azodicarboxylate (0.028 mol) was added slowly at room temperature to a solution of intermediate (16) (0.019 mol), 1H-isoindole-1,3(2H)-dione (0.028 mol) and triphenyl phosphine (0.028 mol) in THF (200 ml). The mixture was stirred at room temperature for 8 hours. The solvent was evaporated till dryness. The residue was dissolved in CH₂Cl₂. The solution was acidified with HCl 3N, basified with NH₄OH and extracted with CH₂Cl₂. The organic layer was separated, dried (MgSO₄), filtered and the solvent was evaporated. The residue (12 g) was purified by column chromatography over silica gel (eluent: CH₂Cl₂/CH₃OH/NH₄OH 97/3/0.1; 20–45 μm). The pure fractions were collected and the solvent was evaporated. Yield: 5.5 g of intermediate (17) (57%).

EXAMPLE A9 a) Preparation of

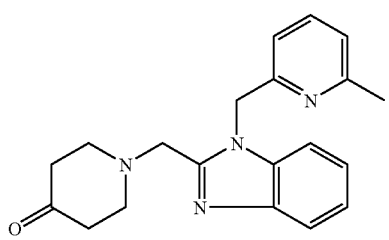

(interm. 18)

A mixture of 8-[[1-[(6-methyl-2-pyridyl)methyl]-1H-benzimidazol-2-yl]methyl]-1,4,8-dioxa-8-azaspiro[4.5]decane (0.0196 mol) in HCl 6N (55 ml) and H₂O (55 ml) was stirred and refluxed for 6 hours. Toluene was added. The mixture was poured out on ice, alkalized with a NaOH solution and extracted with CH₂Cl₂. The organic layer was separated, dried, filtered and the solvent was evaporated. Part of this fraction was suspended in DIPE, filtered off and dried. Yield: 0.32 g of intermediate (18) (91%).

b) Preparation of

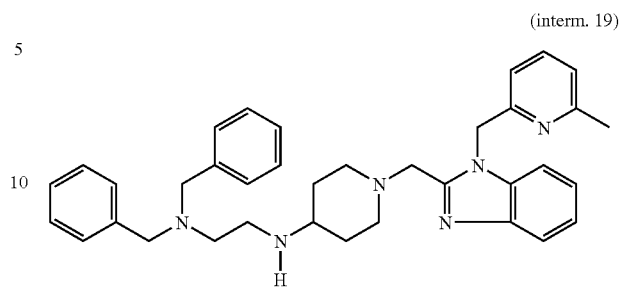

(interm. 19)

A mixture of intermediate (18) (0.008 mol) and N,N-dibenzylethylenediamine (0.01 mol) in methanol (150 ml) was hydrogenated with Pd/C 10% (1 g) as a catalyst in the presence of thiophene solution (0.5 ml). After uptake of H₂ (1 equiv), the catalyst was filtered off and the filtrate was evaporated. Yield: 5.39 g of intermediate (19) (quant.).

EXAMPLE A10 a) Preparation of

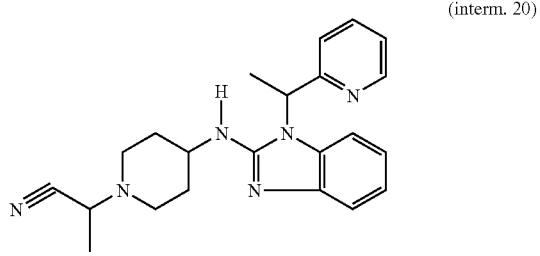

(interm. 20)

A mixture of (±)—N-(4-piperidinyl)-1-[1-(2-pyridyl)ethyl]-1H-benzimidazol-2-amine (0.026 mol), 2-chloropropanenitrile (0.039 mol) and K₂CO₃ (0.052 mol) in acetonitrile (100 ml) was stirred and refluxed for 8 hours. H₂O was added and the mixture was extracted with EtOAc. The organic layer was separated, dried (MgSO₄), filtered and the solvent was evaporated. The residue (8.5 g) was purified by column chromatography over silica gel (eluent: CH₂Cl₂/CH₃OH 96/4; 20–45 μm). The pure fractions were collected and the solvent was evaporated. Yield: 4.5 g of intermediate (20) (46%).

b) Preparation of

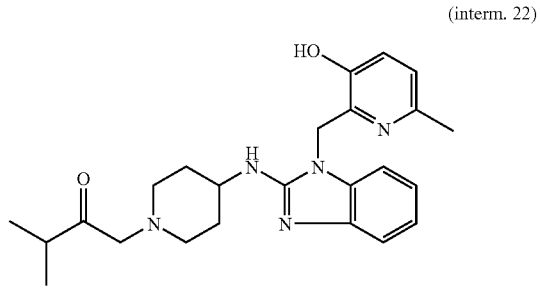

(interm. 22)

A mixture of compound 49 (0.0164 mol), 1-bromo-3-methyl-2-butanone (0.03 mol) and K₂CO₃ (0.06 mol) in CH₃CN (100 ml) was stirred and refluxed for several hours. H₂O was added. The solvent was evaporated. 4-Methyl-2-pentanone was added. The organic layer was separated, dried, filtered and the solvent was evaporated. The residue was purified by column chromatography over silica gel (eluent: CH₂Cl₂/(CH₃OH/NH₃) 98/2). The desired fractions were collected and the solvent was evaporated. Yield: 2.75 g of intermediate (22) (40%).

EXAMPLE A11

Preparation of

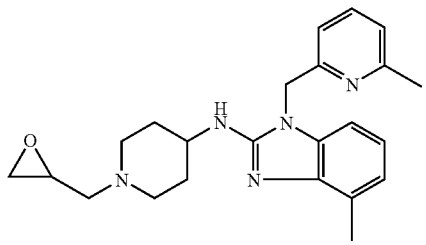
(interm. 21)

A mixture of compound 90 (0.015 mol), (chloromethyl) oxirane (0.008 mol) and Na₂CO₃ (1.59 g) in 4-methyl-2-pentanone (150 ml) was heated slowly to 100° C. (to 40° C. in 1 hour, 70° C. in 1 hour), stirred at 100° C. overnight, then stirred and refluxed for 20 hours. The solvent was evaporated. The residue was purified by column chromatography over silica gel (eluent: CH₂Cl₂/(CH₃OH/NH₃) 95/5). Two fractions were collected and their solvents were evaporated. Fraction 1 was crystallized from DIPE. The precipitate was filtered off and dried. Yield: 0.18 g of intermediate (21).

EXAMPLE A12 a) Preparation of

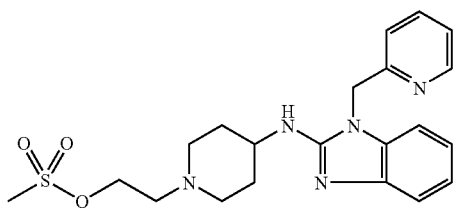
(interm. 23)

Methylsulfonyl chloride (0.0512 mol) was added dropwise at 0° C. under N₂ flow to a mixture of 4-[[1-(2-pyridinylmethyl)-1H-benzimidazol-2-yl]amino]-1-piperidineethanol (0.0256 mol) and N,N-diethylethanamine (0.0512 mol) in CH₂Cl₂ (200 ml). The mixture was stirred at room temperature for 90 minutes. The solvent was evaporated till dryness. Yielding: intermediate (23)

b) Preparation of

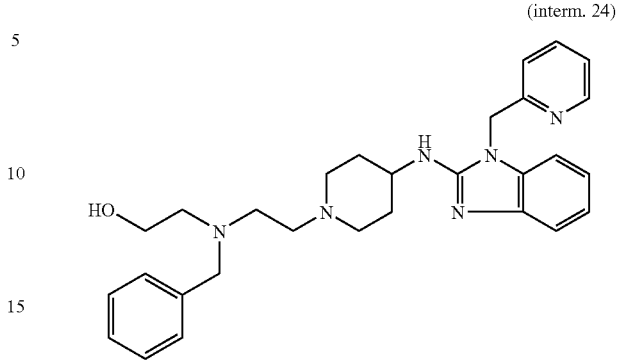
(interm. 24)

A mixture of intermediate (23) (0.028 mol), 2-[(phenylmethyl)amino]ethanol, (0.034 mol) and K₂CO₃ (0.112 mol) in CH₃CN (200 ml) was stirred at 60° C. for 4 hours. H₂O was added and the mixture was extracted with ethyl acetate. The organic layer was separated, dried (MgSO₄), filtered and the solvent was evaporated. The residue (13.5 g) was purified by column chromatography over silica gel (eluent: CH₂Cl₂/CH₃OH/NH₄OH 97/3/0.5; 35–70 μm). The pure fractions were collected and the solvent was evaporated. Yield: 5.5 g of intermediate (24) (41%).

EXAMPLE A13

Preparation of

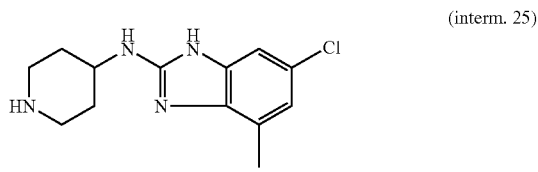
(interm. 25)

HCl 12N (165 ml) was added to a mixture of

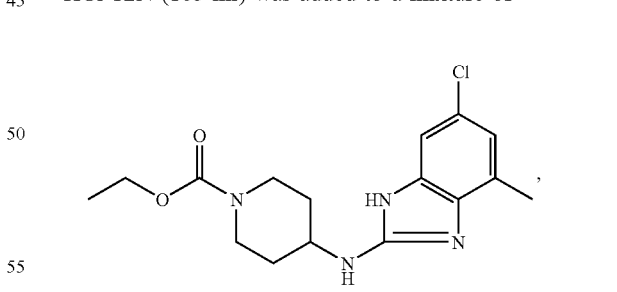

(interm. 36), prepared according to example A7c), (0.049 mol) in H₂O (165 ml). The mixture was stirred and refluxed for 6 hours. The solvent was evaporated. HBr 48% (320 ml) was added. The mixture was stirred and refluxed for 4 hours and then stirred overnight. The solvent was evaporated. 2-Propanol was added and the solvent was evaporated again. The residue was suspended in DIPE. The mixture was decanted, taken up in H₂O/DIPE and then separated into its layers. CH₂Cl₂ was added to the aqueous layer. The mixture was alkalized with NH$_4$OH. 2-Propanol was added. The organic layer was separated, dried, filtered and the solvent was evaporated. Yield: 15 g of intermediate (25).

EXAMPLE A14 a) Preparation of

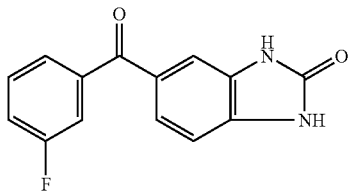
(interm. 26)

3,4-diaminophenyl-(3-fluorophenyl)methanone (0.056 mol) and urea (0.084 mol) were stirred at 150 à 160° C. for 4 hours (melt) and then cooled. Water was added. The mixture was stirred at 50° C. for a while and then cooled. The precipitate was filtered off, stirred in 2-propanone and dried. Yield: 11.4 g of intermediate (26).

b) Preparation of

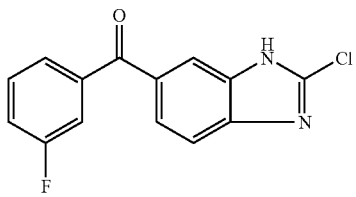
(interm. 27)

Phosphorus oxychloride (50 ml) was added carefully to intermediate (26) (0.045 mol). The mixture was stirred and refluxed for 24 hours and then was stood at room temperature over the weekend. The solvent was evaporated. The residue was taken up in CH$_2$Cl$_2$/ice/K$_2$CO$_3$ solid. The mixture was separated into its layers. The aqueous layer was extracted with CH$_2$Cl$_2$. The undissolved material was filtered off to give residue 1. The combined organic layer was dried, filtered and the solvent was evaporated to give residue 2. Residue 1 and residue 2 were combined. Yield: 16.75 g of intermediate (27) (100%).

EXAMPLE A15

Preparation of

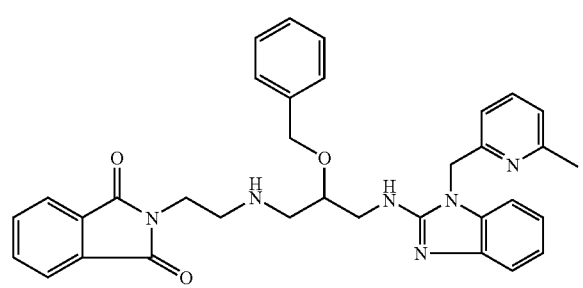
(interm. 28)

A mixture of compound (341) (0.0025 mol), prepared according to B25a), 2-(2-bromoethyl)-1H-Isoindole-1,3 (2H)-dione (0.00275 mol) and K$_2$CO$_3$ (3 g) in CH$_3$CN (100 ml) was stirred and refluxed for 24 hours. The solvent was evaporated. The residue was dissolved in CH$_2$Cl$_2$ and then washed with water. The organic layer was dried (MgSO$_4$), filtered and the solvent was evaporated. The residue was purified by column chromatography over silica gel (eluent: CH$_2$Cl/(CH$_3$OH/NH$_3$) 97/3). The pure fractions were collected and the solvent was evaporated. Yield: intermediate (28).

EXAMPLE A16 a) 2,4,5-trimethyloxazole (0.225 mol) was stirred in CCl$_4$ (500 mL) under N$_2$-flow. Then 1-bromo-2,5-pyrrolidinedione (0.225 mol) and benzoyl peroxide (cat.quant.) were added. This mixture was stirred and refluxed for 1 hour under N$_2$-flow. The reaction mixture was cooled in an ice bath (ice/salt). The mixture was filtered. The filtrate was evaporated. Yield: 42.7 g (<100%) of 5-(bromomethyl)-2,4-dimethyloxazole (intermediate 30).

b) Intermediate (30) (0.225 mol) was taken up in DMF (450 ml). Na[N(CH(=O))$_2$] (0.225 mol) was added portionwise and the mixture was stirred at 50° C. for 1 hour and at room temperature overnight. The mixture was evaporated. Yield: 41 g (100%) of N-[(2,4-dimethyl-5-oxazolyl)methyl]-N-formylformamide (intermediate 31).

c) A mixture of intermediate (31) (0.225 mol) in HCl 36% (120 ml) and ethanol (500 ml) was refluxed for 1 hour and stirred overnight. The mixture was filtered off, the precipitate was washed with C$_2$H$_5$OH and the filtrate was evaporated. The residue was taken up in ice water, alkalized with NaOH and extracted with CH$_2$Cl$_2$. The mixture was separated and the organic layer was dried and evaporated. Yield: 28 g (100%) of 2,4-dimethyl-5-oxazolmethanamine (intermediate 32).

d) 2-chloro-3-nitropyridine (0.225 mol) and Na$_2$CO$_3$ (0.225 mol) were added to a mixture of intermediate (32) (0.225 mol) in ethanol (500 ml) and the mixture was stirred and refluxed for 6 hours. The mixture was evaporated and the residue was taken up in water and extracted with CH$_2$Cl$_2$. The mixture was separated and the organic layer was dried, filtered off and evaporated. The residue was purified by column chromatography over silica gel. The pure fractions were collected and evaporated. Yield: 27 g (48%) of N-[(2,4-dimethyl-5-oxazolyl)methyl]3-nitro-2-pyridinamine (intermediate 33).

e) A mixture of intermediate (33) (0.1 mol) was hydrogenated in a thiophene solution 4% (3 ml) and methanol (400 ml) with Pd/C$_5$% (4 g) as a catalyst. After uptake of H$_2$ (3 eq), the catalyst was filtered off. The residue was evaporated and used without further purification. Yield: 21.8 g (100%) of N$^2$-[(2,4-dimethyl-5-oxazolyl)methyl]-2,3-pyridinediamine (intermediate 34).

f) Intermediate (34) (0.1 mol) was dissolved in DMF (250 ml). Ethyl 4-isothiocyanato-1-piperidinecarboxylate (0.1 mol) was added and the mixture was stirred at 50° C. for 20 hours. HgO (0.125 mol) and sulfur powder (few crystals) were added and the mixture was stirred at 75° C. for 3 hours 30 minutes. The mixture was filtered over dicalite and the filtrate was evaporated. The residue was taken up in water/ CH$_2$Cl$_2$. The mixture was separated, the organic layer was dried, filtered off and evaporated. The residue was purified by column chromatography over silica gel (eluent: CH$_2$Cl$_2$/CH$_3$OH 95/5). The pure fractions were collected and evaporated. The residue was crystallized from DIPE and recrystallized from CH₃CN. Yield: 216.6277 g (55.4%) of ethyl 4-[[3-[(2,4dimethyl-5-oxazolyl)methyl]-3H-imidazo[4,5-b]pyridin-2-yl]amino-1-piperidinecarboxylate (intermediate 35).

EXAMPLE A17

Cl—CH₂—C(=NH)—O—C₂H₅ (0.0625 mol) was added to a mixture of N²-[(2-methyl-5-oxazolyl)methyl]-2,3-pyridinediamine (0.05 mol) in acetic acid (150 mL) and the mixture was stirred for 20 hours at room temperature. The mixture was warmed up to 90° C. and stirred for 10 minutes at this temperature. The mixture was evaporated at <50° C. The residue was taken up in water/CH₂Cl₂+Na₂CO₃. The organic layer was separated, extracted with CH₂Cl₂, dried (MgSO₄) and filtered. The residue was taken up in DIPE+active charcoal and stirred for 1 hour. The mixture was filtered and evaporated, Yield: 13.1 g (100%) of 2-(chloromethyl)-3-[(2-methyl-5-oxazolyl)methyl]-3H-imidazo[4,5-b]pyridine (intermediate 29). Preparation of the final compounds

EXAMPLE B1 a) Preparation of

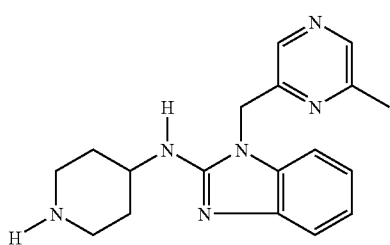

(compound 1)

A mixture of intermediate (2) (0.016 mol) in 2-propanol/HCl (10 ml) and 2-propanol (100 ml) was stirred and refluxed for 2 hours and then cooled. The precipitate was filtered off, washed with DIPE and dried. The residue was taken up in H₂O, NH₃ and CH₃OH and the mixture was extracted with CH₂Cl₂. The organic layer was separated, dried, filtered and the solvent was evaporated. The residue was purified over silica gel on a glass filter (eluent: CH₂Cl₂/(CH₃OH/NH₃) 90/10). The pure fractions were collected and the solvent was evaporated. Yield: 1.8 g of compound (1) (35%).

b) Preparation of

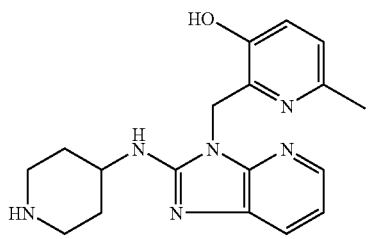

(compound 308)

A mixture of intermediate (10) (0.0054 mol) in HBr 48% (50 ml) was stirred and refluxed for 5 hours. The solvent was evaporated. The residue was suspended in DIPE, filtered off and crystallized from ethanol. The solvent was evaporated and the fraction was purified by high-performance liquid chromatography over RP Hyperprep (eluent: (0.5% NH₄OAc in H₂O)/CH₃CN from 100/0 to 0/100). The pure fractions were collected and the solvent was evaporated. Yield: 0.188 g of compound (308).

EXAMPLE B2 a) Preparation of

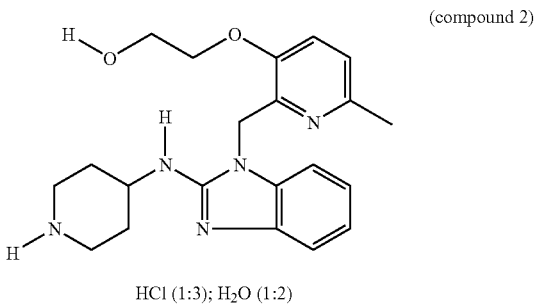

(compound 2)

HCl (1:3); H₂O (1:2)

A mixture of intermediate (3) (0.00622 mol) in 2-propanol/HCl (10 ml) and 2-propanol (100 ml) was stirred and refluxed for 4 hours. The solvent was evaporated. The residue was taken up in H₂O, Na₂CO₃ and CH₂Cl₂. The organic layer was separated, dried, filtered and the solvent was evaporated. The residue was dissolved in 2-propanol and DIPE and converted into the hydrochloric acid salt with 2-propanol/HCl. The precipitate was filtered off and dried. This fraction was converted into the free base and purified over silica gel on a glass filter (eluent: CH₂Cl₂/(CH₃OH/NH₃) 90/10). The pure fractions were collected and the solvent was evaporated. The residue was converted into the hydrochloric acid salt (1:3). The precipitate was filtered off and dried. Yield: 0.65 g of compound (2) (20%).

b) Preparation of

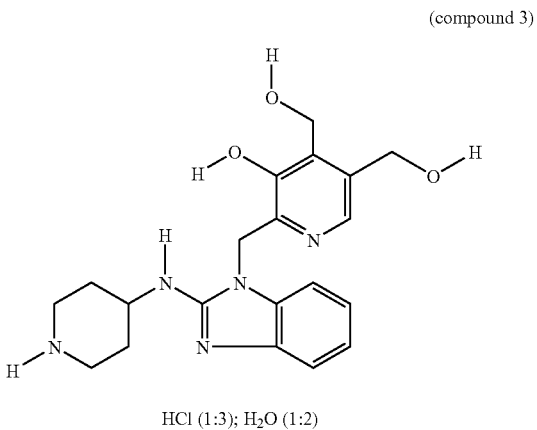

(compound 3)

HCl (1:3); H₂O (1:2)

A mixture of 1,1-dimethylethyl 4-[[1-[[3,5-dihydro-3,3-dimethyl-9-(phenylmethoxy)-1H-[1,3]dioxepino[5,6-c]pyridin-2-yl]methyl]-H-benzimidazol-2-yl]amino]-1-piperidinecarboxylate (0.00552 mol) in HCl 10N (200 ml) was stirred and refluxed for 6 hours. The solvent was evaporated. The residue was suspended in DIPE, filtered off and dried. Yield: 0.58 g of compound (3).

EXAMPLE B3

Preparation of

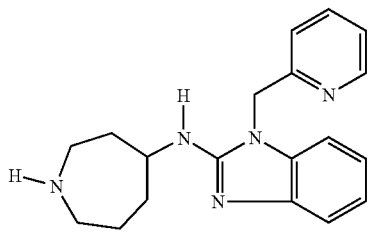
(compound 4)

A mixture of intermediate (4) (0.021 mol) and KOH (0.43 mol) in 2-propanol (100 ml) was stirred and refluxed overnight. H$_2$O was added and the mixture was extracted with CH$_2$Cl$_2$. The organic layer was separated, dried (MgSO$_4$), filtered and the solvent was evaporated. Yield: 6.9 g of compound (4) (quant.).

EXAMPLE B4

Preparation of

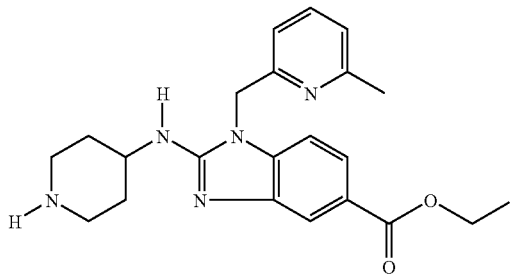
(compound 5)

A mixture of intermediate (6) (0.02 mol) in ethanol (120 ml) was hydrogenated with Pd/C 10% (2 g) as a catalyst. After uptake of H$_2$ (1 equiv), the catalyst was filtered off and the filtrate was evaporated, yielding a residue of 8 g (100%). Part of this fraction (0.7 g) was dissolved in ethanol and converted into the hydrochloric acid salt (1:3) with 2-propanol/HCl. DIPE was added. The mixture was stirred. The precipitate was filtered off and dried. Yield: 0.65 g of compound (5).

EXAMPLE B5

Preparation of

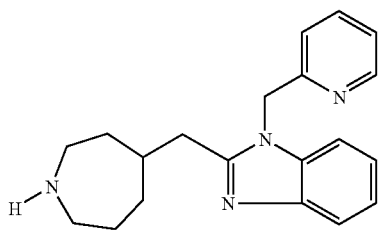
(compound 6)

A mixture of intermediate (9) (0.035 mol) in methanol (200 ml) was hydrogenated at room temperature under a 3 bar pressure for 48 hours with Pd/C (1.5 g) as a catalyst, then hydrogenation was continued at 40° C. under a 3 bar pressure for 48 hours. After uptake of H$_2$ (2 equiv), the catalyst was filtered through celite and the filtrate was evaporated. The residue (12 g) was purified by column chromatography over silica gel (eluent: CH$_2$Cl$_2$/CH$_3$OH/NH$_4$OH 80/20/3). The pure fractions were collected and the solvent was evaporated. Yield: 3.8 g of compound (6) (34%).

EXAMPLE B6

Preparation of

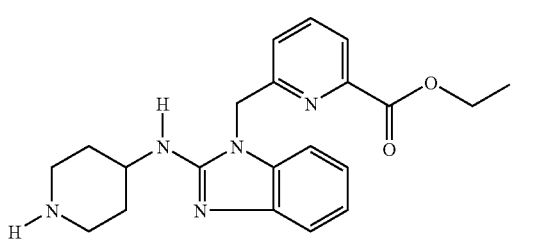
(compound 7)

A mixture of 6-[[2-(4-piperidinylamino)-1H-benzimidazol-1-yl]methyl]-2-pyridine-carboxylic acid in HCl 36% (5 ml) and ethanol (50 ml) was stirred and refluxed overnight. The solvent was evaporated. H$_2$O, NaHCO$_3$ and CH$_2$Cl$_2$ were added. The organic layer was separated, dried, filtered and the solvent was evaporated. The residue was purified over silica gel on a glass filter (eluent: CH$_2$Cl$_2$/(CH$_3$OH/NH$_3$) 90/10). The pure fractions were collected and the solvent was evaporated. Yield: 0.83 g of compound (7).

EXAMPLE B7

Preparation of

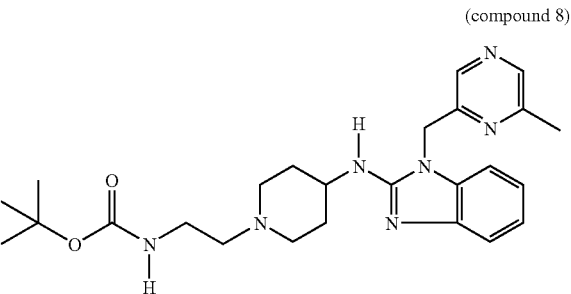
(compound 8)

A mixture of compound (1) (0.003 mol), 1,1-dimethylethyl(2-bromoethyl) carbamate (0.004 mol) and Na$_2$CO$_3$ (0.004 mol) in 2-butanone (100 ml) was stirred and refluxed overnight. The reaction mixture was cooled, washed with water and the layers were separated. The organic phase was washed with a NH$_4$Cl solution. The aqueous phase was extracted with CH$_2$Cl$_2$. The combined organic layers were dried, filtered and the solvent was evaporated. The residue was purified over silica gel on a glass filter (eluent: CH$_2$Cl$_2$/(CH$_3$OH/NH$_3$) 97/3). The pure fractions were collected and the solvent was evaporated. Yield: a residue of 1.18 g of compound (8) (84%).

EXAMPLE B8

Preparation of (compound 9)

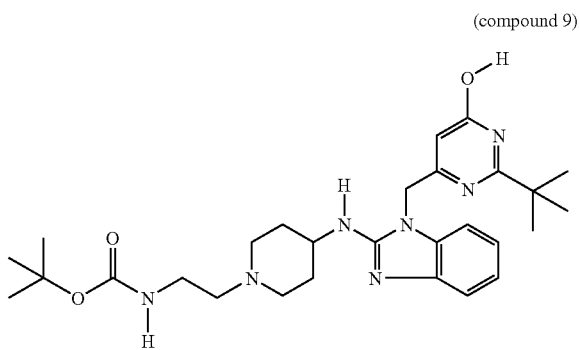

Reaction under $N_2$ flow. NaH (0.01 mol) was added to a mixture of 1,1-dimethylethyl [2-[4-(1H-benzimidazol-2-ylamino)-1-piperidinyl]ethyl]carbamate (0.01 mol) in DMF p.a. dry (100 ml). The mixture was stirred at room temperature for 4 hours. 6-chloro-methyl-2-(1,1-dimethylethyl)$_4$-pyrimidinol (0.01 mol) in a small amount of DMF p.a. dry was added dropwise. The mixture was stirred at 50° C. overnight and then cooled. $H_2O$ (50 ml) was added. The solvent was evaporated. The residue was taken up in $CH_2Cl_2$. The organic solution was washed with $H_2O$/HOAc, dried ($MgSO_4$), filtered and the solvent was evaporated, to give residue 1. The aqueous layer was taken up in HOAc and extracted with $CH_2Cl_2$. The organic layer was separated, dried ($MgSO_4$), filtered and the solvent was evaporated, to give residue 2. Residue 1 and 2 were combined and purified by column chromatography over RP 18 BDS (eluent: $NH_4OAc$ (0.5% in $H_2O$)/$CH_3OH$/$CH_3CN$ 70/15/15, 0/50/50 and 0/0/100). The pure fractions were collected and the solvent was evaporated. Yield: compound (9).

EXAMPLE B9 a) Preparation of (compound 10)

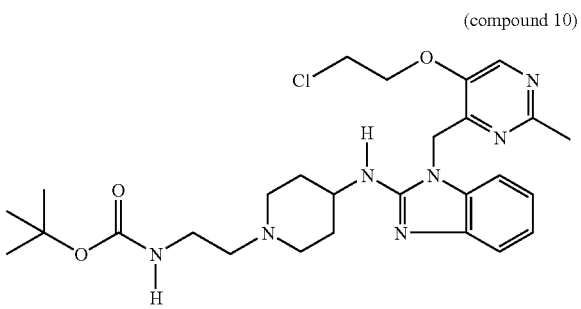

Thionyl chloride (0.03 mol) was added to a mixture of ±-6-methyl-3-[2-[(tetrahydro-2H-pyran-2-yl)oxy]ethoxy]-2-pyridinemethanol (0.015 mol) in $CH_2Cl_2$ (100 ml). Toluene was added and evaporated again. The residue was taken up in DMF (50 ml) and then added to a mixture of 1,1-dimethylethyl[2-[4-(1H-benzimidazol-2-ylamino)-1-piperidinyl]ethyl]carbamate (0.015 mol) and NaH (0.06 mol) in DMF (200 ml). The mixture was stirred at 50° C. overnight. The solvent was evaporated. The residue was taken up in $H_2O$ and $CH_2Cl_2$. The organic layer was separated, dried, filtered and the solvent was evaporated. The residue was purified over silica gel on a glass filter (eluent: $CH_2Cl_2$/($CH_3OH$/$NH_3$) 99/1). The pure fractions were collected and the solvent was evaporated. The residue was suspended in petroleum ether. The precipitate was filtered off and dried. Yield: 1.55 g of compound (10) (20%).

b) Preparation of (compound 11)

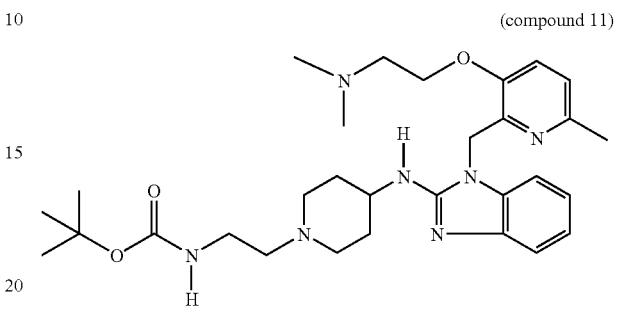

A mixture of compound (10) (0.00147 mol) and $NH(CH_3)_2$ gas (20 g) in THF (100 ml) was stirred at 125° C. for 16 hours. The solvent was evaporated. The residue was purified over silica gel on a glass filter (eluent: $CH_2Cl_2$/($CH_3OH$/$NH_3$) 95/5). The pure fractions were collected and the solvent was evaporated. Yield: 0.43 g of compound (11) (53%).

EXAMPLE B10 a) Preparation of (compound 12)

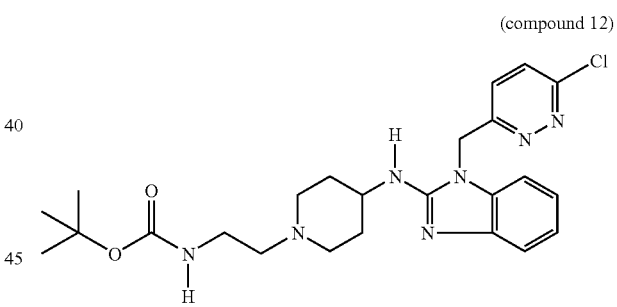

1-Bromo-2,5-pyrrolidinedione (0.088 mol) and then dibenzoyl peroxide (cat.quant.) were added to a solution of 3-chloro-6-methylpyridazine (0.08 mol) in $CCl_4$ (mol. sieves) (200 ml). The mixture was stirred and refluxed for 6 hours and then filtered over dicalite. 1-Bromo-2,5-pyrrolidinedione (0.088 mol) and dibenzoyl peroxide (cat.quant.) were added again. The mixture was stirred and refluxed overnight and filtered over dicalite. The solvent was evaporated at a temperature below 40° C. The residue was dissolved in DMF (70 ml) and added to a mixture of 1,1-dimethylethyl [2-[4-(1H-benzimidazol-2-ylamino)-1-piperidinyl]ethyl]carbamate (0.0214 mol) and NaH (0.0235 mol) in DMF (190 ml), previously stirred at room temperature for 1 hour and at 40° C. for 1 hour. The resulting mixture was stirred at 50° C. overnight. The solvent was evaporated. $H_2O$ and $CH_2Cl_2$ were added. The organic layer was separated, dried, filtered and the solvent was evaporated. The residue was purified by column chromatography over silica gel (eluent: $CH_2Cl_2$/($CH_3OH$/$NH_3$) 97/3). The pure fractions were collected and their solvents were evaporated. Yield: 1.21 g of compound (12).

b) Preparation of (compound 13)

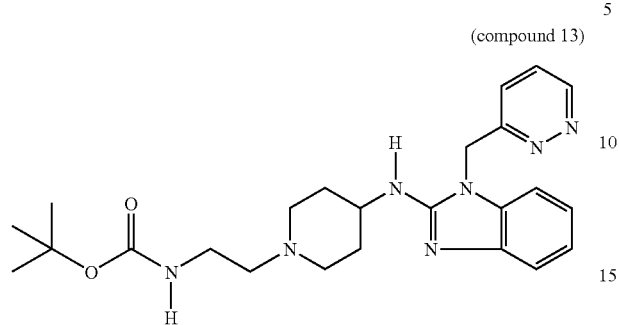

A mixture of compound (12) (0.0025 mol), CaO (2 g) and Pd/C (1 g) in 1-butanethiol (2 ml) and THF (100 ml) was stirred at room temperature for the weekend. The solvent was evaporated. Yield: 1 g of compound (13) (88%).

EXAMPLE B11

Preparation of (compound 14)

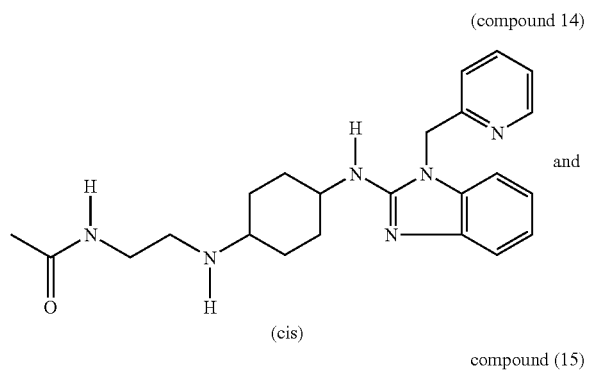

and compound (15)

A mixture of intermediate (15) (0.031 mol) and N-(2-aminoethyl)acetamide (0.093 mol) in methanol (300 ml) was hydrogenated at 30° C. under a 3 bar pressure for 12 hours with Pd/C (5 g) as a catalyst. After uptake of $H_2$ (1 equiv), the catalyst was filtered through celite, washed with $CH_3OH$ and the filtrate was evaporated. The residue was purified by column chromatography over silica gel (eluent: $CH_2Cl_2/CH_3OH/NH_4OH$ 92/8/0.5; 20–45 µm). Two pure fractions were collected and their solvents were evaporated, yielding a residue of 2.8 g (22%) and 9 g (71%). Parts of these fractions (0.6 g; 0.8 g) were crystallized from diethyl ether. The precipitate was filtered off and dried. Yield: 0.52 g of compound (14); mp. 126° C. and 0.53 g of compound (15); mp. 200° C.

EXAMPLE B12

Preparation of (compound 16)

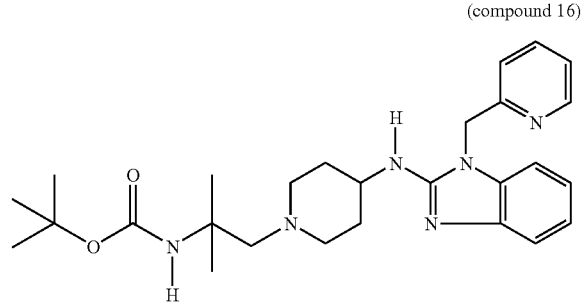

NaBH$_3$CN (0.048 mol) was added portionwise at 5° C. to a solution of N-4-piperidinyl-1-(2-pyridylmethyl)-1H-benzimidazol-2-amine dihydrochloride (0.032 mol) and 1,1-dimethylethyl(1,1-dimethyl-2-oxoethyl)carbamoate (0.032 mol) in methanol (100 ml). The mixture was stirred at room temperature for 8 hours and hydrolized at 5° C. with ice water. Methanol was evaporated. The residue was extracted with $CH_2Cl_2$. The organic layer was separated, dried (MgSO$_4$), filtered and the solvent was evaporated. The residue (13 g) was purified by column chromatography over silica gel (eluent: $CH_2Cl_2/CH_3OH/NH_4OH$ 95/5/0.1; 20–45 µm). The pure fractions were collected and the solvent was evaporated. Yield: 2.2 g of compound (16) (14%).

EXAMPLE B13

Preparation of (compound 17)

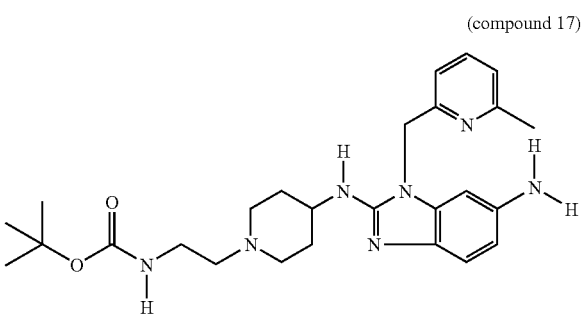

A mixture of 1,1-dimethylethyl[2-[4-[[1-[(6-methyl-2-pyridyl)methyl]-6-nitro-1H-benzimidazol-2-yl]amino]-1-piperidinyl]ethyl]carbamate (0.0084 mol) in methanol (150 ml) was hydrogenated at 50° C. with Pt/C$_5$% (1 g) as a catalyst in the presence of thiophene solution (1 ml). After uptake of $H_2$ (3 equiv), the catalyst was filtered off and the filtrate was evaporated. The residue was purified by column chromatography over silica gel (eluent: $CH_2Cl_2/(CH_3OH/NH_3)$ 99/1 to 97.5/2.5). The pure fractions were collected and the solvent was evaporated. Yield: 3.3 g of compound (17) (82%).

EXAMPLE B14

Preparation of

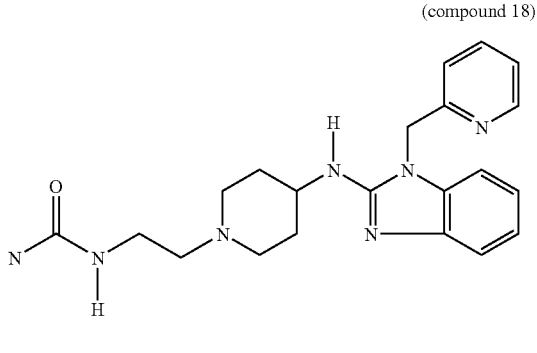

(compound 18)

A mixture of N-[1-(2-aminoethyl)-4-piperidinyl]-1-[(2-pyridyl)methyl]-1H-benzimidazol-2-amine (0.143 mol) in HCOOH (50 ml) was stirred and refluxed for 3 hours. The solvent was evaporated till dryness. The residue was dissolved in $CH_2Cl_2$. The mixture was basified with $Na_2CO_3$, filtered and the filtrate was evaporated till dryness. The residue (4.9 g) was purified by column chromatography over silica gel (eluent: $CH_2Cl_2/CH_3OH/NH_4OH$ 92/8/1; 20–45 μm). The pure fractions were collected and the solvent was evaporated. The residue was crystallized from 2-propanone. The precipitate was filtered off and dried. Yield: 2.8 g of compound (18) (51%); mp. 146° C.

EXAMPLE B15

Preparation of

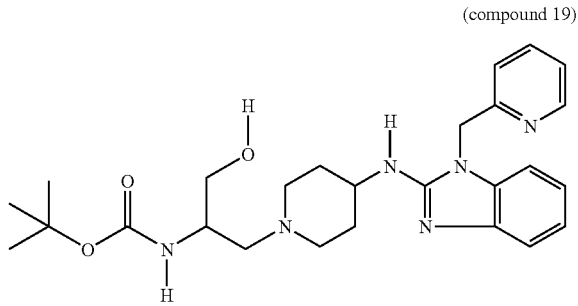

(compound 19)

LiAlH$_4$ (0.0065 mol) was added portionwise at 5° C. to a solution of (±)-1,1-dimethyl-ethyl [1-(methoxycarbonyl)-2-[4-[[1-(2-pyridylmethyl)-1H-benzimidazol-2-yl]amino]-1-piperidinyl]ethyl]carbamate (0.0059 mol) in THF (30 ml). The mixture was stirred at 5° C. for 1 hour. EtOAc was added. The mixture was hydrolized with ice water, filtered over celite and extracted with EtOAc. The organic layer was separated, dried (MgSO$_4$), filtered and the solvent was evaporated. The residue (2.8 g) was purified by column chromatography over silica gel (eluent: $CH_2Cl_2/CH_3OH/NH_4OH$ 92/8/0.5; 15–40 μm). The pure fractions were collected and the solvent was evaporated. Yield: 1.55 g of compound (19) (56%).

EXAMPLE B16 a) Preparation of

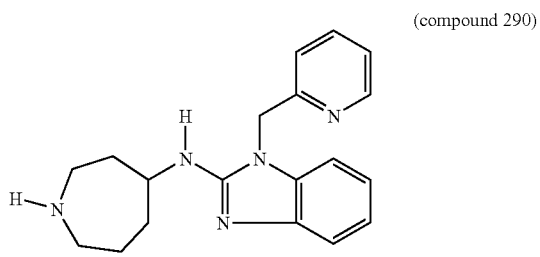

(compound 290)

A mixture of

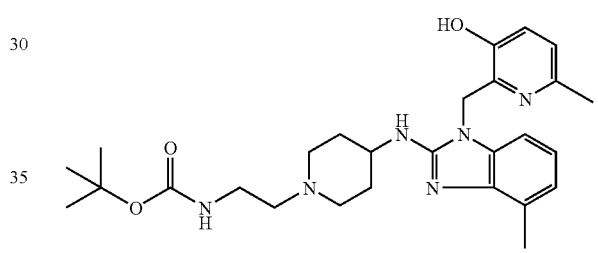

(0.021mol) in 2-propanol/HCl (29 ml) and 2-propanol (290 ml) was stirred and refluxed for 2 hours and then cooled to room temperature. The precipitate was filtered off and combined with analogously obtained fraction. The precipitate was dissolved at reflux in ethanol (150 ml), then allowed to crystallize out. The precipitate was filtered off and dried (45° C., 16 hours, then air-dried for 30 minutes). Yield: 8.9 g (70%) of compound (290). Compound (290) was converted into the free base according to art known procedures resulting in compound (355).

b) Preparation of

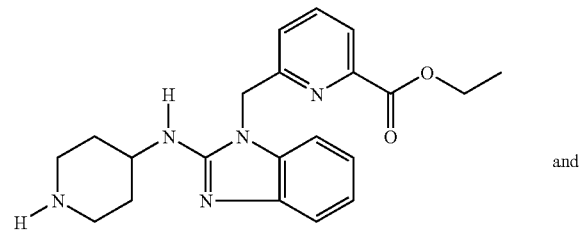

(compound 356)

and preparation of

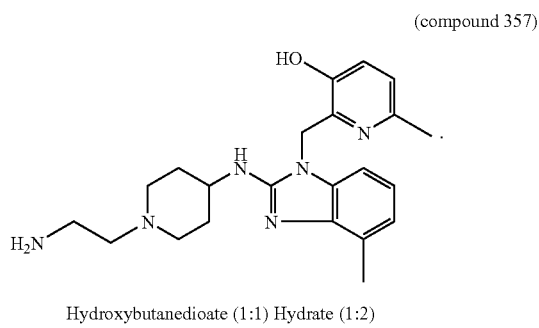

(compound 357)

Hydroxybutanedioate (1:1) Hydrate (1:2)

Compound (355) (0.001 mol) was added to ethanol (6 ml; absolute ethanol) and heated to reflux temperature to give an homogeneous solution (I). Solution (I) was treated with butanedioic acid (0.118 g, 0.001 mol) and resulted in immediate salt formation. The mixture was heated to reflux temperature, became homogeneous, then was allowed to cool to room temperature. The precipitate was filtered off, and dried (vacuum, 50° C., 24 hours). Yield: 0.40 g (78%) of compound (356). Solution (I) was treated with hydroxybutanedioic acid (0.134 g, 0.001 mol) and the mixture was heated to reflux temperature, became homogeneous, then was allowed to cool to room temperature. The precipitate was filtered off and dried (vacuum, 50° C., 24 hours). Yield: 0.46 g (87%) of compound (357).

c) Preparation of

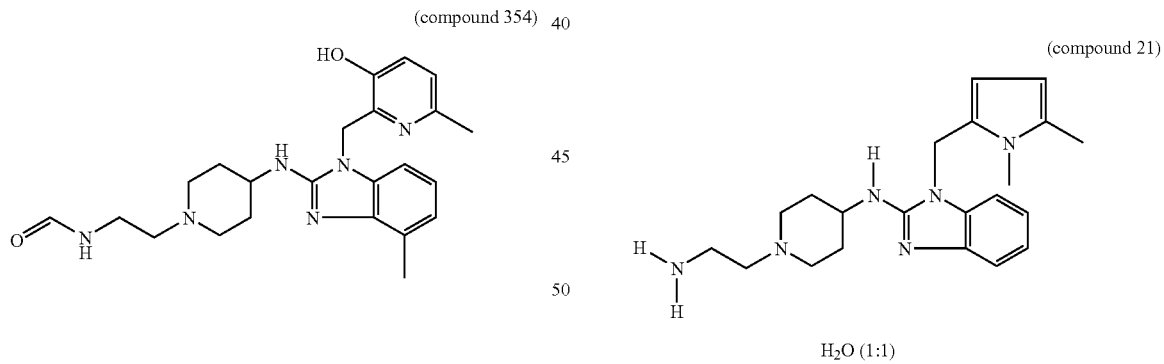

Compound (290) (0.000065 mol) was dissolved in water (3 ml). The mixture was stirred and alkalized with concentrated NH$_4$OH (400 µl, and 100 µl). CHCl$_3$ (20 ml) was added. The mixture was stirred vigorously for 10 minutes. More conc. NH$_4$OH (100 µl) was added and the mixture was stirred vigorously for 5 minutes. The organic layer was separated, then the alkalic layer was re-extracted once with CHCl$_3$ (5 ml). The combined organic layers were washed once with a saturated aqueous NaCl solution, then dried (MgSO$_4$), filtered and the solvent was evaporated. The residue was stirred in HCOOH (20 ml) until complete dissolution (=after 2 minutes). Acetic acid anhydride (0.00213 mol) was added dropwise over 1 minute and the reaction mixture was stirred at room temperature. After 24 hours, more acetic acid anhydride (50 µl) was added and the reaction mixture was stirred for 15 minutes. More acetic acid anhydride (50 µl) was added to the reaction mixture. The whole was stirred for 2 hours 15 minutes on a 60° C. oil-bath, then stood over the weekend at room temperature. More acetic acid anhydride (1000 µl) was added to the reaction mixture. The whole was stirred for 30 minutes on a 60–70° C. oil-bath, then stirred overnight at room temperature. Again, the reaction mixture was stirred for 2.5 hours at 60° C. More acetic acid anhydride (100 µl) was added and the reaction mixture was stirred for 45 minutes at 60° C., then stood overnight at room temperature. Water (100 µl) was added to decompose remaining acetic acid anhydride. The solvent was evaporated (in vacuo at 60° C.). Toluene was added to the residue, then evaporated again (in vacuo, 60° C.). Xylene was added, then evaporated (in vacuo at 60° C.) to give (x). To a sample, water (3 drops) was added. NH$_4$OH (10 µl) was added. Water (5 drops) was added and the mixture was shaken vigorously to give (y). (x) and (y) were dissolved in CH$_2$Cl$_2$/CH$_3$OH/(CH$_3$OH/NH$_3$) 84/12/4, then purified by column chromatography over silica gel (eluent: CH$_2$Cl$_2$/CH$_3$OH/(CH$_3$OH/NH$_3$) 84/12/4). The product fractions were collected and the solvent was evaporated. This fraction (0.185 g) was stirred in boiling ethanol (±10 ml), allowed to cool to room temperature, then Et$_2$O (10 ml) was added and the mixture was stirred for 15 minutes. The precipitate was filtered off by suction, rinsed with Et$_2$O, then air-dried for 3 hours, then dried further (high vacuum, 2 hours at room temperature, then air-dried overnight at room temperature). Yield: 0.153 g of compound (354).

EXAMPLE B17

Preparation of (compound 21)

H$_2$O (1:1)

A mixture of 1,1-dimethylethyl[2-[4-[[1-(1,5-dimethyl-1H-pyrrol-2-yl)-1H-benzimidazol-2-yl]amino]-1-piperidinyl]ethyl]carbamate (0.002 mol) and KOH (1 g) in sec. butanol (25 ml) was stirred and refluxed for 1 hour. The solvent was evaporated. The residue was purified by column chromatography over silica gel (eluent: CH$_2$Cl$_2$/(CH$_3$OH/NH$_3$) 90/10). The pure fractions were collected and the solvent was evaporated. The residue was suspended in DIPE. The precipitate was filtered off and dried. Yield: 0.57 g of compound (21).

EXAMPLE B18

Preparation of

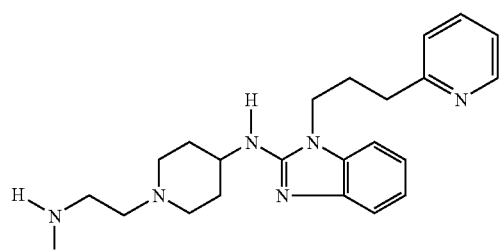
(compound 22)

HCl (1:4); H₂O (1:2)

A mixture of 2-[2-[4-[[1-[3-(2-pyridyl)propyl]-1H-benzimidazol-2-yl]amino]-1-piperidinyl]ethyl]-1H-isoindole-1,3(2H)-dione (0.005 mol) in HCl 6N (120 ml) and HOAc (60 ml) was stirred and refluxed for 30 hours and then cooled on an ice bath. A NaOH solution was added carefully dropwise until pH>7. The mixture was extracted with CH₂Cl₂ and then separated into its layers. The aqueous layer was extracted with CH₂Cl₂. The combined organic layer was washed with H₂O, separated again, dried (MgSO₄), filtered and the solvent was evaporated. The residue was taken up in a small amount of 2-propanol and converted into the hydrochloric acid salt (1:4) with 2-propanol/HCl 6N. DIPE was added. The precipitate was filtered off, washed with DIPE and dried. Yield: 1.95 g of compound (22) (70%).

EXAMPLE B19

Preparation of

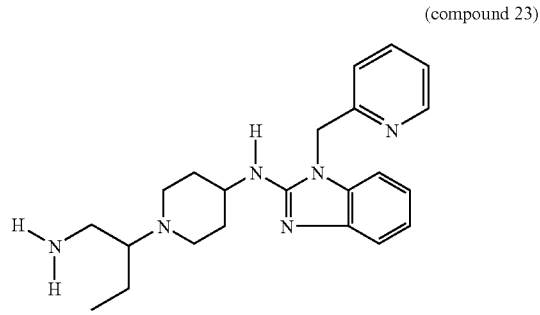
(compound 23)

A mixture of intermediate (17) (0.01 mol) in hydrazine (5 ml) and ethanol (50 ml) was stirred and refluxed for 30 minutes. The solvent was evaporated. The residue was dissolved in CH₂Cl₂. The organic solution was washed with H₂O, dried (MgSO₄), filtered and the solvent was evaporated. The residue (4.8 g) was purified by column chromatography over silica gel (eluent: CH₂Cl₂/CH₃OH/NH₄OH 89/10/1; 15–40 μm). The pure fractions were collected and the solvent was evaporated. The residue was crystallized from diethyl ether. The precipitate was filtered off and dried. Yield: 51.7 g of compound (23) (45%); mp. 112° C.

EXAMPLE B20

Preparation of

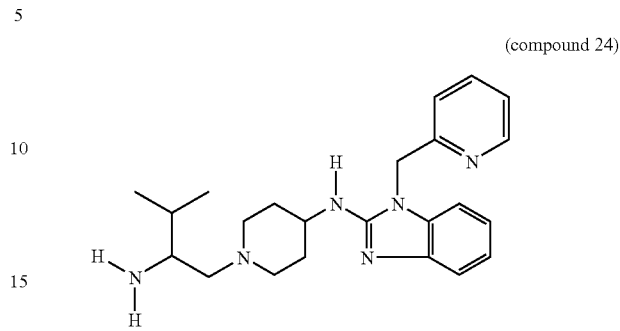
(compound 24)

A mixture of 3-methyl-1-[4-[[1-(2-pyridylmethyl)-1H-benzimidazol-2-yl]amino]-1-piperidinyl]-2-butanone (0.01 mol) and benzenemethanamine (0.031 mol) in methanol (50 ml) was hydrogenated at 40° C. under a 3 bar pressure for 24 hours with Pd/C (0.4 g) as a catalyst. After uptake of H₂ (1 equiv), the catalyst was filtered through celite, washed with CH₃OH and CH₂Cl₂ and the filtrate was evaporated. The residue (5 g) was purified by column chromatography over silica gel (eluent: CH₂Cl₂/CH₃OH/NH₄OH 93/7/1; 15–40 μm). The pure fractions were collected and the solvent was evaporated. The residue was crystallized from pentane. The precipitate was filtered off and dried. Yield: 1 g of compound (24) (21%); mp. 115° C.

EXAMPLE B21

Preparation of

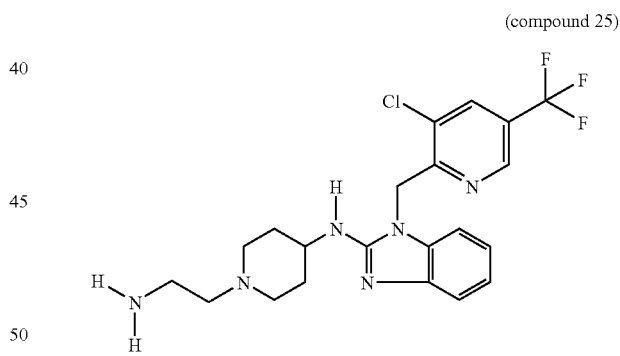
(compound 25)

Reaction under N₂ atmosphere. Na₂CO₃ (0.250 g) was added to 1,1-dimethylethyl [2-[4-(1H-benzimidazol-2-yl amino)-1-piperidinyl]ethyl]carbamate (0.0028 mol) in DMF (10 ml). The mixture was stirred for 4 hours at room temperature. The reaction mixture was divided over 5 tubes. 2-Chloromethyl-3-chloro-5-trifluoropyridine (0.100 g) was added to each tube and the resulting reaction mixture was stirred overnight at 50° C. The mixture was acidified with HCl/2-propanol, then stirred for 3 hours at 90° C. The mixture was alkalized with NH₃/CH₃OH and the desired compound was isolated and purified by high-performance liquid chromatography over a Prochrom D.A.C.—column with Hypersil 'BDS' HS C18 (100 g, 8 μm, 100 Å; eluent gradient: ((0.5% NH₄OAc in H₂O)/CH₃OH/CH₃CN (0 min) 70/15/15, (10.31 min) 0/50/50, (16.32 min) 0/0/100, (16.33 min-end) 70/15/15). The desired fractions were collected and the solvent was evaporated. Yield: 0.020 g of compound (25).

EXAMPLE B22 a) Preparation of (compound 26)

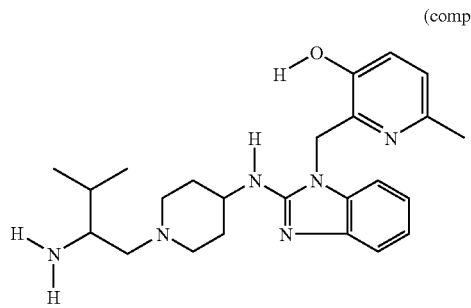

A mixture of 1-[4-[[1-[(3-hydroxy-6-methyl-2-pyridyl)methyl]-1H-benzimidazol-2-yl]-amino]-1-piperidinyl]-3-methyl-2-butanone (0.0065 mol) in CH$_3$OH/NH$_3$ (300 ml) was hydrogenated at room temperature with Rh/Al$_2$O$_3$ (1 g) as a catalyst in the presence of CH$_3$OH/NH$_3$ (3 ml). After uptake of H$_2$ (1 equiv), the catalyst was filtered off and the filtrate was evaporated. The residue was purified over silica gel on a glass filter (eluent: CH$_2$Cl$_2$/(CH$_3$OH/NH$_3$) 95/5 to 90/10). The pure fractions were collected and the solvent was evaporated. Yield: 1.52 g of compound (26) (55%).

b) Preparation of (compound 298)

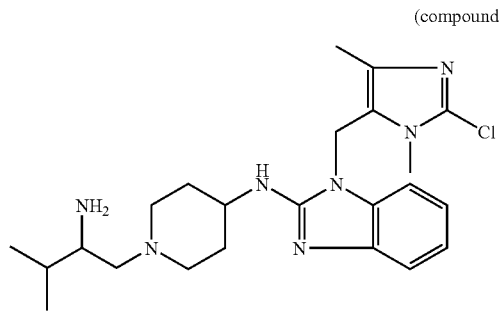

A mixture (0.6 g) of

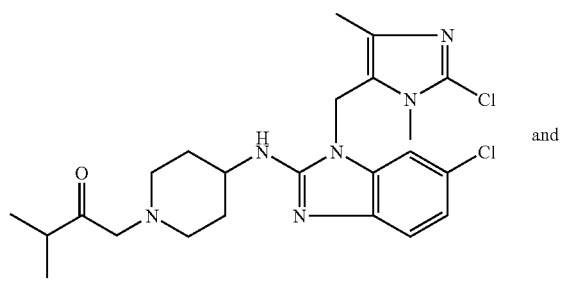

and

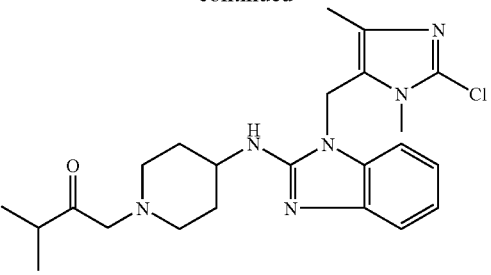

(prepared analogous to the procedure described in example A10 b)) in NH$_3$/CH$_3$OH (100 ml) was hydrogenated for 16 hours at 50° C. with Rh/C (0.5 g) as a catalyst in the presence of thiophene solution (1 ml). After uptake of H$_2$ (1 equiv), the catalyst was filtered off and the filtrate was evaporated. The residue was purified by high-performance liquid chromatography over Kromasil C18 (100 Å; eluent: NH$_4$OAc 0.5% H$_2$O/CH$_3$CN 75%, 25% CH$_3$OH to CH$_3$CN 100%). Two pure fraction groups were collected and their solvent was evaporated. Yield: 0.165 g of compound 298.

EXAMPLE B23

Preparation of (compound 27)

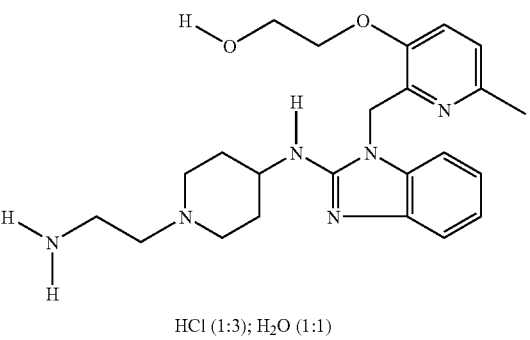

HCl (1:3); H$_2$O (1:1)

A mixture of (±)-1,1,dimethylethyl[2-[4-[[1-[[6-methyl-3-[2-[(tetrahydro-2H-pyran-2-yl)oxy]ethoxy]-2-pyridyl]methyl]-1H-benzimidazol-2-yl]amino]-1-piperidinyl]ethyl]-carbamate (0.0014 mol) in 2-propanol/HCl (5 ml) and 2-propanol (50 ml) was stirred and refluxed for 4 hours and taken up in H$_2$O, Na$_2$CO$_3$ and CH$_2$Cl$_2$. The organic layer was separated. 2-Propanol/HCl (5 ml) and 2-propanol (50 ml) were added again. The mixture was stirred and refluxed for 1 hour and converted into the hydrochloric acid salt. The precipitate was filtered off and dried. The residue was purified over silica gel on a glass filter (eluent: CH$_2$Cl$_2$/(CH$_3$OH/NH$_3$) 90/10). The pure fractions were collected and the solvent was evaporated. The residue was converted into the hydrochloric acid salt. The precipitate was filtered off and dried. Yield: 0.18 g of compound (27) (23%).

EXAMPLE B24

Preparation of (compound 28)

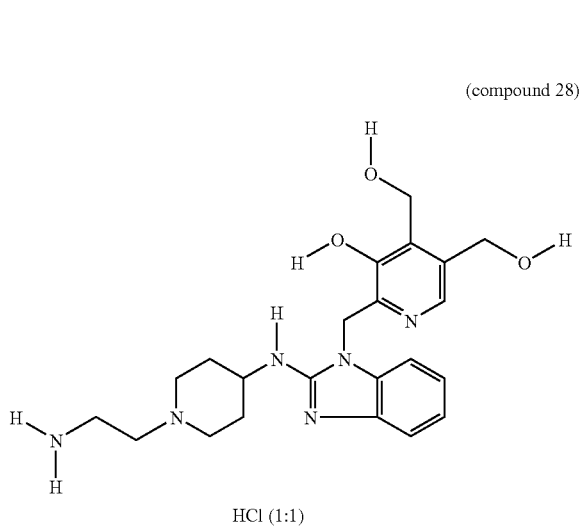

HCl (1:1)

A mixture of 1,1-dimethylethyl[2-[4-[[1-[[3,5-dihydro-3,3-dimethyl-9-(phenyl-methoxy)-1H-[1,3]dioxepino[5,6-c]pyridin-2-yl]methyl]-1H-benzimidazol-2-yl]amino]-1-piperidinyl]ethyl]carbamate (0.00213 mol) in HCl 10N (100 ml) was stirred and refluxed for 4 hours. The solvent was evaporated. The residue was suspended in DIPE. The precipitate was filtered off and dried. Yield: 0.9 g of compound (28).

EXAMPLE B25 a) Preparation of (compound 29)

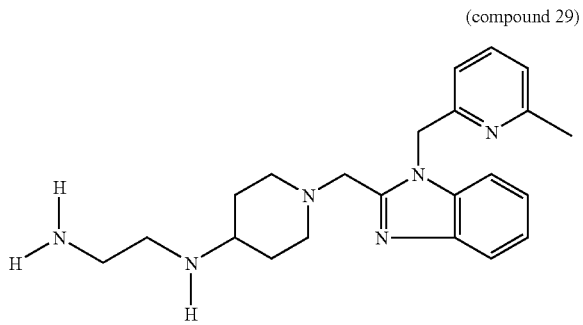

A mixture of intermediate (19) (0.008 mol) in methanol (150 ml) was hydrogenated with Pd/C (1 g) as a catalyst. After uptake of $H_2$ (1 equiv), the catalyst was filtered off and the filtrate was evaporated. The residue was purified over silica gel on a glass filter (eluent: $CH_2Cl_2/(CH_3OH/NH_3)$ 95/5, 93/7 to 90/10). The pure fractions were collected and the solvent was evaporated. Yield: 1.81 g of compound (29) (60%).

b) Preparation of (compound 312)

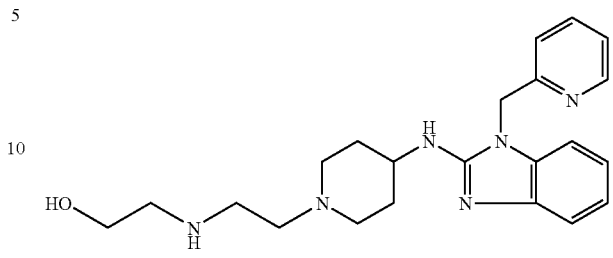

A mixture of intermediate (24) (0.011 mol) in methanol (100 ml) was hydrogenated at room temperature under a 3 bar pressure overnight with Pd/C (2 g) as a catalyst. The catalyst was recuperated and hydrogenation was continued at room temperature under a 3 bar pressure for 2 hours with Pd/C (2 g) as a catalyst. After uptake of hydrogen (1 equiv), the catalyst was filtered off, washed with $CH_3OH$ and $CH_2Cl_2$ and the filtrate was evaporated. The residue (4.5 g) was purified by column chromatography over silica gel (eluent: $CH_2Cl_2/CH_3OH/NH_4OH$ 85/15/1 and 56/40/4; 15–40 μm). The pure fractions were collected and the solvent was evaporated. The residue was crystallized from 2-propanol and diethyl ether. The precipitate was filtered off and dried. Yield: 1.8 g of compound (312) (40%).

c) Preparation of (compound 313)

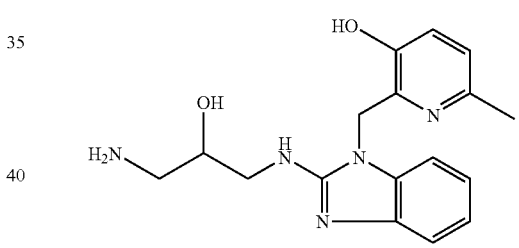

A mixture of

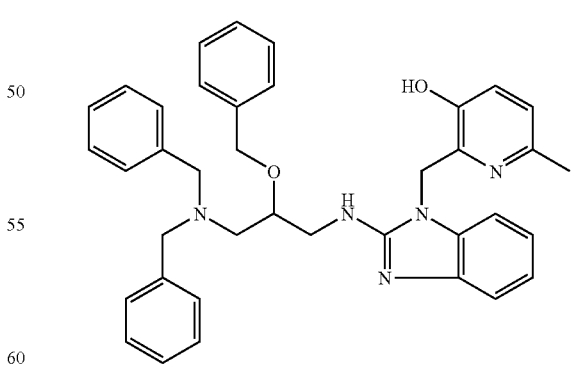

prepared according to A5c), in methanol (250 ml) was hydrogenated with Pd/C 10% (2 g) as a catalyst. After uptake of hydrogen (3 equiv), the catalyst was filtered off and the filtrate was evaporated. The residue was purified by column chromatography over silica gel (eluent: $CH_2Cl_2/$ (CH₃OH/NH₃) 90/10). The product fractions were collected and the solvent was evaporated. Yield: 4.2 g of compound (313).

EXAMPLE B26

Preparation of

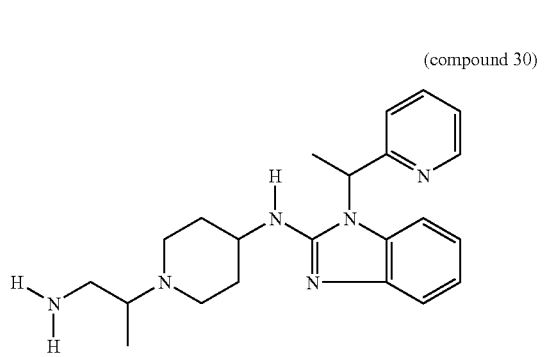

(compound 30)

LiAlH₄ (0.014 mol) was added portionwise at 5° C. to a solution of intermediate (20) (0.012 mol) in THF (50 ml). The mixture was allowed to warm to room temperature and then stirred at room temperature for 48 hours. EtOAc was added. The mixture was hydrolized with ice water, filtered over celite, washed with EtOAc and the filtrate was extracted with EtOAc. The organic layer was separated, dried (MgSO₄), filtered and the solvent was evaporated. The residue (3 g) was purified by column chromatography over silica gel (eluent: CH₂Cl₂/CH₃OH(NH₄OH 87/13/1; 15–40 μm). The pure fractions were collected and the solvent was evaporated. The residue was crystallized from DIPE. The precipitate was filtered off and dried. Yield: 0.75 g of compound (30) (16%); mp. 85° C.

EXAMPLE B27 a) Preparation of

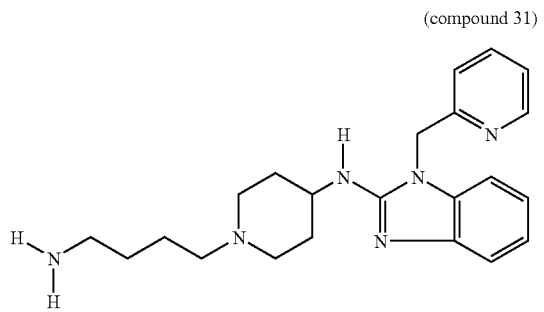

(compound 31)

A mixture of 4-[[1-(2-pyridylmethyl)-1H-benzimidazol-2-yl]amino]-1-piperidine-butanenitrile (0.01 mol) in CH₃OH/NH₃ (80 ml) was hydrogenated at room temperature under a 3 bar pressure overnight with Raney Nickel (3.8 g) as a catalyst. After uptake of H₂ (2 equiv), the catalyst was filtered through celite and the filtrate was evaporated. The residue was crystallized from diethyl ether. The precipitate was filtered off and dried. Yield: 2.9 g of compound (31) (76%); mp. 94° C.

b) Preparation of

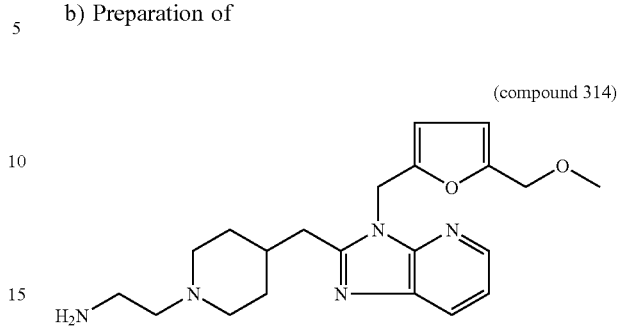

(compound 314)

A mixture of 5-[[2-[[1-(2-aminoethyl)-4-piperidinyl]methyl]-3H-imidazo[4,5-b]-pyridin-3-yl]methyl]-2-furanmethanol (0.0068 mol) in CH₃OH/NH₃ (300 ml) was hydrogenated at 20° C. with Raney Nickel (1 g) as a catalyst. After uptake of H₂ (2 equiv), the catalyst was filtered off and the filtrate was evaporated. The residue was purified by column chromatography over silica gel (eluent: CH₂Cl₂/(CH₃OH/NH₃) from 95/5 to 90/10). The desired fractions were collected and the solvent was evaporated. The residue was repurified by column chromatography over silica gel (eluent: CH₂Cl₂/(CH₃OH/NH₃) 95/5). The purest fractions were collected and the solvent was evaporated. The residue was taken up into HCl/2-propanol and DIPE was added. The resulting salt was filtered off and purified by column chromatography over silica gel (eluent: CH₂Cl₂/(CH₃OH/NH₃) 98/2). The pure fractions were collected and the solvent was evaporated. Yield: 0.2 g of compound (314).

EXAMPLE B28

Preparation of

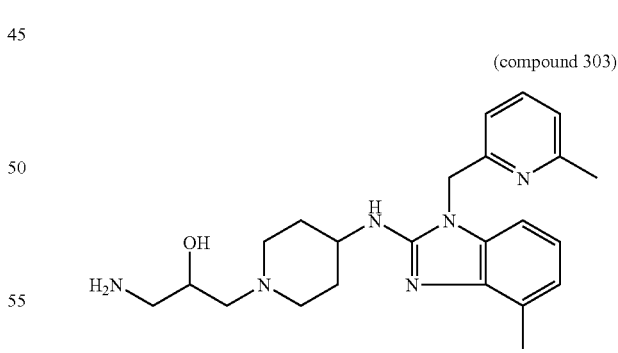

(compound 303)

A mixture of intermediate 21 (0.001 mol) in CH₃OH/NH₃ (100 ml) was stirred at room temperature for 20 hours and at 100° C. for 16 hours. The solvent was evaporated. The residue was purified by column chromatography over silica gel (eluent: CH₂Cl₂/(CH₃OH/NH₃) 90/10). The pure fractions were collected and the solvent was evaporated. The residue was dried. Yield: 0.11 g of compound 303.

EXAMPLE B29

Preparation of (compound 315)

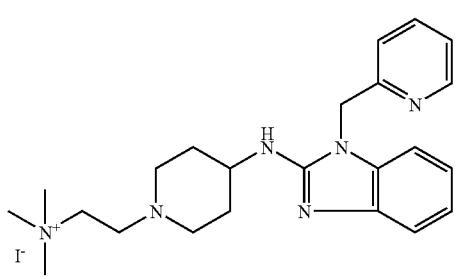

Iodomethane (0.00494 mol) was added at room temperature to a solution of compound (328) (0.004491 mol) in 2-propanone (17 ml), and the reaction mixture was stirred at room temperature for 1 hour. The precipitate was filtered off and dried. The residue (1.6 g) was crystallized from 2-propanone. The precipitate was filtered off and dried. Yield: 1.5 g of compound (315) (64%).

EXAMPLE B30

Preparation of (compound 316)

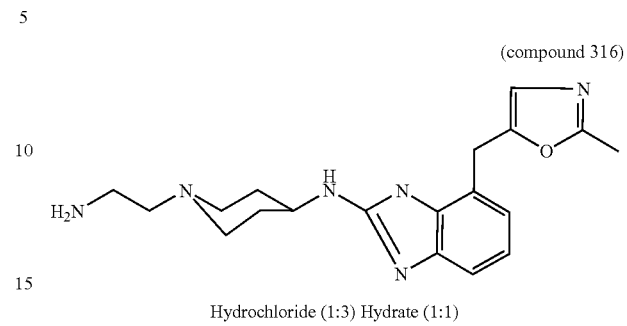

Hydrochloride (1:3) Hydrate (1:1)

Compound (317) (0.0027 mol) was dissolved in ethanol (50 ml). The mixture was converted into the hydrochloric acid salt (1:3) with 2-propanol/HCl. The precipitate was filtered off and dried. Yield: 1.68 g of compound (316).

Tables 1 to 17 list the compounds of formula (I') and the compounds of group (I") which were prepared according to one of the above examples.

TABLE 1

| Co. No. | Ex. No. | n | $R^a$ | $R^b$ | Physical data |
|---|---|---|---|---|---|
| 32 | B1a | 1 | H | 1,4-dimethyl-1H-imidazol-5-yl | $H_2O$ (1:2) |
| 33 | B1a | 1 | H | 1,4-dimethyl-5-[-$COOC_2H_5$]-1H-imidazol-2-yl | HCl (1:3) |
| 34 | B1a | 1 | H | 2-bromo-5-pyridyl | |
| 35 | B1a | 1 | $CH_3$ | 2-pyrazinyl | |
| 36 | B1a | 1 | ethyl | 2-pyrazinyl | |
| 37 | B1a | 1 | H | 2-pyridyl | HCl (1:2); mp. >160° C. |
| 38 | B1a | 1 | $CH_3$ | 2-pyridyl | |
| 39 | B1a | 2 | H | 2-pyridyl | HCl (1:3); $H_2O$ (1:2) |
| 40 | B1b | 2 | H | 2-pyridyl | |
| 41 | B1b | 3 | H | 2-pyridyl | HBr (1:3) |
| 42 | B1a | 0 | — | 2-pyrimidinyl | |
| 43 | B1a | 1 | H | 2-pyrimidinyl | HCl (1:3); $H_2O$ (1:1) |
| 44 | B1a | 1 | H | 3,5,6-trimethyl-2-pyrazinyl | |
| 45 | B1a | 1 | H | 3-[$C_2H_5$—O—($CH_2$)$_2$—O]-6-methyl-2-pyridyl | HCl (1:3); $H_2O$ (1:3) |
| 46 | B1a | 1 | H | 3-amino-2-pyridyl | HCl (1:3); $H_2O$ (1:2) |
| 47 | B1a | 1 | H | 3-amino-2-pyridyl | |
| 48 | B1a | 1 | H | 3-hydroxy-2-pyridyl | HCl (1:3); $H_2O$ (1:1) |
| 49 | B1a | 1 | H | 3-hydroxy-6-methyl-2-pyridyl | HCl (1:3); $H_2O$ (1:3) |
| 50 | B1a | 1 | H | 3-hydroxy-6-pyridazinyl | HCl (1:2); $H_2O$ (1:1) |
| 51 | B1a | 1 | H | 3-methoxy-6-methyl-2-pyridyl | HCl (1:3); $H_2O$ (1:2) |
| 52 | B1a | 1 | H | 3-methoxy-6-methyl-2-pyridyl | |
| 53 | B1a | 1 | H | 3-methyl-2-pyrazinyl | |

TABLE 1-continued

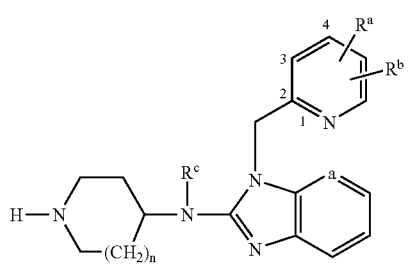

| Co. No. | Ex. No. | n | R^a | R^b | Physical data |
|---|---|---|---|---|---|
| 3 | B2b | 1 | H | 3-OH-4,5-(-$CH_2$—OH)$_2$-2-pyridyl | HCl (1:3); $H_2O$ (1:2) |
| 54 | B1a | 1 | H | 3-pyridazinyl | |
| 55 | B3 | 1 | H | 1,5-($CH_3$)$_2$-1H-pyrrol-2-yl | |
| 56 | B1a | 1 | H | 4,6-dimethyl-2-pyridyl | |
| 57 | B1a | 1 | H | 4-chloro-2-pyridyl | |
| 58 | B1a | 1 | H | 4-methoxy-2-pyridyl | |
| 59 | B1a | 1 | H | 4-methyl-1H-imidazol-5-yl | HCl (1:3); $H_2O$ (1:1) |
| 60 | B1a | 1 | H | 4-pyridyl | HCl (1:3); $H_2O$ (1:1) |
| 61 | B1a | 1 | H | 4-pyridyl | |
| 62 | B1a | 1 | H | 4-pyrimidinyl | |
| 63 | B1a | 1 | H | 5-chloro-1-methyl-1H-imidazol-2-yl | |
| 64 | B1a | 1 | H | 5-methyl-2-pyrazinyl | HCl (1:1) |
| 65 | B1a | 1 | H | 5-methyl-2-pyrazinyl | |
| 66 | B1a | 1 | H | 6-(-$CH_2$—O—$CH_3$)-2-pyridyl | HCl (1:2); $H_2O$ (1:3) |
| 67 | B1a | 1 | H | 6-(hydroxymethyl)-2-pyridyl | |
| 68 | B1a | 1 | H | 6-[-CO—N($CH_3$)$_2$]-2-pyridyl | |
| 69 | B1a | 1 | H | 6-bromo-2-pyridyl | HCl (1:2) |
| 70 | B1a | 1 | H | 6-bromo-2-pyridyl | |
| 71 | B1a | 1 | H | 6-chloro-2-pyridyl | HCl (1:2) |
| 72 | B1a | 1 | H | 6-HOOC-2-pyridyl | |
| 73 | B1a | 1 | $CH_3$ | 6-hydroxymethyl-2-pyridyl | HCl (1:3); $H_2O$ (1:1) |
| 74 | B1a | 1 | H | 6-methoxy-2-pyridyl | |
| 1 | B1a | 1 | H | 6-methyl-2-pyrazinyl | |
| 75 | B1a | 1 | $CH_3$ | 6-methyl-2-pyrazinyl | |
| 2 | B2a | 1 | H | 6-methyl-3-[-O—($CH_2$)$_2$—OH]-2-pyridyl | HCl (1:3); $H_2O$ (1:2) |
| 76 | B1a | 1 | H | 6-methyl-3-[-O—($CH_2$)$_2$—N($CH_3$)$_2$]-2-pyridyl | HCl (1:4); $H_2O$ (1:1) |
| 7 | B6 | 1 | H | 6-(-$COOC_2H_5$)-2-pyridyl | |

TABLE 2

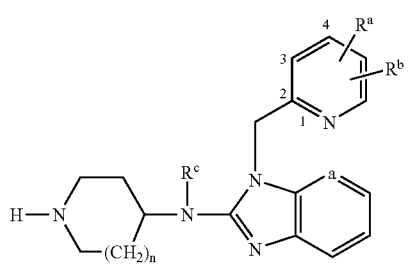

| Co. No. | Ex. No. | n | a | R^a | R^b | R^c | Physical data |
|---|---|---|---|---|---|---|---|
| 78 | B1a | 1 | CH | H | H | $CH_3$ | — |
| 4 | B3 | 2 | CH | H | H | H | — |

TABLE 2-continued

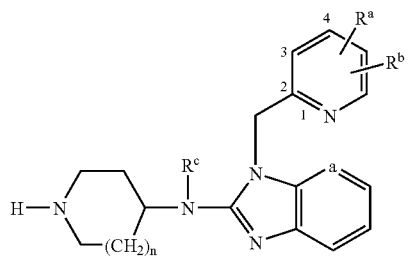

| Co. No. | Ex. No. | n | a | R^a | R^b | R^c | Physical data |
|---|---|---|---|---|---|---|---|
| 81 | B16 | 1 | CH | H | H | —$CH_2$-phenyl | — |
| 308 | B1b | 1 | N | 3-OH | 6-$CH_3$ | H | — |

TABLE 3

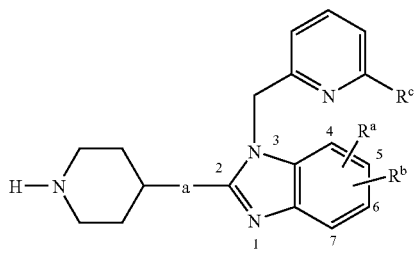

| Co. No. | Ex. No. | a | $R^a$ | $R^b$ | $R^c$ | Physical data |
|---|---|---|---|---|---|---|
| 82 | B4 | $CH_2$ | 5-$OCH_3$ | 6-$OCH_3$ | H | |
| 83 | B1b | NH | 5-Cl | 6-Cl | $CH_3$ | HBr (1:3) |
| 84 | B1b | NH | 5-$CH_3$ | 6-$CH_3$ | $CH_3$ | HBr (1:3) |
| 85 | B1b | NH | 4-Cl | H | $CH_3$ | HBr (1:3) |
| 86 | B1b | NH | 7-Cl | H | $CH_3$ | HBr (1:3); $H_2O$ (1:1) |
| 87 | B1b | NH | 6-$NO_2$ | H | $CH_3$ | HBr (1:3); $H_2O$ (1:1) |
| 88 | B1b | NH | 7-$CH_3$ | H | $CH_3$ | HBr (1:3) |
| 89 | B1b | NH | 5-$NO_2$ | H | $CH_3$ | HBr (1:3); $H_2O$ (1:1) |
| 90 | B1b | NH | 7-$CH_3$ | H | $CH_3$ | |
| 91 | B1b | NH | 4-$CH_3$ | H | $CH_3$ | HBr (1:3) |
| 92 | B1b | NH | 4-$CH_3$ | H | $CH_3$ | |
| 93 | B1b | NH | 5-$CF_3$ | H | $CH_3$ | |
| 94 | B1b | NH | 6-$CF_3$ | H | $CH_3$ | |
| 95 | B1b | NH | 6-Cl | H | $CH_3$ | |
| 96 | B1b | NH | 5-Cl | H | $CH_3$ | |
| 5 | B4 | NH | 6-(-$COOC_2H_5$) | H | $CH_3$ | |
| 97 | B4 | NH | 6-(-$COOC_2H_5$) | H | $CH_3$ | HCl (1:3); $H_2O$ (1:1) |
| 98 | B4 | NH | 6-(-$CH_2$—OH) | H | $CH_3$ | HCl (1:3); $H_2O$ (1:2) |
| 99 | B4 | NH | 6-(-$CH_2$—OH) | H | $CH_3$ | |
| 100 | B1a | $CH[N(CH_3)_2]$ | H | H | $CH_3$ | HCl (1:4); $H_2O$ (1:1) |

TABLE 4

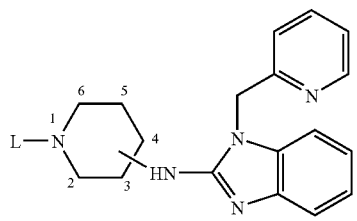

| Co. No. | Ex. No. | * | L | Physical data |
|---|---|---|---|---|
| 101 | B4 | 4 | 3-piperidinyl | HCl (1:4); $H_2O$ (1:2) |
| 102 | B4 | 3 | H | |
| 18 | B14 | 4 | —$(CH_2)_2$—NH—CHO | mp. 146° C. |
| 103 | B7 | 4 | $H_3C$—C($CH_3$)($CH_3$)—O—C(=O)—NH—cyclopropyl—$CH_2$— | |
| 104 | B16 | 4 | $H_2N$—cyclopropyl—$CH_2$— | HCl (1:4); $H_2O$ (1:2); mp. 226° C. |
| 105 | B16 | 4 | —$CH_2$—$C(CH_3)_2$—$NH_2$ | HCl (1:3); $H_2O$ (1:2); mp. 195° C. |
| 106 | B16 | 4 | —$CH_2$—$CH(CH_2OH)$—$NH_2$ | HCl (1:4); $H_2O$ (1:2); mp. 200° C. |
| 23 | B19 | 4 | —$CH(C_2H_5)$—$CH_2$—$NH_2$ | mp. 112° C. |
| 107 | B19 | 4 | —$CH(C_6H_5)$—$CH(C_6H_5)$—$NH_2$ | (A); mp. 106° C. |
| 108 | B19 | 4 | —$CH(C_6H_5)$—$CH(C_6H_5)$—$NH_2$ | (B); mp. 98° C. |
| 109 | B19 | 4 | 2-aminocyclohexyl | mp. 116° C. |
| 110 | B19 | 4 | —CH(phenylmethyl)—$CH_2$—$NH_2$ | mp. 168° C. |
| 111 | B19 | 4 | —$CH[C(CH_3)_3]$—$CH_2$—$NH_2$ | mp. 133° C. |
| 112 | B19 | 4 | —$CH[CH_2$—$N(CH_3)_2]$—$CH_2$—$NH_2$ | mp. 112° C. |

TABLE 4-continued

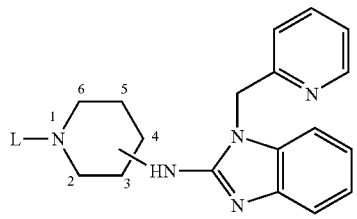

| Co. No. | Ex. No. | * | L | Physical data |
|---|---|---|---|---|
| 113 | B19 | 4 | —CH$_2$—CH(NH$_2$)-phenyl | mp. 128° C. |
| 114 | B19 | 4 | —CH[CH$_2$—(1-piperidinyl)]—CH$_2$—NH$_2$ | HCl (1:4); mp. 203° C. |
| 115 | B19 | 4 | —CH$_2$—CH(cyclopropyl)-NH$_2$ | H$_2$O (1:2); mp. 84° C. |
| 24 | B20 | 4 | —CH$_2$—CH[CH(CH$_3$)$_2$]—NH$_2$ | mp. 115° C. |
| 116 | B20 | 4 | —CH$_2$—CH(CH$_3$)—NH$_2$ | H$_2$O (1:1) |
| 117 | B20 | 4 | —CH(CH$_3$)—CH(CH$_3$)—NH$_2$ | (B); mp. 114° C. |
| 118 | B20 | 4 | —CH$_2$—CH(C$_2$H$_5$)—NH$_2$ | mp. 140° C. |
| 119 | B20 | 4 | —CH$_2$—CH(cycloC$_6$H$_{11}$)—NH$_2$ | mp. 134° C. |
| 120 | B20 | 4 | —(CH$_3$)—CH(CH$_3$)—NH$_2$ | (A); HCl (1:4); H$_2$O (1:4); mp. 214° C. |
| 121 | B20 | 4 | —CH$_2$—CH(NH$_2$)—CH$_2$—CH(CH$_3$)$_2$ | mp. 124° C. |
| 122 | B20 | 4 | —CH$_2$—CH(NH$_2$)—(CH$_2$)$_3$—CH$_3$ | mp. 142° C. |
| 123 | B20 | 4 | —CH$_2$—CH(NH$_2$)—(CH$_2$)$_2$—CH(CH$_3$) | mp. 152° C. |
| 124 | B20 | 4 | —CH$_2$—CH(NH$_2$)—(CH$_2$)$_2$—CH$_3$ | mp. 146° C. |
| 125 | B20 | 4 | —CH$_2$—CH(NH$_2$)—(CH$_2$)$_7$—CH$_3$ | mp. 136° C. |
| 126 | B20 | 4 | —CH$_2$—CH(NH$_2$)—(CH$_2$)$_2$-phenyl | mp. 136° C. |
| 127 | B20 | 4 | —CH$_2$—CH(NH$_2$)—CH$_2$—C(CH$_3$)$_3$ | HCl (1:4); H$_2$O (1:1); mp. 244° C. |
| 128 | B20 | 4 | —CH$_2$—CH(NH$_2$)—CH(CH$_3$)(C$_2$H$_5$) | (A); H$_2$O (1:1); mp. 80° C. |
| 129 | B20 | 4 | —CH$_2$—CH(NH$_2$)—CH(CH$_3$)(C$_2$H$_5$) | (B); mp. 90° C. |
| 130 | B20 | 4 | —CH$_2$—CH(NH$_2$)—(CH$_2$)$_2$—(4-methoxyphenyl) | mp. 100° C. |
| 131 | B1a | 4 | —CH$_2$—CH(NH$_2$)-(4-piperidinyl) | HCl (1:5); H$_2$O (1:1); mp. 269° C. |
| 31 | B27a | 4 | —(CH$_2$)$_4$—NH$_2$ | mp. 94° C. |
| 132 | B27a | 4 | —CH(CH$_3$)—CH$_2$—NH$_2$ | mp. 142° C. |
| 133 | B27a | 3 | —(CH$_2$)$_2$—NH$_2$ | H$_2$O (1:1); mp. 90° C. |
| 134 | B16 | 4 | —(CH$_2$)$_3$—NH$_2$ | HCl (1:4); H$_2$O (1:1); mp. >250° C. |
| 328 | B7 | 4 | —(CH$_2$)$_2$—N(CH$_3$)$_2$ | — |
| 327 | B7 | 4 | —(CH$_2$)$_2$—N(CH$_3$)$_2$ | HCl (1:4); H$_2$O (1:3); mp. 180° C. |

* = position piperidinyl
(A) indicates the first isolated stereoisomeric form
(B) indicates the second isolated stereoisomeric form

TABLE 5

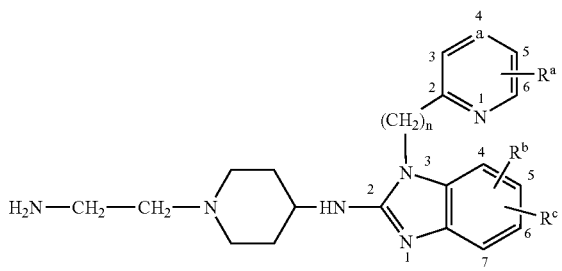

| Co. No. | Ex. No. | n | a | R$^a$ | R$^b$ | R$^c$ | Physical data |
|---|---|---|---|---|---|---|---|
| 135 | B1a | 1 | CH | 6-[-COOCH(CH$_3$)$_2$] | H | H | |
| 136 | B1a | 1 | CH | 6-[-COOC$_2$H$_5$] | H | H | |
| 137 | B16 | 1 | CH | 6-CH$_2$OH | H | H | |
| 138 | B16 | 1 | CH | 6-CH$_3$ | 5-Cl | 6-Cl | HCl (1:4); H$_2$O (1:1) |
| 139 | B16 | 1 | N | 3-CH$_3$ | H | H | HCl (1:3); H$_2$O (1:1) |
| 20 | B16 | 1 | N | 6-CH$_3$ | H | H | HCl (1:3); H$_2$O (1:2) |
| 140 | B16 | 1 | N | 5-CH$_3$ | H | H | HCl (1:4); H$_2$O (1:2) |
| 141 | B16 | 2 | CH | H | H | H | HCl (1:4); H$_2$O (1:1) |
| 142 | B16 | 1 | CH | 6-CH$_3$ | 5-CH$_3$ | 6-CH$_3$ | HCl (1:4); H$_2$O (1:2); 2-propanolate (1:1) |
| 143 | B16 | 1 | CH | 6-CH$_3$ | 4-Cl | H | HCl (1:4); H$_2$O (1:2) |
| 144 | B16 | 1 | CH | 6-CH$_3$ | 7-Cl | H | HCl (1:4); H$_2$O (1:2) |

TABLE 5-continued

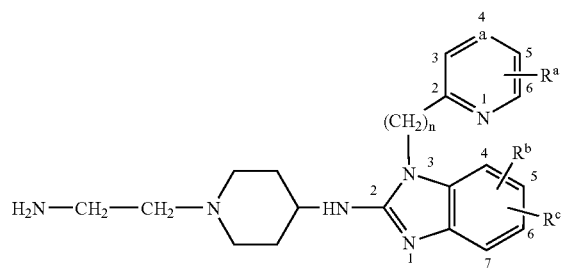

| Co. No. | Ex. No. | n | a | $R^a$ | $R^b$ | $R^c$ | Physical data |
|---|---|---|---|---|---|---|---|
| 145 | B16 | 1 | CH | 6-$CH_3$ | 6-$NO_2$ | H | HCl (1:4); $H_2O$ (1:3) |
| 146 | B16 | 1 | CH | 6-$CH_3$ | 6-$NH_2$ | H | HCl (1:5); $H_2O$ (1:2) |
| 147 | B16 | 1 | CH | 6-$CH_3$ | 5-$NO_2$ | H | HCl (1:4); $H_2O$ (1:1) |
| 148 | B16 | 1 | CH | 6-$CH_3$ | 5-$NH_2$ | H | HCl (1:5); $H_2O$ (1:1) |
| 149 | B16 | 1 | CH | 6-$CH_3$ | 7-$CH_3$ | H | |
| 151 | B16 | 1 | CH | 6-Cl | H | H | |
| 153 | B16 | 1 | CH | 6-Br | H | H | |
| 154 | B16 | 1 | CH | 6-OH | H | H | |
| 155 | B16 | 1 | CH | 6-$OCH_3$ | H | H | |
| 156 | B16 | 1 | CH | 4-Cl | H | H | HCl (1:4); $H_2O$ (1:1) |
| 157 | B16 | 1 | CH | 4-$OCH_3$ | H | H | HCl (1:4); $H_2O$ (1:2); 2-propanolate (1:1) |
| 158 | B16 | 1 | CH | 6-$CH_2OCH_3$ | H | H | HCl (1:4); $H_2O$ (1:2) |
| 159 | B16 | 1 | N | 5-$COOC_2H_5$ | H | H | HCl (1:3); $H_2O$ (1:1) |
| 160 | B16 | 1 | CH | 6-$CH_3$ | 4-$CH_3$ | H | HCl (1:4); $H_2O$ (1:2) |
| 161 | B16 | 1 | CH | 6-$CH_3$ | 6-$COOC_2H_5$ | H | HCl (1:4); $H_2O$ (1:1) |
| 162 | B16 | 1 | CH | 6-$CH_3$ | 6-$CH_2OH$ | H | $H_2O$ (1:1) |
| 163 | B16 | 1 | CH | 6-$CH_3$ | 5-$CF_3$ | H | HCl (1:4); $H_2O$ (1:2) |
| 164 | B16 | 1 | CH | 6-$CH_3$ | 6-$CF_3$ | H | HCl (1:4); $H_2O$ (1:1) |
| 165 | B16 | 1 | CH | 6-$CON(CH_3)_2$ | H | H | HCl (1:3); $H_2O$ (1:2) |
| 166 | B16 | 1 | CH | 6-$CH_3$ | 5-Cl | H | HCl (1:4); $H_2O$ (1:2) |
| 22 | B18 | 3 | CH | H | H | H | HCl (1:4); $H_2O$ (1:2) |
| 167 | B27a | 1 | CH | 6-$CH_3$ | H | H | |
| 305 | B16 | 1 | CH | 6-$CH_3$ | 5-$CH_3$ | H | — |
| 306 | B16 | 1 | CH | 6-$CH_3$ | 6-Cl | H | HCl (1:4) |

TABLE 6

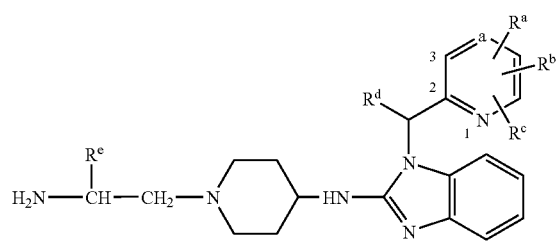

| Co. No. | Ex. No. | a | $R^a$ | $R^b$ | $R^c$ | $R^d$ | $R^e$ | Physical data |
|---|---|---|---|---|---|---|---|---|
| 168 | B27a | CH | 3-OH | H | H | H | H | — |
| 169 | B1a | C | 3-[-O—$(CH_2)_2$—$N(CH_3)_2$] | 6-$CH_3$ | H | H | H | HCl (1:5); $H_2O$ (1:2) |
| 152 | B16 | CH | H | H | H | $CH_3$ | H | HCl (1:4); $H_2O$ (1:3) |
| 170 | B20 | CH | 3-$NH_2$ | H | H | H | $CH(CH_3)_2$ | HCl (1:4); $H_2O$ (1:3) |
| 171 | B20 | N | 5-$CH_3$ | H | H | H | $CH_3$ | mp. 175° C. |
| 172 | B20 | N | 6-$CH_3$ | H | H | H | $CH_3$ | mp. 126° C. |
| 173 | B20 | N | 3-$CH_3$ | 5-$CH_3$ | 6-$CH_3$ | H | $CH_3$ | HCl (1:4); $H_2O$ (1:3); mp. 208° C. |
| 174 | B20 | N | 3-$CH_3$ | 5-$CH_3$ | 6-$CH_3$ | H | $CH(CH_3)_2$ | mp. 124° C. |
| 175 | B16 | N | H | H | H | $CH_3$ | H | HCl (1:3) |
| 176 | B16 | N | 3-$CH_3$ | 5-$CH_3$ | 6-$CH_3$ | H | H | HCl (1:4); $H_2O$ (1:1); 2-propanolate (1:1) |
| 177 | B16 | N | H | H | H | ethyl | H | HCl (1:3); $H_2O$ (1:1) |
| 178 | B16 | N | 6-$CH_3$ | H | H | $CH_3$ | H | HCl (1:3); $H_2O$ (1:1) |
| 179 | B16 | CH | 4-$CH_3$ | 6-$CH_3$ | H | H | H | HCl (1:4); $H_2O$ (1:2) |
| 180 | B16 | CH | 6-Cl | H | H | $CH_3$ | H | HCl (1:3); $H_2O$ (1:1) |
| 181 | B16 | CH | 3-OH | 6-$CH_3$ | H | H | H | HCl (1:3); $H_2O$ (1:2) |

TABLE 6-continued

| Co. No. | Ex. No. | a | R$^a$ | R$^b$ | R$^c$ | R$^d$ | R$^e$ | Physical data |
|---|---|---|---|---|---|---|---|---|
| 182 | B16 | CH | 3-OCH$_3$ | 6-CH$_3$ | H | H | H | |
| 183 | B16 | C | 6-CH$_2$OH | H | H | CH$_3$ | H | HCl (1:4); H$_2$O (1:1) |
| 184 | B16 | C | 3-[O-(CH$_2$)$_2$—OC$_2$H$_5$ | 6-CH$_3$ | H | H | H | HCl (1:4); H$_2$O (1:2) |
| 185 | B16 | CH | 3-OCH$_2$CH$_2$Cl | 6-CH$_3$ | H | H | H | HCl (1:3); H$_2$O (1:2) |
| 186 | B20 | CH | H | H | H | CH$_3$ | CH$_3$ | HCl (1:3); H$_2$O (1:3); mp. 170° C. |
| 187 | B20 | N | 6-CH$_3$ | H | H | H | CH(CH$_3$)$_2$ | HCl (1:3); H$_2$O (1:3); mp. 200° C. |
| 188 | B20 | CH | H | H | H | CH$_3$ | CH(CH$_3$)$_2$ | mp. 233° C. |
| 189 | B20 | N | 5-CH$_3$ | H | H | H | CH(CH$_3$)$_2$ | mp. 114° C. |
| 190 | B20 | CH | H | H | H | H | CH(CH$_3$)$_2$ | mp. 50° C. |
| 25 | B21 | CH | 3-Cl | 5-CF$_3$ | H | H | H | |
| 26 | B22a | CH | 3-OH | 6-CH$_3$ | H | H | CH(CH$_3$)$_2$ | |
| 27 | B23 | CH | 3-O—(CH$_2$)$_2$—OH | 6-CH$_3$ | H | H | H | HCl (1:3); H$_2$O (1:1) |
| 28 | B24 | CH | 4-CH$_2$OH | 3-OH | 5-CH$_2$OH | H | H | HCl (1:1) |
| 192 | B27a | CH | 6-CH$_3$ | H | H | CH$_3$ | H | |
| 299 | B16 | CH | 3-CN | H | H | H | H | mp. 142° C. |
| 300 | B20 | CH | 4-OCH$_3$ | 3-OCH$_3$ | H | H | CH(CH$_3$)$_2$ | HCl (1:4); H$_2$O (1:2); mp. 210° C. |
| 301 | B16 | CH | 3-NH-SO$_2$-phenyl | 6-Cl | H | H | H | mp. 161° C. |
| 307 | B20 | CH | 5-OCH$_3$ | 6-OCH$_3$ | H | H | CH(CH$_3$)$_2$ | C$_2$H$_2$O$_4$ (2:7); mp. 90° C. |

TABLE 7

| Co. No. | Ex. No. | n | * | a | R$^a$ | R$^b$ | R$^c$ | R$^d$ | Physical data |
|---|---|---|---|---|---|---|---|---|---|
| 193 | B16 | 2 | 2 | CH$_2$ | H | H | H | H | ethanedioate (1:3); H$_2$O (1:2); mp. 125° C. |
| 194 | B22b | 1 | 2 | NH | Cl | H | 6-CH$_3$ | CH(CH$_3$)$_2$ | |
| 195 | B22b | 1 | 2 | NH | H | 7-CH$_3$ | 6-CH$_3$ | CH(CH$_3$)$_2$ | |
| 196 | B16 | 2 | 2 | NH | H | H | H | H | ethanedioate (2:7); H$_2$O (1:2); mp. 170° C. |
| 197 | B16 | 1 | 2 | N(CH$_3$) | H | H | H | H | |
| 198 | B16 | 1 | 2 | N(CH$_2$-phenyl) | H | H | H | H | HCl (1:3); H$_2$O (1:1) |
| 199 | B27a | 0 | 2 | NH | H | H | H | H | HCl (1:4); H$_2$O (1:2) |
| 200 | B1a | 1 | 2 | CH$_2$ | OCH$_3$ | 6-OCH$_3$ | H | H | HCl (1:4); H$_2$O (1:1); 2-propanolate (1:1) |
| 201 | B1a | 1 | 3 | NH | H | H | 6-Br | H | HBr (1:4); H$_2$O (1:4) |
| 202 | B16 | 1 | 4 | NH | H | H | H | H | HCl (1:4); H$_2$O (1:3) |
| 296 | B22b | 1 | 2 | NH | CH$_3$ | H | 6-CH$_3$ | CH(CH$_3$)$_2$ | — |

* = position pyridyl

TABLE 8

R—NH—CH₂—CH₂—[piperidine]—a—[benzimidazole with N-L]

| Co. No. | Ex. No. | L | a | R | Physical data |
|---|---|---|---|---|---|
| 203 | B16 | 4-pyrimidinyl | NH | H | HCl (1:4); H₂O (1:2) |
| 204 | B16 | 2-pyrimidinyl | NH | H | HCl (1:3); H₂O (1:1) |
| 205 | B16 | 2-pyrimidinyl | NH | H | |
| 206 | B16 | 3-pyridazinyl | NH | H | HCl (1:3); H₂O (1:1) |
| 207 | B16 | 4,6-dimethoxy-2-pyrimidinyl | NH | H | HCl (1:4); H₂O (1:3) |
| 208 | B16 | 2-pyrimidinyl | NH | H | HCl (1:4); H₂O (1:1) |
| 209 | B16 | 6-methyl-2-pyridyl | CH[N(CH₃)₂] | H | HCl (1:4); H₂O (1:2); 2-propanolate (1:1) |
| 210 | B7 | 6-methyl-2-pyridyl | CH[N(CH₃)₂] | —COOC(CH₃)₃ | |
| 211 | B25a | 2-pyridiyl | NH | CH₃ | HCl (1:4); H₂O (1:2); mp. 224° C. |
| 212 | B27a | 2-[C(CH₃)₃]-6-OH-4-pyrimidinyl | NH | H | |
| 320 | B30 | 2-pyridinyl | NH | H | |
| 319 | B27a | 2-4-dimethyl-5-oxazolyl | NH | H | |
| 329 | B16 | 2,5-dimethyl-4-oxazolyl | NH | H | HCl (1:3); H₂O (1:1) |
| 333 | B16 | 5-methyl-3-isoxazolyl | NH | H | HCl (1:3); H₂O (1:1) |
| 317 | B27a | 2-methyl-5-oxazolyl | NH | H | mp. 115° C.; H₂O (1:1) |
| 323 | B27a | 4-thiazolyl | NH | H | |
| 326 | B16 | 5-phenyl-1,2,4-oxadiazol-3-yl | NH | H | HCl (1:3) |
| 332 | B16 | 2-(hydroxymethyl)-5-oxazolyl | NH | H | HCl (1:4); H₂O (1:2) |
| 331 | B16 | 3-methyl-5-isoxazolyl | NH | H | HCl (1:3); H₂O (1:1) |
| 324 | B16 | 2-(dimethylamino)-4-thiazolyl | CH₂ | H | HCl (1:4); H₂O (1:1); propanolate (1:1) |
| 325 | B27a | 2-methyl-4-thiazolyl | CH₂ | H | |
| 318 | B27a | 2-methyl-3-furanyl | NH | H | mp. 142° C. |
| 312 | B25b | 2-pyridinyl | NH | CH₂—CH₂OH | mp. 151° C. |
| 316 | B30 | 2-methyl-5-oxazolyl | NH | H | HCl (1:4); H₂O (1:1) |

TABLE 9

H₂N—CH₂—CH₂—[piperidine]—HN—[benzimidazole with N-CH₂-monocyclic heterocycle bearing Rᵃ, Rᵇ, Rᶜ]

| Co. No. | Ex. No. | * | a | Rᵃ | Rᵇ | Rᶜ | Physical data |
|---|---|---|---|---|---|---|---|
| 213 | B16 | 2 | N | CH₂C₆H₅ | H | H | HCl (1:4) |
| 214 | B16 | 5 | N | H | 4-CH₃ | H | HCl (1:4); H₂O (1:3) |
| 215 | B16 | 5 | N | CH₃ | 4-CH₃ | H | HCl (1:4); H₂O (1:2) |
| 216 | B16 | 2 | N | CH₃ | 5-COOC₂H₅ | 4-CH₃ | HCl (1:4) |
| 217 | B16 | 2 | N | CH₃ | 5-Cl | H | HCl (1:4); H₂O (1:2) |
| 218 | B16 | 5 | N | 2-propyl | 2-SCH₃ | H | HCl (1:4); H₂O (1:1) |
| 219 | B16 | 5 | N | C₂H₅ | 2-CH₃ | 4-CH₃ | HCl (1:4); H₂O (1:2); 2-propanolate (1:1) |
| 220 | B16 | 5 | N | CH₃ | 2-CH₃ | 4-CH₃ | HCl (1:4); H₂O (1:2) |
| 21 | B17 | 2 | CH | CH₃ | 5-CH₃ | H | H₂O (1:1) |
| 221 | B27a | 2 | CH | CH₃ | 5-COOC₂H₅ | H | |
| 222 | B27a | 2 | CH | CH₃ | 5-COOC₂H₅ | 4-Br | |

* position monocyclic heterocycle

TABLE 10

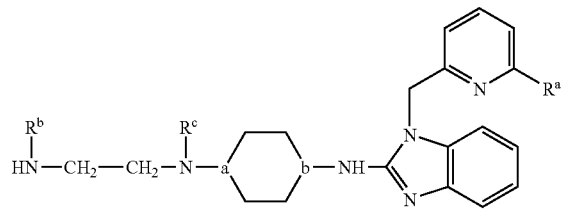

| Co. No. | Ex. No. | a | b | R$^a$ | R$^b$ | R$^c$ | Physical data |
|---|---|---|---|---|---|---|---|
| 14 | B11 | CH | CH | H | COCH$_3$ | H | (cis); mp. 126 |
| 15 | B11 | CH | CH | H | COCH$_3$ | H | (trans); mp. 200 |
| 223 | B16 | CH | CH | H | H | H | (trans); HCl (1:4); H$_2$O (1:1); mp. 210 |

TABLE 10-continued

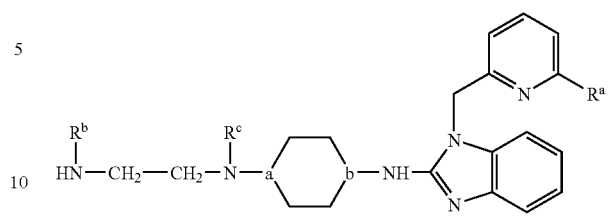

| Co. No. | Ex. No. | a | b | R$^a$ | R$^b$ | R$^c$ | Physical data |
|---|---|---|---|---|---|---|---|
| 29 | B25a | CH | N | CH$_3$ | H | H | |
| 224 | B25a | CH | N | CH$_3$ | H | CH$_3$ | HCl (1:5); H$_2$O (1:3) |

TABLE 11

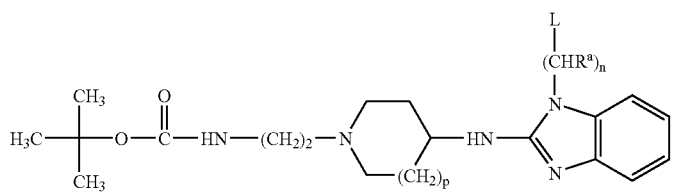

| Co. No. | Ex. No. | n | p | R$^a$ | L | Physical data |
|---|---|---|---|---|---|---|
| 225 | B7 | 1 | 1 | H | 6-chloro-2-pyridyl | |
| 8 | B7 | 1 | 1 | H | 6-methyl-2-pyrazinyl | |
| 226 | B7 | 1 | 2 | H | 2-pyridyl | |
| 227 | B7 | 1 | 1 | H | 5-methyl-2-pyrazinyl | |
| 228 | B7 | 1 | 1 | CH$_3$ | 2-pyridyl | |
| 229 | B7 | 1 | 2 | H | 2-pyridyl | |
| 230 | B7 | 1 | 1 | H | 4-methyl-1H-imidazol-5-yl | |
| 231 | B7 | 1 | 1 | H | 3-methyl-2-pyrazinyl | |
| 232 | B7 | 2 | 1 | H | 2-pyridyl | |
| 233 | B7 | 1 | 1 | H | 1,4-dimethyl-1H-imidazol-5-yl | |
| 234 | B7 | 1 | 1 | H | 4-pyrimidinyl | |
| 235 | B7 | 0 | 1 | — | 2-pyrimidinyl | |
| 236 | B7 | 1 | 1 | H | 6-(hydroxymethyl)-2-pyridyl | |
| 237 | B7 | 1 | 1 | H | 1,4-dimethyl-5-(—COOC$_2$H$_5$)-1H-imidazol-2-yl | |
| 238 | B7 | 1 | 1 | CH$_3$ | 2-pyrazinyl | |
| 239 | B7 | 1 | 1 | H | 3,5,6-trimethyl-2-pyrazinyl | |
| 240 | B7 | 1 | 1 | Ethyl | 2-pyrazinyl | |
| 241 | B7 | 1 | 1 | CH$_3$ | 6-methyl-2-pyrazinyl | |
| 242 | B7 | 1 | 1 | H | 5-chloro-1-methyl-1H-imidazol-2-yl | |
| 243 | B7 | 1 | 1 | H | 4,6-dimethyl-2-pyridyl | |
| 244 | B7 | 1 | 1 | H | 6-bromo-2-pyridyl | |
| 245 | B7 | 1 | 1 | H | 6-(—COOC$_2$H$_5$)-2-pyridyl | |
| 246 | B7 | 1 | 1 | H | 1,5-dimethyl-2-pyrrolyl | |
| 247 | B7 | 1 | 1 | H | 6-methoxy-2-pyridyl | |
| 248 | B7 | 1 | 1 | H | 4-chloro-2-pyridyl | |
| 249 | B7 | 1 | 1 | H | 4-methoxy-2-pyridyl | |
| 250 | B7 | 1 | 1 | H | 2-pyrimidinyl | |
| 251 | B7 | 1 | 1 | H | 3-methoxy-6-methyl-2-pyridyl | |
| 252 | B7 | 1 | 1 | H | 6-methyl-3-(—O—C$_2$H$_4$—O—C$_2$H$_5$)-2-pyridyl | |
| 253 | B7 | 1 | 1 | CH$_3$ | 6-hydroxymethyl-2-pyridyl | |
| 254 | B7 | 1 | 1 | H | 6-bromo-3-pyridyl | |
| 9 | B8 | 1 | 1 | H | 2-(1,1-dimethylethyl)-6-hydroxy-4-pyrimidinyl | |
| 255 | B8 | 1 | 1 | H | 1-(phenylmethyl)-1H-imidazol-2-yl | |
| 256 | B8 | 1 | 1 | H | 1-(2-propyl)-2-(—S—CH$_3$)-1H-imidazol-5-yl | |
| 257 | B8 | 1 | 1 | CH$_3$ | 6-chloro-2-pyridyl | |

TABLE 11-continued

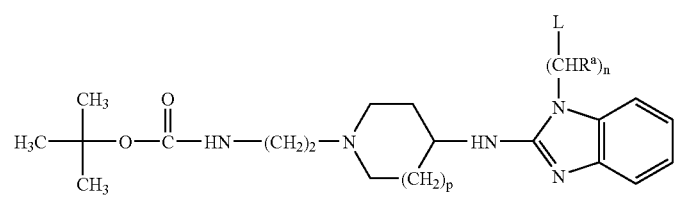

| Co. No. | Ex. No. | n | p | $R^a$ | L | Physical data |
|---|---|---|---|---|---|---|
| 258 | B8 | 1 | 1 | H | 1-ethyl-2,4-dimethyl-1H-imidazol-5-yl | $H_2O$ (1:1) |
| 259 | B8 | 1 | 1 | H | 3-hydroxy-6-methyl-2-pyridyl | |
| 260 | B8 | 1 | 1 | H | 4,6-dimethoxy-2-pyrimidinyl | |
| 261 | B8 | 1 | 1 | H | 5-(—$COOC_2H_5$)-2-pyrazinyl | |
| 262 | B8 | 1 | 1 | H | 1,2,4-trimethyl-1H-imidazol-5-yl | |
| 10 | B9a | 1 | 1 | H | 3-(—O—$C_2H_4Cl$)-6-methyl-2-pyridyl | |
| 263 | B9a | 1 | 1 | H | 6-(—$CH_2$—O—$CH_3$)-2-pyridyl | |
| 11 | B9b | 1 | 1 | H | 3-[—O—$C_2H_4$—$N(CH_3)_2$]-6-methyl-2-pyridyl | |
| 12 | B10a | 1 | 1 | H | 6-chloro-3-pyridazinyl | |
| 13 | B10b | 1 | 1 | H | 3-pyridazinyl | |
| 330 | B7 | 1 | 1 | H | 2-methyl-4-methoxycarbonyl-5-oxazolyl | |

TABLE 12

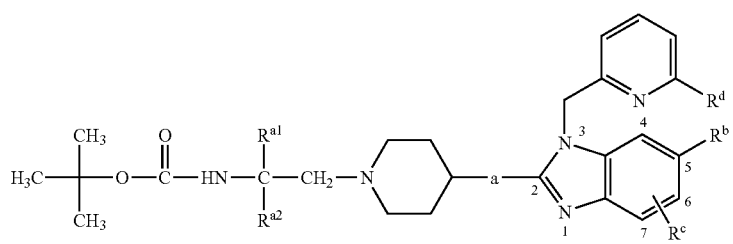

| Co. No. | Ex. No. | $R^{a1}, R^{a2}$ | $R^b$ | $R^c$ | a | $R^d$ | Physical data |
|---|---|---|---|---|---|---|---|
| 264 | B7 | H, H | $OCH_3$ | 6-$OCH_3$ | $CH_2$ | H | |
| 265 | B7 | H, H | H | H | $N(CH_3)$ | H | |
| 266 | B7 | H, H | H | H | $N(CH_2$—$C_6H_5)$ | H | |
| 267 | B7 | H, H | Cl | 6-Cl | NH | $CH_3$ | |
| 268 | B7 | H, H | $CH_3$ | 6-$CH_3$ | NH | $CH_3$ | |
| 269 | B7 | H, H | H | 4-Cl | NH | $CH_3$ | |
| 270 | B7 | H, H | H | 7-Cl | NH | $CH_3$ | |
| 271 | B7 | H, H | H | 6-$NO_2$ | NH | $CH_3$ | |
| 272 | B7 | H, H | $NO_2$ | H | NH | $CH_3$ | |
| 273 | B7 | H, H | H | 7-$CH_3$ | NH | $CH_3$ | |
| 274 | B7 | H, H | H | 4-$CH_3$ | NH | $CH_3$ | $H_2O$ (1:1) |
| 275 | B7 | H, H | H | 6-ethoxy-carbonyl | NH | $CH_3$ | |
| 276 | B7 | H, H | H | 6-hydroxy-methyl | NH | $CH_3$ | |
| 277 | B7 | H, H | $CF_3$ | H | NH | $CH_3$ | |
| 278 | B7 | H, H | H | 6-$CF_3$ | NH | $CH_3$ | |
| 279 | B7 | H, H | H | H | NH | —CO—$N(CH_3)_2$ | |
| 280 | B7 | H, H | Cl | H | NH | $CH_3$ | |
| 16 | B12 | $CH_3, CH_3$ | H | H | NH | H | |
| 17 | B13 | H, H | —$NH_2$ | H | NH | $CH_3$ | |
| 281 | B13 | H, H | H | 6-$NH_2$ | NH | $CH_3$ | |
| 19 | B15 | —$CH_2OH$, H | H | H | NH | H | |

TABLE 13

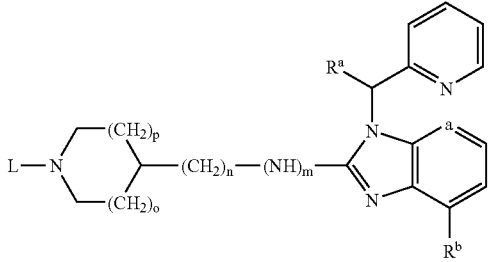

| Co. No. | Ex. No. | n | m | o | p | a | $R^a$ | $R^b$ | L | Physical data |
|---|---|---|---|---|---|---|---|---|---|---|
| 6 | B5 | 1 | 0 | 2 | 1 | CH | H | H | H | |
| 283 | B27a | 1 | 0 | 1 | 1 | N | H | H | —(CH$_2$)$_2$—NH$_2$ | HCl (1:4), H$_2$O (1:1); 2-propanolate (1:1) |
| 284 | B27a | 1 | 1 | 1 | 1 | N | H | H | —(CH$_2$)$_2$—NH$_2$ | HCl (1:1) |
| 285 | B27a | 1 | 1 | 0 | 2 | CH | H | H | —(CH$_2$)$_2$—NH$_2$ | HCl (1:4), H$_2$O (1:1); mp. 205° C. |
| 286 | B4 | 1 | 1 | 0 | 2 | CH | H | H | H | |
| 30 | B26 | 0 | 1 | 1 | 1 | CH | CH$_3$ | H | —CH(CH$_3$)—CH$_2$—NH$_2$ | mp. 85° C. |

TABLE 14

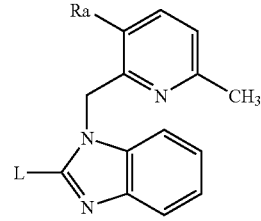

| Co. No. | Ex. No. | $R_a$ | L | Physical data |
|---|---|---|---|---|
| 288 | B25a | H | 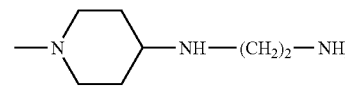 —N⟨piperidine⟩—NH—(CH$_2$)$_2$—NH$_2$ | |
| 289 | B4 | H | 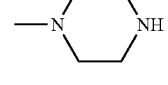 —N⟨piperazine⟩NH | |
| 309 | B19 | H | —NH—(CH$_2$)$_3$—NH$_2$ | HCl (1:3); H$_2$O (1:2) |
| 347 | B16 | H | —NH—CH(CH$_3$)—(CH$_2$)$_2$—NH—(CH$_2$)$_2$—NH$_2$ | HCl (1:4); 2-propanolate (1:1) |
| 345 | B19 | H | —N(CH$_3$)—(CH$_2$)$_3$—NH—(CH$_2$)$_2$—NH$_2$ | HCl (1:4); H$_2$O (1:1) |
| 346 | B19 | H | 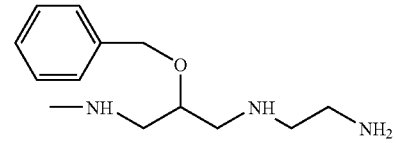 —NH—CH$_2$—CH(OCH$_2$Ph)—CH$_2$—NH—(CH$_2$)$_2$—NH$_2$ | HCl (1:4); H$_2$O (1:1) |
| 341 | B25a | H | 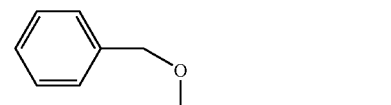 —NH—CH$_2$—CH(OCH$_2$Ph)—CH$_2$—NH$_2$ | HCl (1:3); H$_2$O (1:1) |
| 313 | B25c | OH | —NHCH$_2$CH(OH)CH$_2$NH$_2$ | |

TABLE 15

| Co. No. | Ex. No. | a | n | R$^a$ | R$^b$ | R$^c$ | R$^d$ | R$_f$ | Physical data |
|---|---|---|---|---|---|---|---|---|---|
| 290 | B16 | CH | 0 | 3-OH | 6-CH$_3$ | 7-CH$_3$ | H | H | HCl (1:4); H$_2$O (1:4) |
| 291 | B22b | N | 0 | 3-OH | 6-CH$_3$ | 7-CH$_3$ | H | CH—(CH$_3$)$_2$ | — |
| 292 | B22b | CH | 0 | 3-OH | 6-CH$_3$ | 7-CH$_3$ | H | CH$_3$ | HCl (1:4); H$_2$O (1:3) |
| 293 | B22b | CH | 0 | 3-OH | 6-CH$_3$ | 7-CH$_3$ | H | CH—(CH$_3$)$_2$ | — |
| 195 | B22b | CH | 0 | 6-CH$_3$ | H | 7-CH$_3$ | H | CH—(CH$_3$)$_2$ | — |
| 303 | B28 | CH | 1 | 6-CH$_3$ | H | 7-CH$_3$ | H | OH | H$_2$O (1:1) |
| 304 | B22b | CH | 0 | 6-CH$_3$ | H | 6-CH$_3$ | H | CH—(CH$_3$)$_2$ | — |
| 342 | B16 | CH | 0 | 3-OH | 6-CH$_3$ | 5-Cl | 7-CH$_3$ | H | HCl (1:4), 2-propanolate (1:1) |
| 348 | B16 | CH | 0 | 3-OH | 6-CH$_3$ | 5-Br | 7-CH$_3$ | H | HCl (1:4) |
| 351 | B22b | CH | 0 | 3-OH | 6-CH$_3$ | 4-CH$_3$ | H | CH—(CH$_3$)$_2$ | HCl (1:4); H$_2$O (1:1) |
| 340 | B16 | CH | 0 | 3-OH | 6-CH$_3$ | 4-CH$_3$ | H | H | HCl (1:4); H$_2$O (1:2) |
| 344 | B16 | CH | 0 | 3-OH | 6-CH$_3$ | 4-CH$_3$ | 6-Cl | H | HCl (1:4); H$_2$O (1:4) |
| 349 | B16 | CH | 0 | 3-OH | 6-CH$_3$ | 5-(4-fluoro-benzoyl) | H | H | HCl (1:4); H$_2$O (1:2) |
| 350 | B16 | CH | 0 | 3-OH | 6-CH$_3$ | 6-(4-fluoro-benzoyl) | H | H | HCl (1:4); H$_2$O (1:2) |
| 355 | B16 | CH | 0 | 3-OH | 6-CH$_3$ | 7-CH$_3$ | H | H | |
| 356 | B16 | CH | 0 | 3-OH | 6-CH$_3$ | 7-CH$_3$ | H | H | C$_4$H$_6$O$_4$ (1:1); H$_2$O (1:1) |
| 357 | B16 | CH | 0 | 3-OH | 6-CH$_3$ | 7-CH$_3$ | H | H | C$_4$H$_6$O$_5$ (1:1); H$_2$O (1:2) |
| 353 | B16 | CH | 0 | 3-OH | 6-CH$_3$ | 7-CH$_3$ | H | H | HCl (1:4); H$_2$O(1:5) |

TABLE 16

| Co. No. | Ex. No. | a | b | R$^a$ | L | P | Physical data |
|---|---|---|---|---|---|---|---|
| 295 | B22b | CH | CH | 5-Cl | —CH$_2$—CH(NH$_2$)—CH(CH$_3$)$_2$ | 2-chloro-1,5-dimethyl-4-(imidazolyl) with CH$_3$ at 4-position | |
| 297 | B22b | CH | CH | 5-Cl | —CH$_2$—CH(NH$_2$)—CH(CH$_3$)$_2$ | 1,4,5-trimethyl-imidazolyl | H$_2$O (1:1) |

TABLE 16-continued

[Structure: L—N(piperidine)—HN—C(=N)—imidazole fused ring with CH2—P on N3, positions a4 and b, with Ra substituent]

| Co. No. | Ex. No. | a | b | Rª | L | P | Physical data |
|---|---|---|---|---|---|---|---|
| 298 | B22b | CH | CH | H | —CH₂—CH(NH₂)—CH(CH₃)₂ | 1,5-dimethyl-2-chloro-1H-imidazol-4-yl (H₃C on 4, CH₃ on N1, Cl on 2) | |
| 310 | B1b | CH | N | H | H | 2,6-dimethyl-3-hydroxypyridinyl | HBr (1:3). H₂O |
| 302 | B1a | CH | CH | 5-Cl | H | 1,4,5-trimethyl-1H-imidazolyl | (1:1). C₂H₆O (1:1) |
| 321 | B27a | N | CH | H | —CH₂—CH₂—NH₂ | 2,4-dimethyl-5-oxazolyl | |
| 339 | B8 | N | CH | 7-CH₃ | —C(=O)—O—CH₂—CH₃ | 2,6-dimethyl-3-hydroxypyridinyl | |
| 336 | B9b | CH | CH | H | —C(=O)—O—C(CH₃)₃ | 3-[2-(dimethylamino)ethoxy]-2,6-dimethylpyridin... (N,N-dimethyl-aminoethoxy on 2,6-dimethylpyridine) | |
| 337 | B25a | CH | CH | H | —C(=O)—O—CH₂—CH₃ | 3-amino-2-methylpyridinyl | mp. 171° C. |
| 352 | B7 | CH | CH | 7-CH₃ | —(CH₂)₃—NH—C(=O)OC(CH₃)₃ | 2,6-dimethyl-3-hydroxypyridinyl | |
| 354 | B16 | CH | CH | 7-CH₃ | —(CH₂)₃—NH—CH=O | 2,6-dimethyl-3-hydroxypyridinyl | .HCl (1:4) |

TABLE 17

![structure]

| Co. No. | Ex. No. | a | b | c | $R^a$ | $R^b$ | $R^c$ | L | Physical data |
|---|---|---|---|---|---|---|---|---|---|
| 343 | B1b | CH | NH | CH | H | 5-Br | 7-$CH_3$ | 3-hydroxy-6-methyl-2-pyridinyl | HBr (1:3) |
| 338 | B1b | CH | NH | CH | H | H | 7-$CH_3$ | 3-hydroxy-6-methyl-2-pyridinyl | |
| 335 | B20 | N | NH | CH | —$CH_2$—$CH(CH(CH_3)_2)$—$NH_2$ | H | H | 2-pyridinyl | mp. 198° C. |
| 334 | B27a | N | NH | CH | —$(CH_2)_2$—$NH_2$ | H | H | 2-pyridinyl | mp. 186 |
| 322 | B27a | N | $CH_2$ | N | —$(CH_2)_2$—$NH_2$ | H | H | 2-methyl-5-oxazolyl | |
| 314 | B27b | CH | $CH_2$ | N | —$(CH_2)_2$—$NH_2$ | H | H | 5-methoxymethyl-2-furanyl | |

C. Pharmacological Example

EXAMPLE C1

In Vitro Screening for Activity Against Respiratory Syncytial Virus

The percent protection against cytopathology caused by viruses (antiviral activity or $IC_{50}$) achieved by tested compounds and their cytotoxicity ($CC_{50}$) were both calculated from dose-response curves. The selectivity of the antiviral effect is represented by the selectivity index (SI), calculated by dividing the $CC_{50}$ (cytotoxic dose for 50% of the cells) by the $IC_{50}$ (antiviral activity for 50% of the cells).

Automated tetrazolium-based colorimetric assays were used for determination of $IC_{50}$ and $CC_{50}$ of test compounds. Flat-bottom, 96-well plastic microtiter trays were filled with 180 μl of Eagle's Basal Medium, supplemented with 5% FCS (0% for FLU) and 20 mM Hepes buffer. Subsequently, stock solutions (7.8× final test concentration) of compounds were added in 45 μl volumes to a series of triplicate wells so as to allow simultaneous evaluation of their effects on virus- and mock-infected cells. Five five-fold dilutions were made directly in the microtiter trays using a robot system. Untreated virus controls, and HeLa cell controls were included in each test. Approximately 100 TCID50 of Respiratory Syncytial Virus was added to two of the three rows in a volume of 50 μl. The same volume of medium was added to the third row to measure the cytotoxicity of the compounds at the same concentrations as those used to measure the antiviral activity. After two hours of incubation, a suspension ($4\times10^5$ cells/ml) of HeLa cells was added to all wells in a volume of 50 μl. The cultures were incubated at 37° C. in a 5% $CO_2$ atmosphere. Seven days after infection the cytotoxicity and the antiviral activity was examined spectrophotometrically. To each well of the microtiter tray, 25 μl of a solution of MAT (3-(4,5-dimethylthiazol-2-yl)-2,5-diphenyltetrazolium bromide) was added. The trays were further incubated at 37° C. for 2 hours, after which the medium was removed from each cup. Solubilization of the formazan crystals was achieved by adding 100 μl 2-propanol. Complete dissolution of the formazan crystals were obtained after the trays have been placed on a plate shaker for 10 min. Finally, the absorbances were read in an eight-channel computer-controlled photometer (Multiskan MCC, Flow Laboratories) at two wavelengths (540 and 690 nm). The absorbance measured at 690 nm was automatically subtracted from the absorbance at 540 nm, so as to eliminate the effects of non-specific absorption.

Particular $IC_{50}$, $CC_{50}$ and SI values are listed in Table 18 hereinbelow.

TABLE 18

| Co. No. | $IC_{50}$ (μM) | $CC_{50}$ (μM) | SI |
|---|---|---|---|
| 290 | 0.00013 | >0.010 | >79 |
| 292 | 0.00032 | 63.85 | 199526 |
| 351 | 0.00063 | 50.04 | 79433 |
| 297 | 0.00251 | >99.93 | >39811 |
| 296 | 0.00631 | 19.95 | 3162 |
| 27 | 0.0126 | >100.08 | >7943 |
| 192 | 0.0631 | 63.1 | 1000 |
| 144 | 0.1259 | 50.11 | 398 |
| 222 | 0.5012 | 39.59 | 79 |
| 142 | 1.2589 | 40.28 | 32 |
| 145 | 2.5119 | >50.24 | >20 |

The invention claimed is:
1. A compound of formula (I')

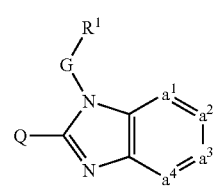

or an addition salt or stereochemically isomeric form thereof,
wherein -$a^1$=$a^2$-$a^3$=$a^4$- represents a bivalent radical of formula —CH=CH—CH=CH—  (a-1);

wherein each hydrogen atom in the radical (a-1) may optionally be replaced by halo, $C_{1-6}$alkyl, nitro, amino, hydroxy, $C_{1-6}$alkyloxy, polyhalo$C_{1-6}$alkyl, carboxyl, amino$C_{1-6}$alkyl, mono- or di($C_{1-4}$alkyl)amino$C_{1-6}$alkyl, $C_{1-6}$alkyloxycarbonyl, hydroxy$C_{1-6}$alkyl, or a radical of formula

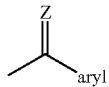

wherein Z is O, CH—C(=O)—NR$^{5a}$R$^{5b}$, CH$_2$, CH—C$_{1-6}$alkyl, N—OH or N—O—C$_{1-6}$alkyl;

Q is a radical of formula

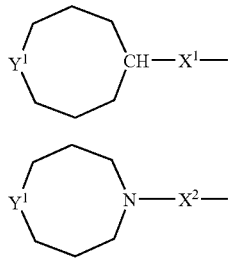

wherein;

$Y^1$ is a bivalent radical of formula —NR$^2$— or —CH(NR$^2$R$^4$)—;

$X^1$ is NR$^4$, S, S(=O), S(=O)$_2$, O, CH$_2$, C(=O), C(=CH$_2$), CH(OH), CH(CH$_3$), CH(OCH$_3$), CH(SCH$_3$), CH(NR$^{5a}$R$^{5b}$), CH$_2$—NR$^4$ or NR$^4$—CH$_2$;

$X^2$ is a direct bond, CH$_2$, C(=O), NR$^4$, $C_{1-4}$alkyl-NR$^4$, NR$^4$—C$_{1-4}$alkyl; and whereby each hydrogen atom in the carbocycles and the heterocycles defined in radicals (b-7) and (b-8) may optionally be replaced by R$^3$; with the proviso that when R$^3$ is hydroxy or $C_{1-6}$alkyloxy, then R$^3$ can not replace a hydrogen atom in the α position relative to a nitrogen atom;

G is a direct bond or $C_{1-10}$alkanediyl;

R$^1$ is a monocyclic heterocycle selected from piperidinyl, piperazinyl, pyridyl, pyrazinyl, pyridazinyl, pyrimidinyl, pyrrolyl, furanyl, tetrahydrofuranyl, thienyl, oxazolyl, thiazolyl, imidazolyl, pyrazolyl, isoxazolyl, oxadiazolyl, and isothiazolyl; and each heterocycle may optionally be substituted with 1 or where possible more substituents selected from halo, hydroxy, amino, cyano, carboxy, $C_{1-6}$alkyl, $C_{1-6}$alkyloxy, $C_{1-6}$alkylthio, $C_{1-6}$alkyloxy$C_{1-6}$alkyl, aryl, aryl$C_{1-6}$alkyl, aryl$C_{1-6}$alkyloxy, hydroxy$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkylcarbonylamino, $C_{1-6}$alkyl-SO$_2$—NR$^{5c}$—, aryl-SO$_2$—NR$^{5c}$—, $C_{1-6}$alkyloxycarbonyl, —C(=O)—NR$^{5c}$R$^{5d}$, HO(—CH$_2$—CH$_2$—O)$_n$—, halo(—CH$_2$—CH$_2$—O)$_n$—, $C_{1-6}$alkyloxy(—CH$_2$—CH$_2$—O)$_n$—, aryl$C_{1-6}$alkyloxy(—CH$_2$—CH$_2$—O)$_n$— and mono- or di($C_{1-6}$alkyl)amino(—CH$_2$—CH$_2$—O)$_n$—;

each n independently is 1, 2, 3 or 4;

R$^2$ is hydrogen, formyl, $C_{1-6}$alkylcarbonyl, Hetcarbonyl, pyrrolidinyl, piperidinyl, homopiperidinyl, $C_{3-7}$cycloalkyl substituted with N(R$^6$)$_2$, or $C_{1-10}$alkyl substituted with N(R$^6$)$_2$ and optionally with a second, third or fourth substituent selected from amino, hydroxy, $C_{3-7}$cycloalkyl, $C_{2-5}$alkanediyl, piperidinyl, mono- or di($C_{1-6}$alkyl)amino, $C_{1-6}$alkyloxycarbonylamino, aryl and aryloxy;

R$^3$ is hydrogen, hydroxy, $C_{1-6}$alkyl, $C_{1-6}$alkyloxy, aryl $C_{1-6}$alkyl or aryl$C_{1-6}$alkyloxy;

R$^4$ is hydrogen, $C_{1-6}$alkyl or aryl$C_{1-6}$alkyl;

R$^{5a}$, R$^{5b}$, R$^{5c}$ and R$^{5d}$ each independently are hydrogen or $C_{1-6}$alkyl; or R$^{5a}$ and R$^{5b}$, or R$^{5c}$ and R$^{5d}$ taken together form a bivalent radical of formula —(CH$_2$)$_s$— wherein s is 4 or 5;

R$^6$ is hydrogen, $C_{1-4}$alkyl, formyl, hydroxy$C_{1-6}$alkyl, $C_{1-6}$alkylcarbonyl or $C_{1-6}$alkyloxycarbonyl;

aryl is phenyl or phenyl substituted with 1 or more substituents selected from halo, hydroxy, $C_{1-6}$alkyl, hydroxy$C_{1-6}$alkyl, polyhalo$C_{1-6}$alkyl, and $C_{1-6}$alkyloxy; and Het is pyridyl, pyrimidinyl, pyrazinyl, or pyridazinyl.

2. A pharmaceutical composition comprising a pharmaceutically acceptable carrier and as active ingredient a therapeutically effective amount of a compound of claim 1.

3. A process of preparing a composition as claimed in claim 2, comprising the step of intimately mixing said carrier with said compound.

4. A process of preparing a compound as claimed in claim 1, comprising at least one step selected from the group consisting of:

a) reacting an intermediate of formula (II-a) or (II-b) with an intermediate of formula (III)

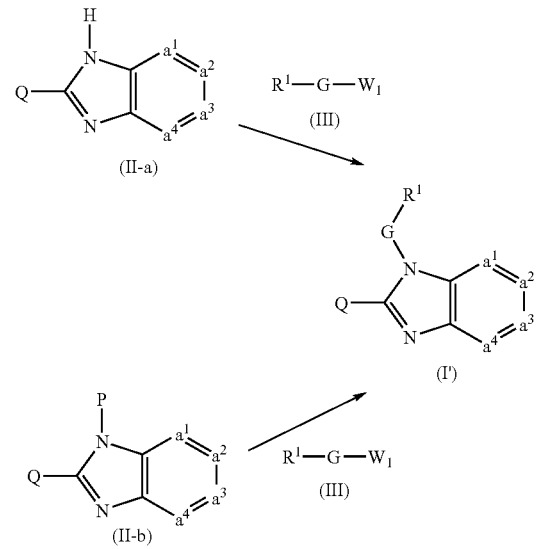

with R$^1$, G, Q and -a$^1$=a$^2$-a$^3$=a$^4$- defined as in claim 2, and W$_1$ being a leaving group, in the presence of a base and in a reaction-inert solvent;

b) deprotecting an intermediate of formula (IV)

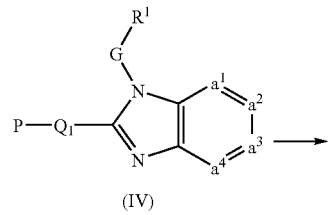

-continued

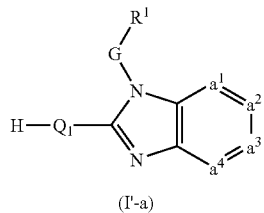
(I'-a)

with $R^1$, G, and $-a^1=a^2-a^3=a^4-$ defined as in claim 2, H-$Q_1$ being defined as Q according to claim 2 provided that $R^2$ or at least one $R^6$ substituent is hydrogen, and P being a protective group;

c) deprotecting and reducing an intermediate of formula (IV-a)

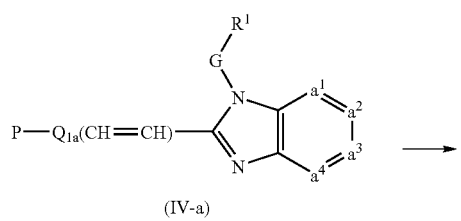
(IV-a)

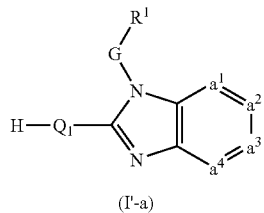
(I'-a)

with $R^1$, G, and $-a^1=a^2-a^3=a^4-$ defined as in claim 2, H-$Q_1$ being defined as Q according to claim 2 provided that $R^2$ or at least one $R^6$ substituent is hydrogen, $Q_{1a}(CH=CH)$ being defined as $Q_1$ provided that $Q_1$ comprises an unsaturated bond, and P being a protective group;

d) deprotecting an intermediate of formula (V)

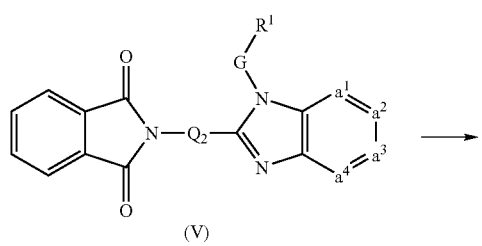
(V)

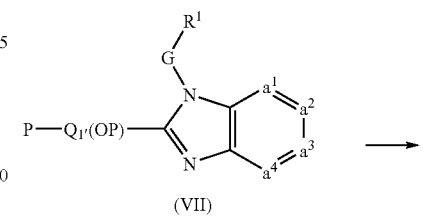
(I'-a-1)

with $R^1$, G, and $-a^1=a^2-a^3=a^4-$ defined as in claim 2, and $H_2N$-$Q_2$ being defined as Q according to claim 2 provided that both $R^6$ substituents are hydrogen or R and $R^4$ are both hydrogen;

e) deprotecting an intermediate of formula (VI)

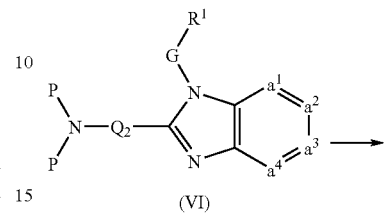
(VI)

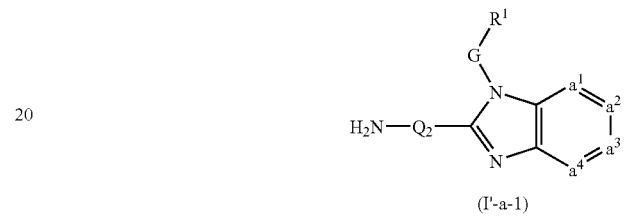
(I'-a-1)

with $R^1$, G, and $-a^1=a^2-a^3=a^4-$ defined as in claim 2, and $H_2N$-$Q_2$ being defined as Q according to claim 2 provided that both $R^6$ substituents are hydrogen or $R^2$ and $R^4$ are both hydrogen, and P being a protective group;

f) deprotecting an intermediate of formula (VII) or (VIII)

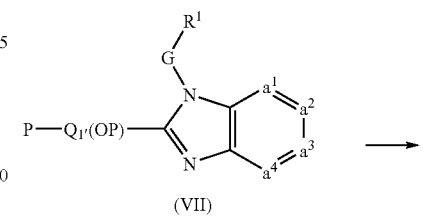
(VII)

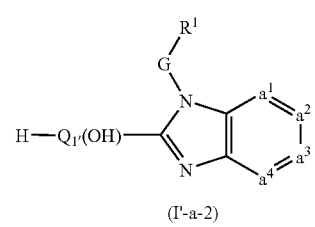
(I'-a-2)

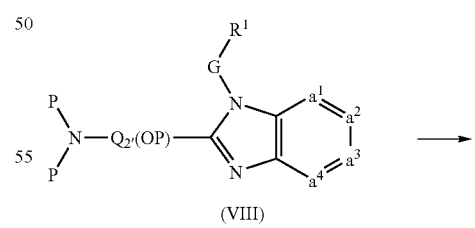
(VIII)

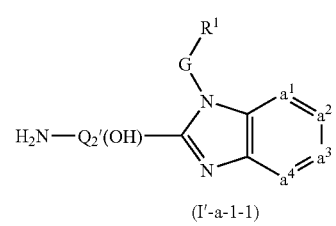
(I'-a-1-1)

with R¹, G, and -a¹=a²-a³=a⁴- defined as in claim 2, H-Q₁ʹ(OH) being defined as Q according to claim 2 provided that R² or at least one R⁶ substituent is hydrogen and provided that Q comprises a hydroxy moiety, H₂N-Q₂ʹ(OH) being defined as Q according to claim 2 provided that both R⁶ substituents are hydrogen or R² and R⁴ are both hydrogen and provided that Q comprises a hydroxy moiety, and P being a protective group;

g) amination of an intermediate of formula (IX)

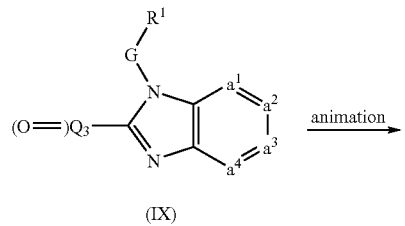

(IX)

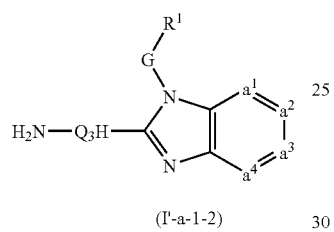

(I'-a-1-2)

with R¹, G, and -a¹=a²-a³=a⁴- defined as in claim 2, and H₂N-Q₃H being defined as Q according to claim 2 provided that both R⁶ substituents are hydrogen or R² and R⁴ are both hydrogen, and the carbon adjacent to the nitrogen carrying the R⁶, or R² and R⁴ substituents contains at least one hydrogen, in the presence of an amination reagent;

h) reducing an intermediate of formula (X)

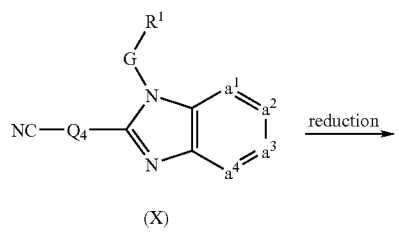

(X)

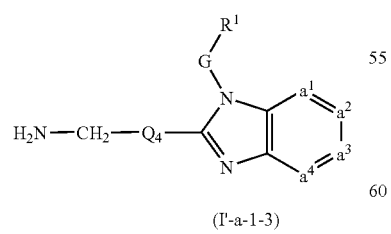

(I'-a-1-3)

with R¹, G, and -a¹=a²-a³=a⁴- defined as in claim 2, and H₂N—CH₂-Q₄ being defined as Q according to claim 2 provided that Q comprises a —CH₂—NH₂ moiety, in the presence of a suitable reducing agent;

i) reducing an intermediate of formula (X-a)

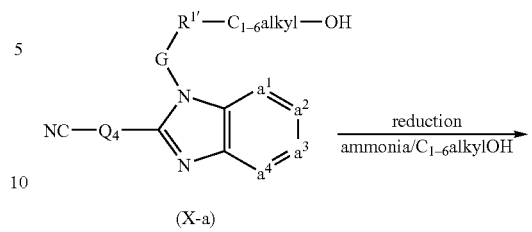

(X-a)

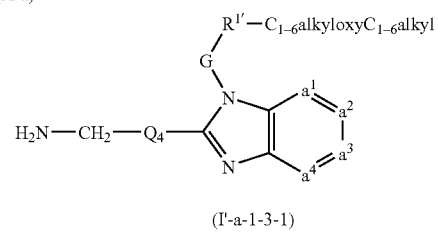

(I'-a-1-3-1)

with G, and -a¹=a²-a³=a⁴- defined as in claim 2, H₂N—CH₂-Q₄ being defined as Q according to claim 2 provided that Q comprises a —CH₂—NH₂ moiety, and R¹ʹ being defined as R¹ according to claim 2 provided that it comprises at least one substituent, in the presence of a reducing agent and solvent;

j) amination of an intermediate of formula (XI)

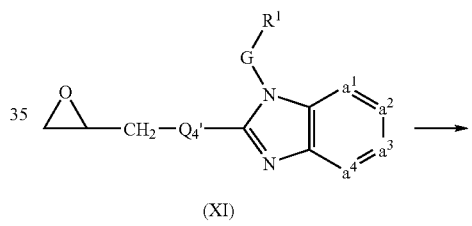

(XI)

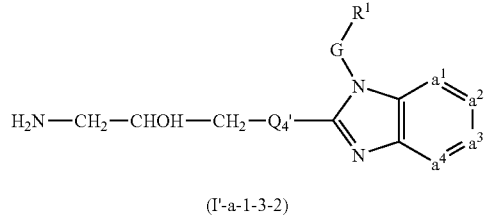

(I'-a-1-3-2)

with R¹, G, and -a¹=a²-a³=a⁴- defined as in claim 2, and H₂N—CH₂—CHOH—CH₂-Q₄ʹ being defined as Q according to claim 2 provided that Q comprises a CH₂—CHOH—CH₂—NH₂ moiety, in the presence of an amination reagent;

k) reacting an intermediate of formula (XII) with formic acid, formamide and ammonia

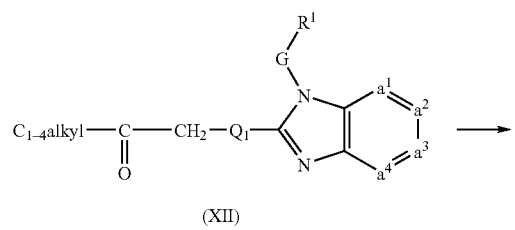

(XII)

-continued

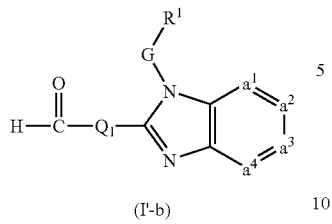

(I'-b)

with $R^1$, G, and $-a^1=a^2-a^3=a^4-$ defined as in claim 2, and H—C(=O)-$Q_1$ being defined as Q according to claim 2 provided that $R^2$ or at least one $R^6$ substituent is formyl;

l) amination of an intermediate of formula (XIII) by reaction with an intermediate of formula (XIV)

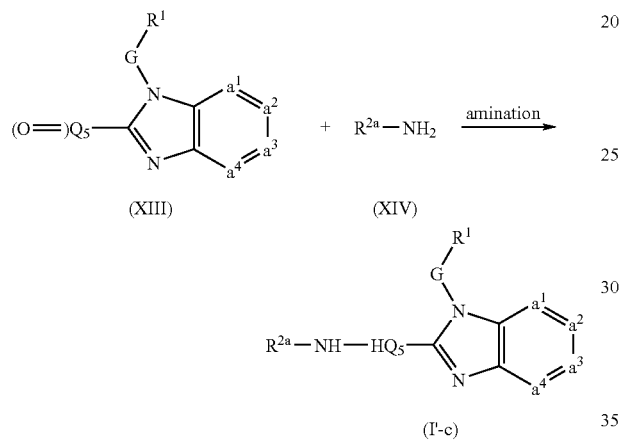

with $R^1$, G, and $-a^1=a^2-a^3=a^4-$ defined as in claim 2, and $R^{2a}$—NH—$HQ_5$ being defined as Q according to claim 2 provided that $R^2$ is other than hydrogen and is represented by $R^{2a}$, $R^4$ is hydrogen, and the carbon atom adjacent to the nitrogen atom carrying the $R^2$ and $R^4$ substituents, carries also at least one hydrogen atom, in the presence of a reducing agent;

m) reducing an intermediate of formula (XV)

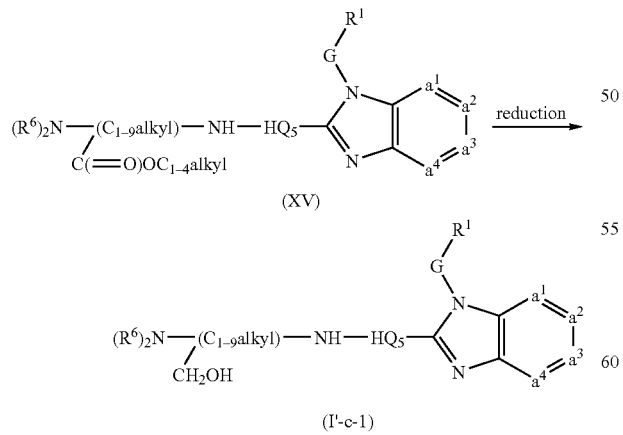

with $R^1$, G, and $-a^1=a^2-a^3=a^4-$ defined as in claim 2, and $(R^6)_2N$—[$(C_{1-9}$alkyl)$CH_2OH$]—NH—$HQ_5$ being defined as Q according to claim 2 provided that $R^3$ is other than hydrogen and is represented by $C_{1-10}$alkyl substituted with $N(R_6)_2$ and with hydroxy, and the carbon atom carrying the hydroxy, carries also two hydrogen atoms, and provided that $R^4$ is hydrogen, and the carbon atom adjacent to the nitrogen atom carrying the $R^2$ and $R^4$ substituents, carries also at least one hydrogen atom, with a reducing agent;

n) deprotecting an intermediate of formula (XVI), (XVI-a) or (XVI-b)

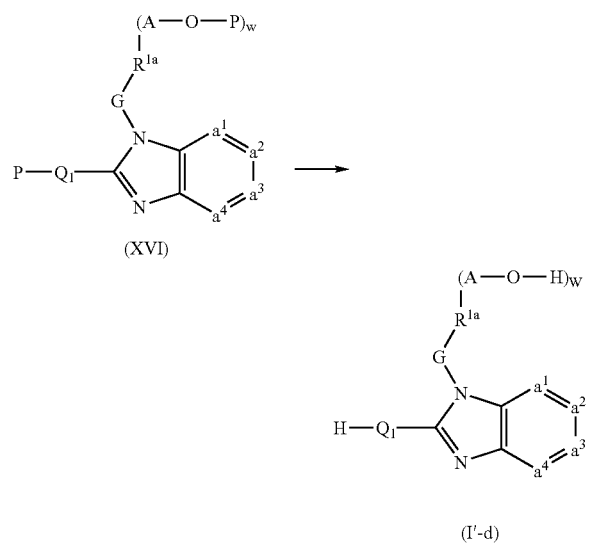

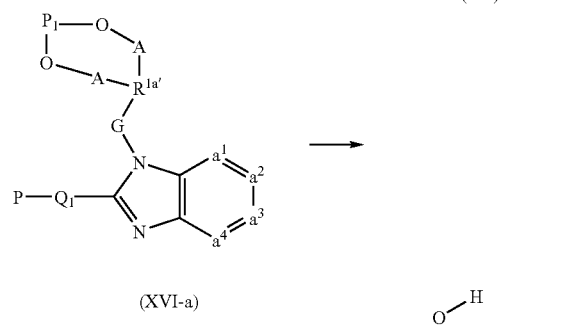

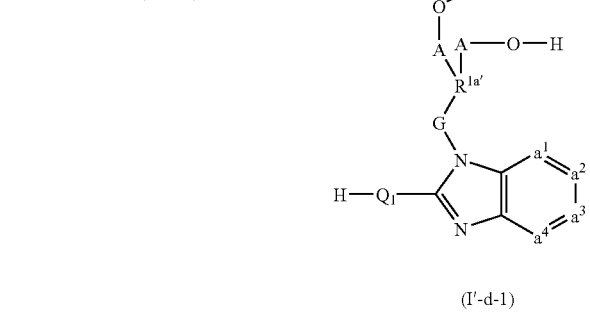

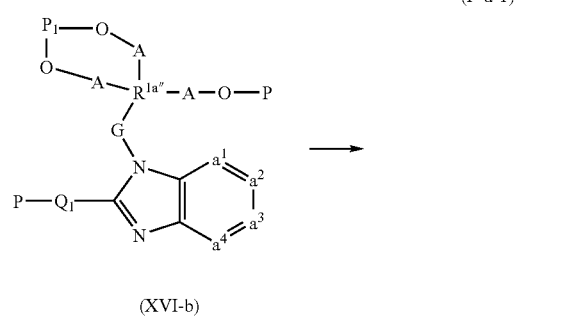

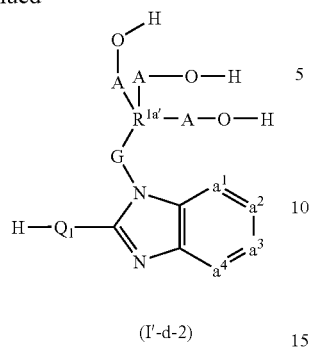

(I'-d-2)

with G, and -a¹=a²-a³=a⁴- defined as in claim 2, and H-Q being defined as Q according to claim 2 provided that R² or at least one R⁶ substituent is hydrogen, and R¹ᵃ-(A-O—H)$_w$, R¹ᵃ'-(A-O—H)$_2$ and R¹ᵃ''-(A-O—H)$_3$ being defined as R¹ according to claim 2 provided that R¹ is substituted with hydroxy, hydroxyC$_{1-6}$alkyl, or HO(—CH$_2$—CH$_2$—O)$_n$—, with w being an integer from 1 to 4 and P or P$_1$ being a protecting group, with an acid; and o) amination of an intermediate of formula (XIX)

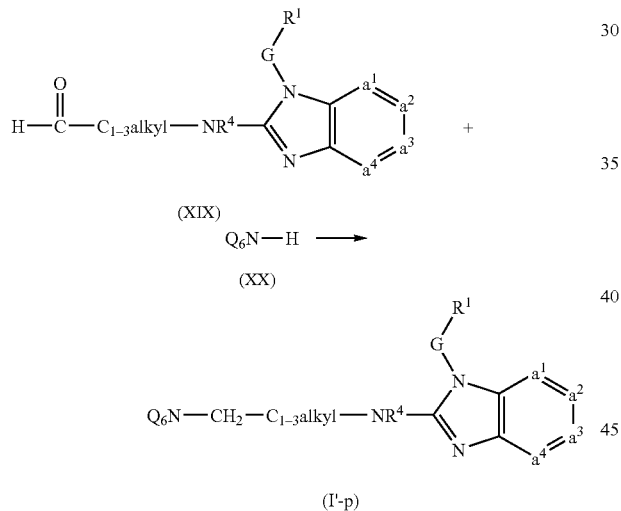

with R¹, G, and -a¹=a²-a³=a⁴- defined as in claim 2, and Q$_6$N—CH$_2$—C$_{1-3}$alkyl-NR⁴ being defined as Q according to claim 2 provided that in the definition of Q, X² is C$_{2-4}$alkyl-NR⁴, in the presence of an amination agent.

5. The process of claim 4, further comprising the step of converting compound of formula (I'), or stereochemically isomeric forms thereof, into a therapeutically active non-toxic acid addition salt by treatment with an acid.

6. The process of claim 4, further comprising the step of converting compound of formula (I'), or stereochemically isomeric forms thereof, into a therapeutically active non-toxic base addition salt by treatment with alkali.

7. The process of claim 4, further comprising the step of converting the acid addition salt form of compound of formula (I'), or stereochemically isomeric forms, thereof, into the free base by treatment with alkali.

8. The process of claim 4, further comprising the step of converting the base addition salt form of compound of formula (I'), or stereochemically isomeric forms, thereof, into the free acid by treatment with acid.

9. A method of treating a respiratory syncytial viral infection, comprising the step of providing a compound of formula

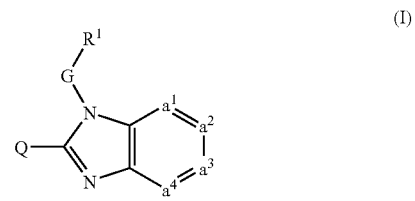

(I)

or an addition salt or stereochemically isomeric form thereof, wherein -a¹=a²-a³=a⁴- represents a bivalent radical of formula —CH=CH—CH=CH— (a-1);

wherein each hydrogen atom in the radical (a-1) may optionally be replaced by halo, C$_{1-6}$alkyl, nitro, amino, hydroxy, C$_{1-6}$alkyloxy, polyhaloC$_{1-6}$alkyl, carboxyl, aminoC$_{1-6}$alkyl, mono- or di(C$_{1-4}$alkyl)aminoC$_{1-6}$alkyl, C$_{1-6}$alkyloxycarbonyl, hydroxyC$_{1-6}$alkyl, or a radical of formula

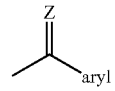

wherein Z is O, CH—C(=O)—NR⁵ᵘR⁵ᵇ, CH$_2$, CH—C$_{1-6}$alkyl, N—OH or N—O—C$_{1-6}$alkyl;

Q is a radical of formula

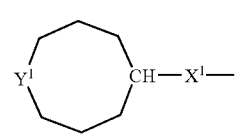

(b-7)

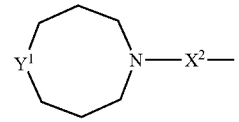

(b-8)

wherein
Y¹ is a bivalent radical of formula —NR²— or —CH(NR²R⁴)—;
X¹ is NR⁴, S, S(=O), S(=O)$_2$, O, CH$_2$, C(=O), C(=CH$_2$), CH(OH), CH(CH$_3$), CH(OCH$_3$), CH(SCH$_3$), CH(NR⁵ᵃR⁵ᵇ), CH$_2$—NR⁴ or NR⁴—CH$_2$;
X² is a direct bond, CH$_2$, C(=O), NR⁴, C$_{1-4}$alkyl-NR⁴, NR⁴—C$_{1-4}$alkyl; and
whereby each hydrogen atom in the carbocycles and the heterocycles defined in radicals (b-7) and (b-8) may optionally be replaced by R³; with the proviso that when R³ is hydroxy or C$_{1-6}$alkyloxy, then R³ can not replace a hydrogen atom in the α position relative to a nitrogen atom;

G is a direct bond or $C_{1-10}$alkanediyl;

$R^1$ is a monocyclic heterocycle selected from piperidinyl, piperazinyl, pyridyl, pyrazinyl, pyridazinyl, pyrimidinyl, pyrrolyl, furanyl, tetrahydrofuranyl, thienyl, oxazolyl, thiazolyl, imidazolyl, pyrazolyl, isoxazolyl, oxadiazolyl, and isothiazolyl; and each heterocycle may optionally be substituted with 1 or where possible more substituents selected from halo, hydroxy, amino, cyano, carboxy, $C_{1-6}$alkyl, $C_{1-6}$alkyloxy, $C_{1-6}$alkylthio, $C_{1-6}$alkyloxy$C_{1-6}$alkyl, aryl, aryl$C_{1-6}$alkyl, aryl$C_{1-6}$alkyloxy, hydroxy$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkylcarbonylamino, $C_{1-6}$alkyl-$SO_2$—$NR^{5c}$—, aryl-$SO_2$—$NR^{5c}$—, $C_{1-6}$alkyloxycarbonyl, —C(=O)—$NR^{5c}R^{5d}$, HO(—$CH_2$—$CH_2$—O)$_n$—, halo(—$CH_2$—$CH_2$—O)$_n$—, $C_{1-6}$alkyloxy(—$CH_2$—$CH_2$—O)$_n$—, aryl$C_{1-6}$alkyloxy(—$CH_2$—$CH_2$—O)$_n$— and mono- or di($C_{1-6}$alkyl)amino(—$CH_2$—$CH_2$—O)$_n$—;

each n independently is 1, 2, 3 or 4;

$R^2$ is hydrogen, formyl, $C_{1-6}$alkylcarbonyl, Hetcarbonyl, pyrrolidinyl, piperidinyl, homopiperidinyl, $C_{3-7}$cycloalkyl substituted with $N(R^6)_2$, or $C_{1-10}$alkyl substituted with $N(R^6)_2$ and optionally with a second, third or fourth substituent selected from amino, hydroxy, $C_{3-7}$cycloalkyl, $C_{2-5}$alkanediyl, piperidinyl, mono- or di($C_{1-6}$alkyl)amino, $C_{1-6}$alkyloxycarbonylamino, aryl and aryloxy;

$R^3$ is hydrogen, hydroxy, $C_{1-6}$alkyl, $C_{1-6}$alkyloxy, aryl $C_{1-6}$alkyl or aryl$C_{1-6}$alkyloxy;

$R^4$ is hydrogen, $C_{1-6}$alkyl or aryl$C_{1-6}$alkyl;

$R^{5a}$, $R^{5b}$, $R^{5c}$ and $R^{5d}$ each independently are hydrogen or $C_{1-6}$alkyl; or $R^{5a}$ and $R^{5b}$, or $R^{5c}$ and $R^{5d}$ taken together form a bivalent radical of formula —$(CH_2)_s$— wherein s is 4 or 5;

$R^6$ is hydrogen, $C_{1-4}$alkyl, formyl, hydroxy$C_{1-6}$alkyl, $C_{1-6}$alkylcarbonyl or $C_{1-6}$alkyloxycarbonyl;

aryl is phenyl or phenyl substituted with 1 or more substituents selected from halo, hydroxy, $C_{1-6}$alkyl, hydroxy$C_{1-6}$alkyl, polyhalo$C_{1-6}$alkyl, and $C_{1-6}$alkyloxy; and Het is pyridyl, pyrimidinyl, pyrazinyl, or pyridazinyl.

\* \* \* \* \*